(12) United States Patent
Yanuma

(10) Patent No.: US 10,448,807 B2
(45) Date of Patent: Oct. 22, 2019

(54) TREATMENT TOOL FOR ENDOSCOPE, AND METHOD FOR MANUFACTURING TREATMENT TOOL FOR ENDOSCOPE

(71) Applicant: OLYMPUS CORPORATION, Hachioji-shi, Tokyo (JP)

(72) Inventor: Yutaka Yanuma, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 114 days.

(21) Appl. No.: 15/730,562

(22) Filed: Oct. 11, 2017

(65) Prior Publication Data
US 2018/0042462 A1    Feb. 15, 2018

Related U.S. Application Data

(63) Continuation of application No. PCT/JP2016/054693, filed on Feb. 18, 2016.

(30) Foreign Application Priority Data

Apr. 15, 2015 (JP) .................................. 2015-083528

(51) Int. Cl.
   *A61B 1/00* (2006.01)
   *A61M 25/00* (2006.01)
   (Continued)

(52) U.S. Cl.
   CPC ............ *A61B 1/00098* (2013.01); *A61B 1/00* (2013.01); *A61B 1/00133* (2013.01);
   (Continued)

(58) Field of Classification Search
   CPC .. A61B 10/04; A61B 17/3421; A61B 18/1492; A61B 1/00; A61B 1/00098;
   (Continued)

(56) References Cited

U.S. PATENT DOCUMENTS 6,346,093 B1    2/2002  Allman et al.
6,733,473 B1    5/2004  Reifart et al.
(Continued)

FOREIGN PATENT DOCUMENTS

JP    2001-511023 A    8/2001
JP    2002-543937 A    12/2002
(Continued)

OTHER PUBLICATIONS

Nov. 7, 2018 Extended Search Report issued in European Patent Application No. 16779812.3.
(Continued)

*Primary Examiner* — Amanda K Hulbert
(74) *Attorney, Agent, or Firm* — Oliff PLC

(57) ABSTRACT

A treatment tool includes a second sheath (12) having a slit (12e) through which a guide wire is configured to be taken in and out of a first lumen, and a sheath-retaining part having a guide wire insertion opening (20b) having a slit (20c) and a main opening (20d), wherein a first end portion of the second sheath (12) has a first side cut surface (12g) and a second side cut surface (12h) intersecting in an X-shape, an axially cut surface formed by cutting in parallel to a central axis (O12) from an end surface (12k), an opening surrounded by the first side cut surface (12g), the second side cut surface (12h), and the axially cut surface and communicating with the first lumen at a position overlapping the main opening (20d), and a piece-like part.

6 Claims, 52 Drawing Sheets

(51) Int. Cl.
*A61M 25/01* (2006.01)
*A61M 25/09* (2006.01)
*A61B 17/34* (2006.01)
*A61B 18/14* (2006.01)
*A61B 1/01* (2006.01)
*A61B 1/018* (2006.01)
*A61B 10/04* (2006.01)
*A61B 17/00* (2006.01)
*A61B 17/22* (2006.01)
*A61B 18/00* (2006.01)

(52) U.S. Cl.
CPC ...... *A61B 1/00137* (2013.01); *A61B 17/3421* (2013.01); *A61B 18/1492* (2013.01); *A61M 25/00* (2013.01); *A61M 25/01* (2013.01); *A61M 25/0172* (2013.01); *A61M 25/09* (2013.01); *A61B 1/00135* (2013.01); *A61B 1/01* (2013.01); *A61B 1/018* (2013.01); *A61B 10/04* (2013.01); *A61B 2017/00469* (2013.01); *A61B 2017/22039* (2013.01); *A61B 2017/3445* (2013.01); *A61B 2018/00494* (2013.01); *A61B 2018/00601* (2013.01); *A61B 2018/00982* (2013.01); *A61B 2018/144* (2013.01); *A61M 2025/018* (2013.01); *A61M 2025/0188* (2013.01)

(58) Field of Classification Search
CPC ............ A61B 1/00133; A61B 1/00135; A61B 1/00137; A61B 1/01; A61B 1/018; A61B 2017/00469; A61B 2017/22039; A61B 2017/3445; A61B 2018/00494; A61B 2018/00601; A61B 2018/00982; A61B 2018/144; A61M 2025/018; A61M 2025/0188; A61M 25/00; A61M 25/01; A61M 25/0172; A61M 25/09

See application file for complete search history.

(56) References Cited

U.S. PATENT DOCUMENTS 6,879,854 B2    4/2005  Windheuser et al.
2014/0018800 A1  1/2014  Yanuma

FOREIGN PATENT DOCUMENTS

| JP | 2009-526616 A | 7/2009 |
| JP | 2010-517735 A | 5/2010 |
| JP | 2011-509718 A | 3/2011 |
| JP | 2012-518481 A | 8/2012 |
| JP | 2014-511237 A | 5/2014 |
| WO | 1998/010821 A1 | 3/1998 |
| WO | 2000/69499 A1 | 11/2000 |
| WO | 2007/095252 A1 | 8/2007 |
| WO | 2009/091836 A1 | 7/2009 |
| WO | 2009/105089 A2 | 8/2009 |
| WO | 2010/096697 A1 | 8/2010 |
| WO | 2012/115753 A1 | 8/2012 |

OTHER PUBLICATIONS

Mar. 27, 2018 Notice of Allowance issued in Japanese Patent Application No. 2015-083528.
Apr. 19, 2016 International Search Report issued in International Patent Application No. PCT/JP2016/054693.

TREATMENT TOOL FOR ENDOSCOPE, AND METHOD FOR MANUFACTURING TREATMENT TOOL FOR ENDOSCOPE

FIELD OF THE INVENTION

The present invention relates to a treatment tool for an endoscope and a method for manufacturing a treatment tool for an endoscope. This application is a continuation application based on a PCT International Application No. PCT/JP2016/054693, filed on Feb. 18, 2016, whose priority is claimed on Japanese Patent Application No. 2015-083528, filed Apr. 15, 2015. Both of the content of the PCT International Application and the Japanese Application are incorporated herein by reference.

DESCRIPTION OF RELATED ART

Various treatment tools having a treatment part at a distal end portion and having a multi-lumen sheath extending from the distal end portion and the treatment part toward a proximal end side are known as treatment tools for an endoscope. For example, a treatment tool used by being inserted into a bile duct, a dilation balloon configured to dilate a duodenal papilla, and a dilation balloon with a knife in which an incision knife configured to incise the duodenal papilla is combined with the dilation balloon can be cited as examples of such a treatment tool for an endoscope.

The treatment tool for an endoscope is inserted into a patient's body along a guide wire indwelled in the patient's body. A guide wire lumen for inserting the guide wire is provided in a multi-lumen sheath of the treatment tool for an endoscope.

An insertion opening for inserting the guide wire into the guide wire lumen from a proximal end side is provided at the proximal end side (proximal side) in an insertion direction of the treatment tool for an endoscope. The insertion opening is provided, for example, at a distal end portion of an operation part in the treatment tool for an endoscope. The insertion opening communicates with an opening formed at a side of a proximal end portion of the guide wire lumen in the multi-lumen sheath.

To facilitate the operation of inserting the treatment tool for an endoscope into a patient's body, there is a case in which the treatment tool for an endoscope is configured so that the guide wire can be taken in and out of the guide wire lumen even at an appropriate position between a distal end portion of the treatment tool for an endoscope and the insertion opening. In this case, a slit that has a narrower width than an outer diameter of the guide wire and communicates with the guide wire lumen is formed in the multi-lumen sheath along a longitudinal direction of the guide wire lumen. Further, a slit that has a wider width than the outer diameter of the guide wire extends in a longitudinal direction of the treatment tool for an endoscope and is formed at a distal end side of the insertion opening in the operation part.

In the treatment tool for an endoscope, the guide wire inserted into the insertion opening at the proximal end side can be inserted along the guide wire lumen. However, an operator can allow the guide wire to pass through the respective slits formed in the operation part and the multi-lumen sheath and be taken out of the lumen from a side of the multi-lumen sheath. Because of this, it is possible to perform an operation of the guide wire even beside the patient.

For example, a treatment tool having slits formed at distal end sides of a multi-lumen sheath and an operation part is described in U.S. Pat. No. 6,879,854.

However, the above-described conventional treatment tool for an endoscope has a problem in that it becomes difficult to insert the guide wire as the number of lumens of a multi-lumen tube increases.

First, a conventional treatment tool for an endoscope having a multi-lumen sheath with a small number of lumens will be described with reference to FIGS. 65 to 68.

FIG. 65 is a schematic perspective view illustrating a proximal end portion of a multi-lumen tube according to an example of a treatment tool for an endoscope of a prior art. FIG. 66 is a schematic perspective view illustrating a constitution in the vicinity of a guide wire insertion opening. FIGS. 67 and 68 are explanatory views of operation of the treatment tool for an endoscope of the prior art according to the example.

As illustrated in FIGS. 65 and 66, a treatment tool 201 of the prior art according to the example includes a multi-lumen sheath 212 fitted in a distal end tubular part 220a of an operation part main body 220 at a proximal end side (see FIG. 66).

Three lumens, a first lumen 212a, a second lumen 212b, and a third lumen 212c, extend in a longitudinal direction of the multi-lumen sheath 212 and are formed inside the multi-lumen sheath 212. The first lumen 212a is a through-hole into which a guide wire (not illustrated) is inserted. The second lumen 212b and the third lumen 212c are through-holes having a smaller diameter than the first lumen 212a.

The second lumen 212b and the third lumen 212c may, for example, have a linear member inserted thereinto or a fluid circulating therethrough according to use of the treatment tool 201.

A slit 212e extending along the longitudinal direction of the multi-lumen sheath 212 and communicating with the first lumen 212a is formed in the first lumen 212a. A clearance width of the slit 212e is narrower than an outer shape of the guide wire (not illustrated).

An insertion opening 212i for the guide wire is formed at a proximal end portion of the multi-lumen sheath 212 by partially cutting a sidewall part of the first lumen 212a. An axially cut surface 212f and a side cut surface 212g are formed around the insertion opening 212i.

The axially cut surface 212f is a plane formed by cutting from a proximal end surface 212k of the multi-lumen sheath 212 (see FIG. 65) in a longitudinal direction and passing through an approximate center of the first lumen 212a.

The side cut surface 212g is a plane formed by cutting from an outer circumferential surface, at which the slit 212e is formed, in a direction orthogonal to the longitudinal direction of the multi-lumen sheath 212 toward a distal end portion in a cutting direction of the axially cut surface 212f.

As illustrated in FIG. 66, the proximal end portion of the multi-lumen sheath 212 is inserted into the distal end tubular part 220a of the operation part main body 220 and fixed to the operation part main body 220.

A guide wire insertion opening 220b is formed in the distal end tubular part 220a. The guide wire insertion opening 220b is located at a position facing the insertion opening 212i of the multi-lumen sheath 212.

The guide wire insertion opening 220b is a substantially rectangular opening elongated in an axial direction of the multi-lumen sheath 212 and the distal end tubular part 220a. A width in a short-side direction of the guide wire insertion opening 220b has a dimension almost equal to a width in a short-side direction of the insertion opening 212i.

A slit 220c passing through to a distal end of the distal end tubular part 220a is formed at a distal end of the guide wire insertion opening 220b in a longitudinal direction.

At a position overlapping the slit 212e of the multi-lumen sheath 212, the slit 220c extends coaxially with the slit 212e. A clearance width of the slit 220c is wider than an outer diameter of the guide wire (not illustrated) and is narrower than the width in the short-side direction of the guide wire insertion opening 220b.

In the distal end tubular part 220a, a guide part 220j that has a C-shaped cross-section and is fitted over the multi-lumen sheath 212 is formed at a more distal end side than the guide wire insertion opening 220b.

The side cut surface 212g of the multi-lumen sheath 212 is fixed at a position that is an intermediate portion of the guide part 220j in the longitudinal direction. Because of this, as illustrated in FIG. 67, a proximal end side (the right side in the drawing) of the guide part 220j covers the insertion opening 212i further toward the proximal end side than the side cut surface 212g.

The operation of inserting a guide wire 230 from the guide wire insertion opening 220b of the treatment tool 201 will be described with reference to FIGS. 67 and 68.

As illustrated in FIG. 67, an operator inserts the guide wire 230 into the guide wire insertion opening 220b from a side of the operation part main body 220 and inserts the guide wire 230 into the first lumen 212a covered with the guide part 220j.

When the operator inserts a distal end portion 230a of the guide wire 230 between the guide part 220j and the axially cut surface 212f, as illustrated in FIG. 68, the guide wire 230 is guided by the guide part 220j. When the operator sends the guide wire 230 further toward the distal end side, the distal end portion 230a abuts the side cut surface 212g.

In the multi-lumen sheath 212, the number of lumens is small and the diameter of the first lumen 212a is large. Because of this, the side cut surface 212g has an arc shape, and a width of the side cut surface 212g in a diametric direction is smaller than an outer diameter of the guide wire 230. Because of this, only a part of the distal end portion 230a of the guide wire 230 comes into contact with the side cut surface 212g in a state of protruding inward in the diametric direction from the side cut surface 212g.

Because of this, when the operator continues the insertion, the distal end portion 230a slides and moves on the side cut surface 212g and enters the inside of the first lumen 212a. When the distal end portion 230a enters the first lumen 212a, the guide wire 230 is smoothly inserted therein along an inner circumferential surface of the first lumen 212a.

As described above, even when the guide wire 230 is inserted at a position deviating from the first lumen 212a of the treatment tool 201 and is caught by the side cut surface 212g, the operator can insert the guide wire 230 into the first lumen 212a just by pushing the guide wire 230 further.

Nowadays, treatment tools for an endoscope are becoming multi-functional and miniaturized, and there are cases in which the number of lumens in a multi-lumen sheath used for a treatment tool for an endoscope is increased, or a multi-lumen sheath includes a lumen having a larger diameter than a guide wire lumen into which a guide wire is inserted. For example, when a treatment tool for an endoscope is a dilation balloon, a balloon lumen through which a fluid for dilating the balloon passes is required. To shorten a contraction time of a balloon, an inner diameter of the balloon lumen should be made as large as possible. In this case, the inner diameter of the balloon lumen is sometimes equal to or larger than an inner diameter of the guide wire lumen. In such a treatment tool for an endoscope, because the guide wire lumen has a small diameter, a guide wire cannot be smoothly inserted therein in some cases.

This point will be described with reference to FIGS. 69 to 73 using another example of a conventional treatment tool for an endoscope having a multi-lumen sheath to which a large-diameter lumen is added.

FIG. 69 is a schematic perspective view illustrating a proximal end portion of a multi-lumen tube according to another example of a treatment tool for an endoscope of the prior art. FIG. 70 is a schematic perspective view illustrating a constitution in the vicinity of a guide wire insertion opening. FIG. 71 is a view for describing operation of the treatment tool for an endoscope of the prior art according to another example. FIG. 72 is a plan view viewed from a direction of Z in FIG. 71. FIG. 73 is a cross-sectional view taken along line R-R in FIG. 72.

As illustrated in FIGS. 69 and 70, instead of the multi-lumen sheath 212 of the treatment tool 201, a treatment tool 241 according to another example of the prior art includes a multi-lumen sheath 242 having an outer diameter equal to that of the multi-lumen sheath 212. Hereinafter, points different from the treatment tool 201 will be mainly described. Like reference numerals will be given to members, parts, and the like identical or corresponding to those of the treatment tool 201, and overlapping descriptions will be omitted.

Instead of the first lumen 212a of the treatment tool 201, the multi-lumen sheath 242 includes a first lumen 242a having a smaller diameter. Also, the multi-lumen sheath 242 includes a fourth lumen 242d having a diameter substantially equal to that of the first lumen 242a.

The first lumen 242a and the fourth lumen 242d are arranged at positions facing each other across a central axis O242 of the multi-lumen sheath 242. The second lumen 212b and the third lumen 212c are also arranged at positions facing each other across the central axis O242 of the multi-lumen sheath 242. However, a direction in which the second lumen 212b and the third lumen 212c face each other is a direction orthogonal to a direction in which the first lumen 242a and the fourth lumen 242d face each other.

The center of the first lumen 242a is disposed more outward in a diametric direction than the center of the first lumen 212a in the treatment tool 201 with respect to the center of the multi-lumen sheath 242.

As with the multi-lumen sheath 212, an insertion opening 242i of a guide wire is formed at a proximal end portion of the multi-lumen sheath 242 by partially cutting a sidewall part of the first lumen 242a. An axially cut surface 242f and a side cut surface 242g are formed around the insertion opening 242i.

The axially cut surface 242f is a plane formed by cutting from a proximal end surface 212k of the multi-lumen sheath 242 in the longitudinal direction and passes through an approximate center of the first lumen 242a.

The side cut surface 242g is a plane formed by cutting from an outer circumferential surface at which the slit 212e is formed in a direction orthogonal to the longitudinal direction of the multi-lumen sheath 242 toward a distal end portion in a cutting direction of the axially cut surface 242f.

As illustrated in FIG. 70, as with the multi-lumen sheath 212, the proximal end portion of the multi-lumen sheath 242 is inserted into the distal end tubular part 220a of the operation part main body 220 and fixed to the operation part main body 220.

The operation of inserting the guide wire 230 from the guide wire insertion opening 220b of the treatment tool 241 will be described with reference to FIGS. 71 to 73.

As in the case of the treatment tool 201, an operator inserts the guide wire 230 into the guide wire insertion opening 220b from a side of the operation part main body 220 and inserts the guide wire 230 into the first lumen 242a covered with the guide part 220j.

As illustrated in FIG. 71, the operator inserts the distal end portion 230a of the guide wire 230 between the guide part 220j and the axially cut surface 242f. When the operator sends the guide wire 230 further toward the distal end side, the distal end portion 230a abuts the side cut surface 242g.

In the multi-lumen sheath 242, the number of lumens is larger than the multi-lumen sheath 212, and the inner diameter of the first lumen 242a is smaller than the inner diameter of the first lumen 212a. Because of this, as illustrated in FIG. 73, a width of the side cut surface 242g in the diametric direction is wider than the width in the diametric direction of the side cut surface 212g. Because of this, for example, a portion at which the width in the diametric direction of the side cut surface 242g is equal to or larger than the outer diameter of the guide wire 230 is formed.

When the distal end portion 230a of the guide wire 230 comes into contact with such a wide-width portion in the side cut surface 242g, the entire distal end portion 230a is pressed by the side cut surface 242g. Because of this, due to a frictional force, the distal end portion 230a is locked to the side cut surface 242g.

As a result, even when the operator continues the insertion, the distal end portion 230a does not move inside the first lumen 242a in some cases.

As described above, in the treatment tool 241, the distal end portion 230a of the guide wire 230 may be easily caught by the side cut surface 242g and be unable to advance. When the distal end portion 230a is caught by the side cut surface 242g and cannot advance, the operator needs to pull the guide wire 230 back and attempt insertion again or perform insertion while positioning the guide wire 230 so that the distal end portion 230a enters the first lumen 242a.

Because of this, workability of the operation of inserting the guide wire 230 is deteriorated.

SUMMARY OF THE INVENTION

According to a first aspect of the present invention, a treatment tool for an endoscope includes a multi-lumen sheath having a plurality of lumens including a guide wire lumen into which a guide wire is inserted, and a first slit extending along an axial direction of the guide wire lumen and through which the guide wire is configured to be taken in and out of the guide wire lumen, and a sheath-retaining part including a tubular part configured to retain a first end portion of the multi-lumen sheath and having a guide wire insertion opening formed at a side surface of the tubular part, the guide wire insertion includes a second slit overlapping the first slit when viewed from a diametric direction and having a wider clearance than the first slit and a main opening having a wider opening width than the second slit formed in that order from a distal end side, wherein the first end portion of the multi-lumen sheath has a first side cut surface and a second side cut surface formed by being intersected in an X-shape having the first slit of the multi-lumen sheath as a center when viewed from the diametric direction and cutting the multi-lumen sheath from an outer circumferential surface of the multi-lumen sheath to an inside of the guide wire lumen, an axially cut surface formed by cutting the multi-lumen sheath in parallel with a central axis of the guide wire lumen from an axial end surface side of the first end portion of the multi-lumen sheath to a position intersecting a part of the first side cut surface and a part of the second side cut surface, an opening surrounded by a portion disposed in the vicinity of the axial end surface of the first end portion in the first side cut surface, the second side cut surface, and the axially cut surface and communicating with the guide wire lumen, formed at a position overlapping the main opening, a first piece-like part having the first side cut surface and the axially cut surface at an outer edge thereof, and a second piece-like part having the second side cut surface and the axially cut surface at an outer edge thereof.

In the treatment tool for an endoscope, the first side cut surface and the second side cut surface may be orthogonal to the axially cut surface.

In the treatment tool for an endoscope, the first side cut surface and the second side cut surface may be arranged at a position further toward the distal end side than the guide wire insertion opening when viewed from the diametric direction and overlapping the tubular part.

According to a second aspect of the present invention, a method for manufacturing a treatment tool for an endoscope is a method for manufacturing a treatment tool for an endoscope, the treatment tool including a multi-lumen sheath having a plurality of lumens including a guide wire lumen into which a guide wire is inserted and a first slit extending along an axial direction of the guide wire lumen and through which the guide wire is configured to be taken in and out of the guide wire lumen, and a sheath-retaining part including a tubular part configured to retain a first end portion of the multi-lumen sheath, and includes forming, in the first end portion of the multi-lumen sheath, a first side cut surface and a second side cut surface by forming an X-shape intersecting in an axial direction of the multi-lumen sheath and cutting the multi-lumen sheath from an outer circumferential surface of the multi-lumen sheath to an inside of the guide wire lumen, forming, in the first end portion of the multi-lumen sheath, an axially cut surface formed by cutting the multi-lumen sheath in parallel with a central axis of the guide wire lumen from an axial end surface side of the first end portion of the multi-lumen sheath to a position intersecting a part of the first side cut surface and a part of the second side cut surface, forming, in the first end portion of the multi-lumen sheath, an opening communicating with the guide wire lumen, a first piece-like part having the first side cut surface and the axially cut surface at an outer edge thereof, and a second piece-like part having the second side cut surface and the axially cut surface at an outer edge thereof by forming the axially cut surface, and forming, in the first end portion of the multi-lumen sheath, a first slit passing through an intersection part between the first side cut surface and the second side cut surface via the opening, extending along the axial direction of the guide wire lumen, and communicating with the guide wire lumen.

DETAILED DESCRIPTION OF THE INVENTION

Figure 1:
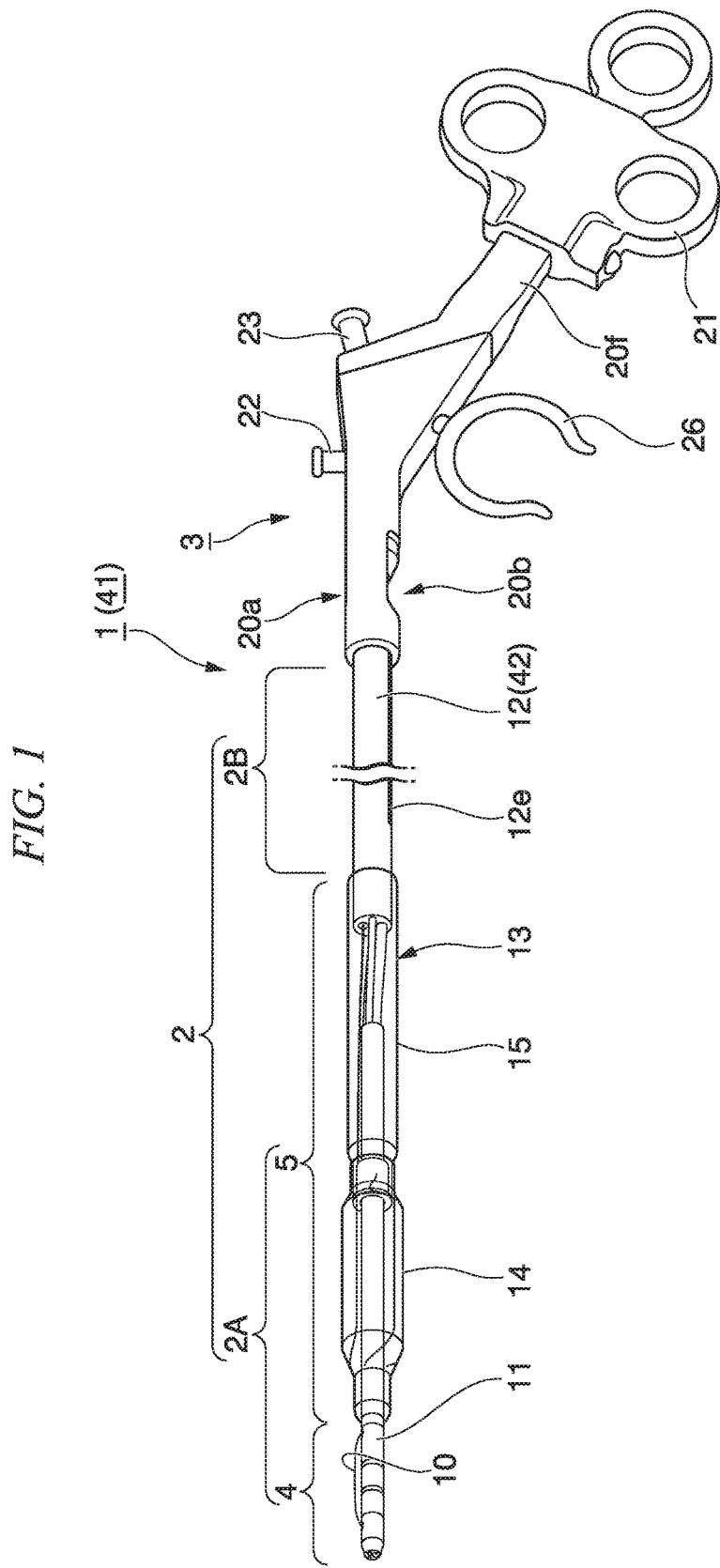
FIG. 1 is a schematic perspective view illustrating a constitution of a treatment tool for an endoscope according to a first embodiment of the present invention.

Hereinafter, embodiments of the present invention will be described with reference to the accompanying drawings. In all of the drawings, like reference numerals are given to like or corresponding members, and overlapping descriptions are omitted even when embodiments are different.

[First Embodiment]

A treatment tool for an endoscope according to a first embodiment of the present invention will be described.

Figure 2:
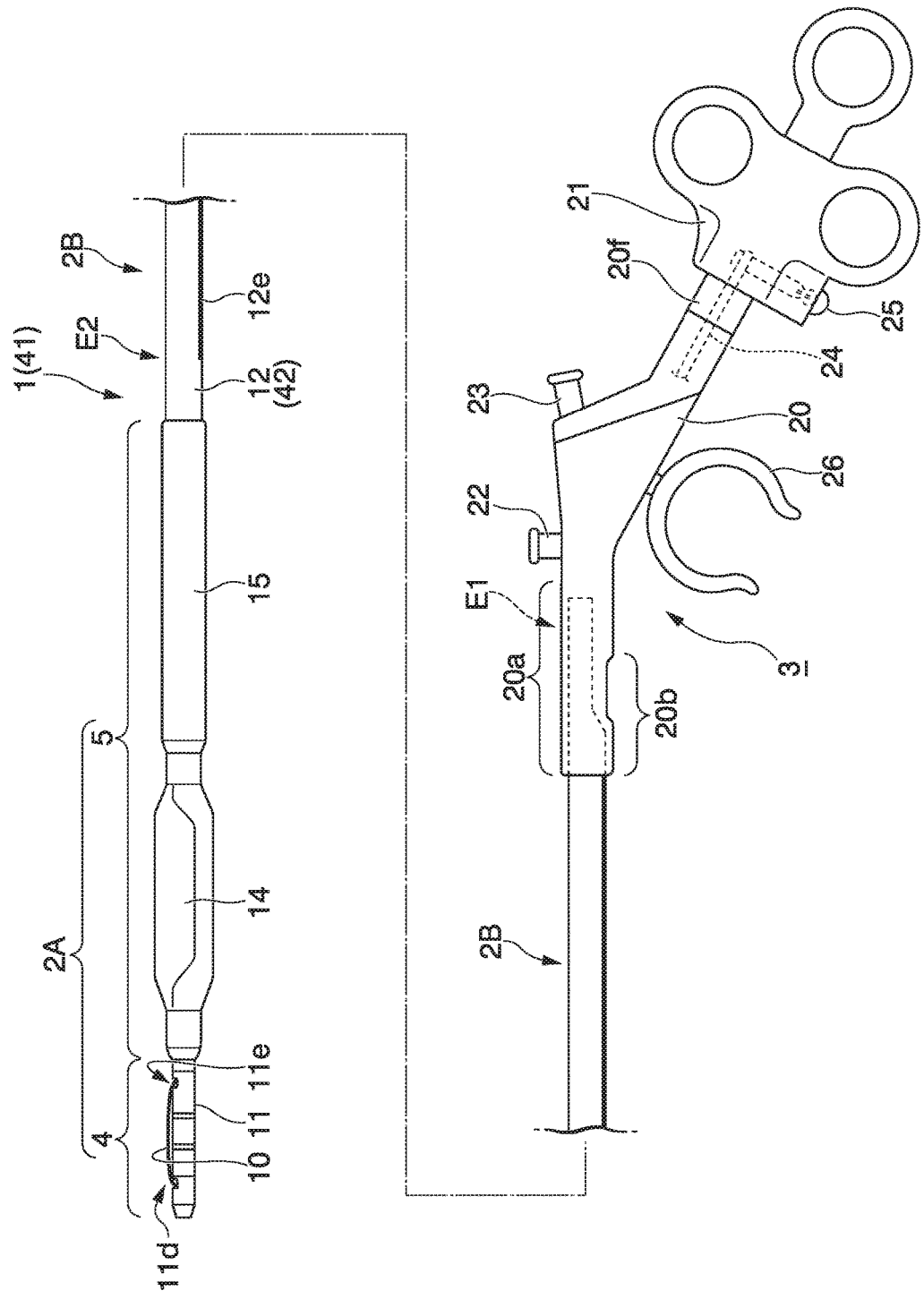
FIG. 2 is a schematic front view illustrating the constitution of the treatment tool for an endoscope according to the first embodiment of the present invention.
Figure 3:
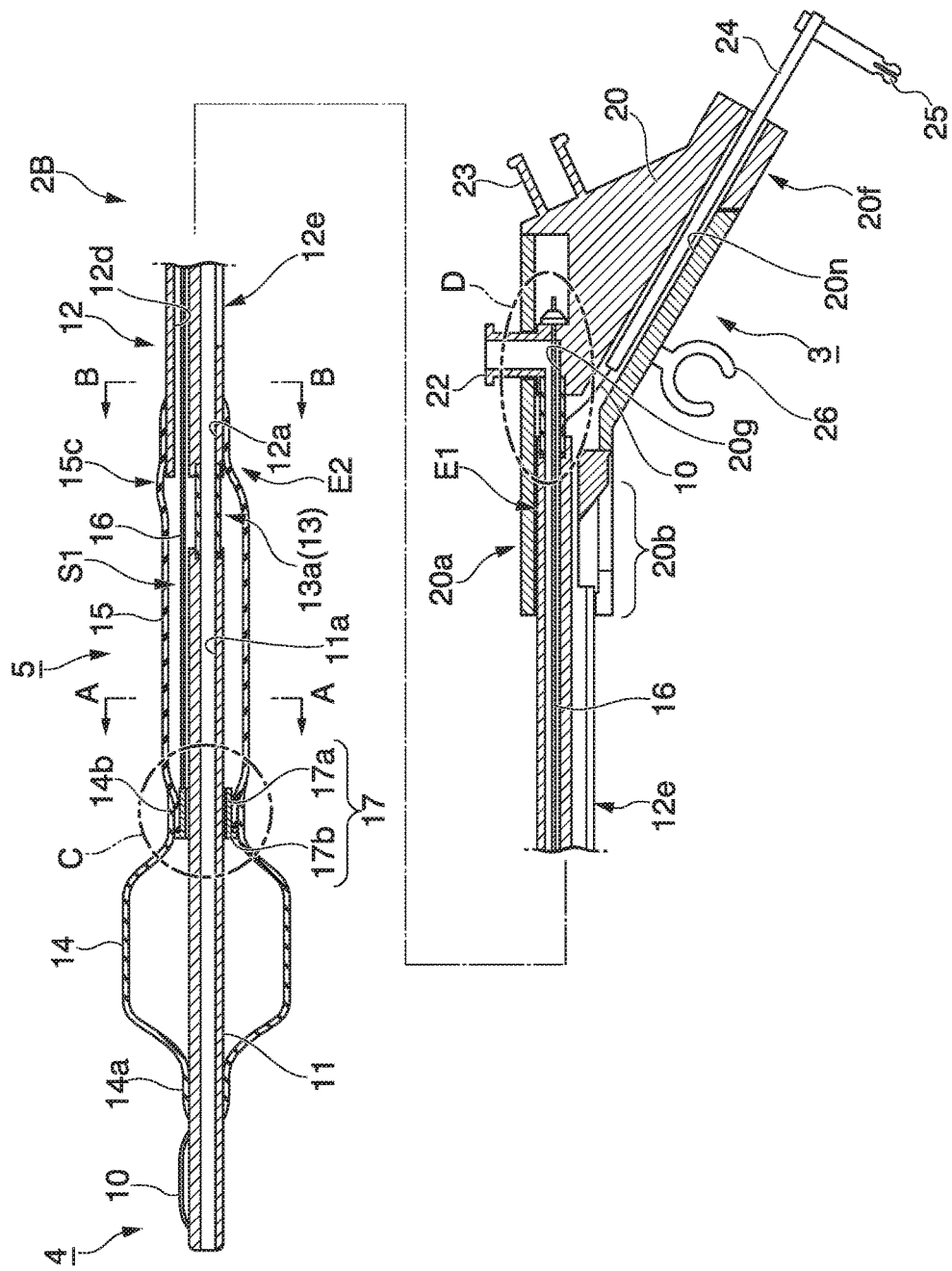
FIG. 3 is a schematic cross-sectional view along a longitudinal direction of the treatment tool for an endoscope according to the first embodiment of the present invention.
Figure 4:
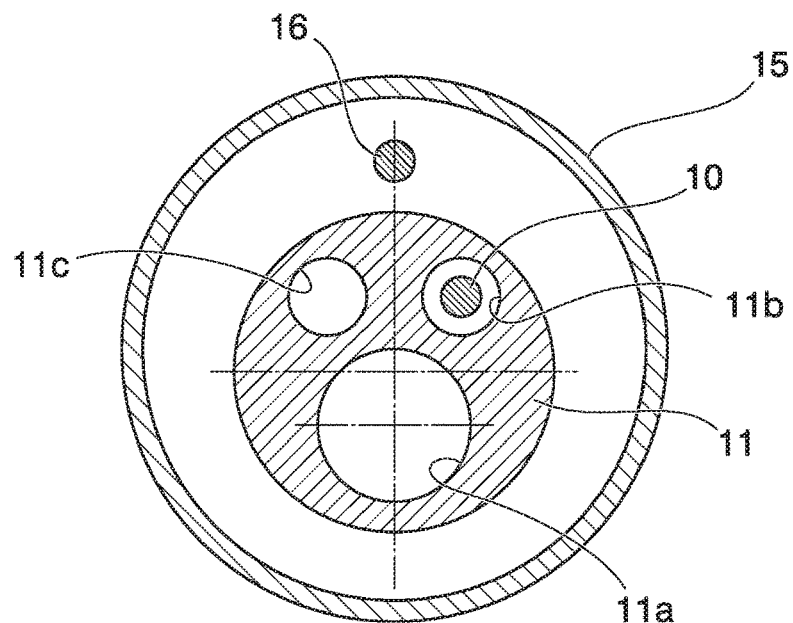
FIG. 4 is a cross-sectional view taken along line A-A in FIG. 3.
Figure 5:
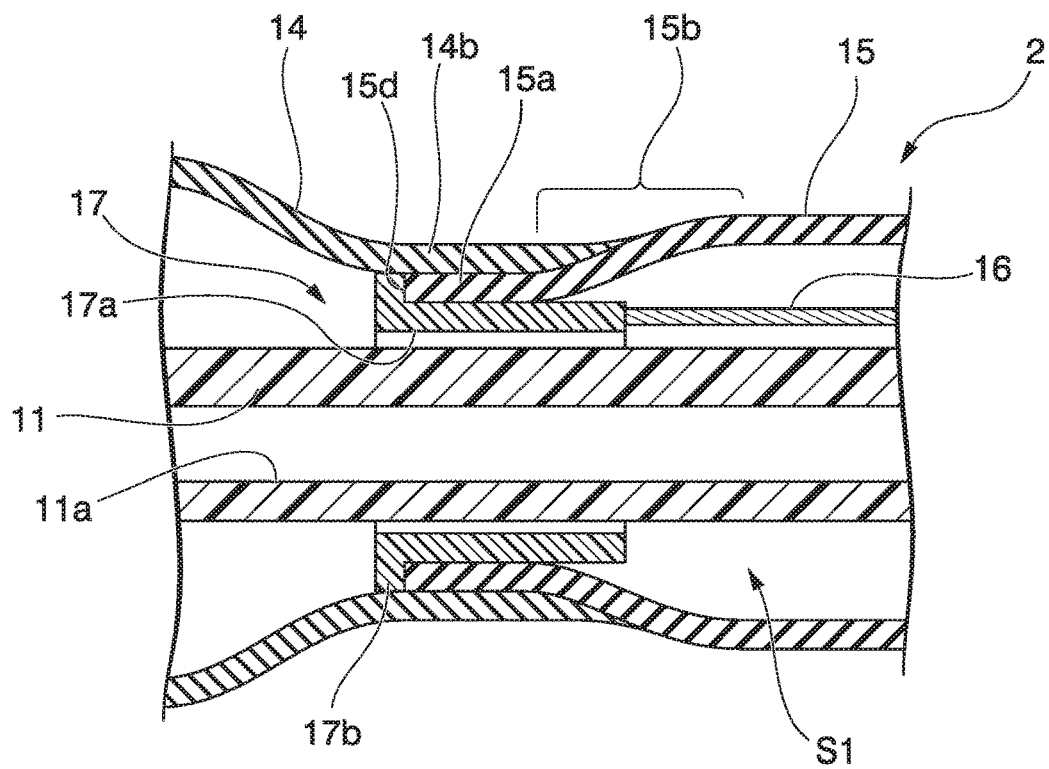
FIG. 5 is an enlarged view of portion C in FIG. 3.
Figure 6:
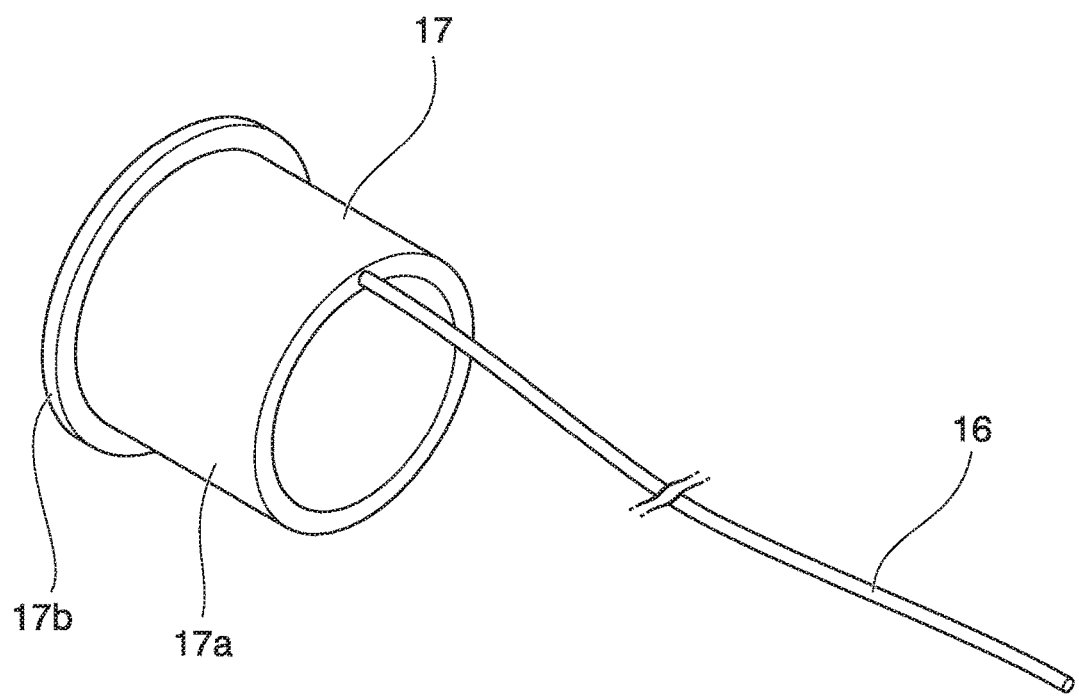
FIG. 6 is a schematic perspective view illustrating a constitution of an elongation suppressing wire of the treatment tool for an endoscope according to the first embodiment of the present invention.
Figure 7:
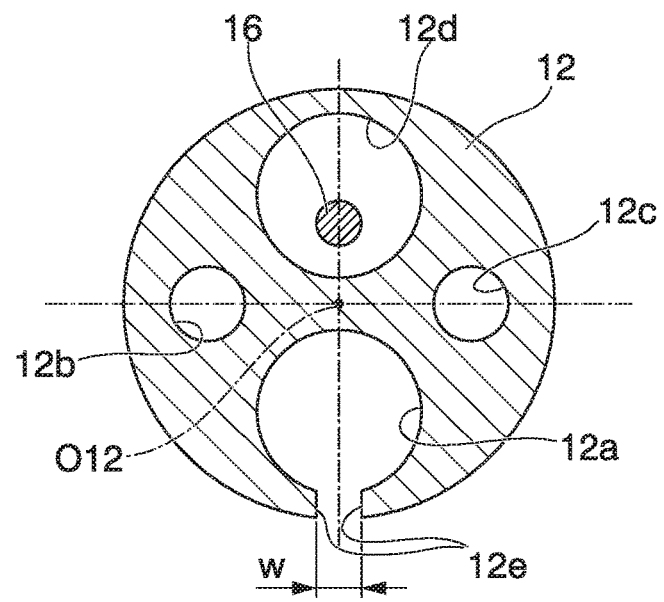
FIG. 7 is a cross-sectional view taken along line B-B in FIG. 3.
Figure 8:
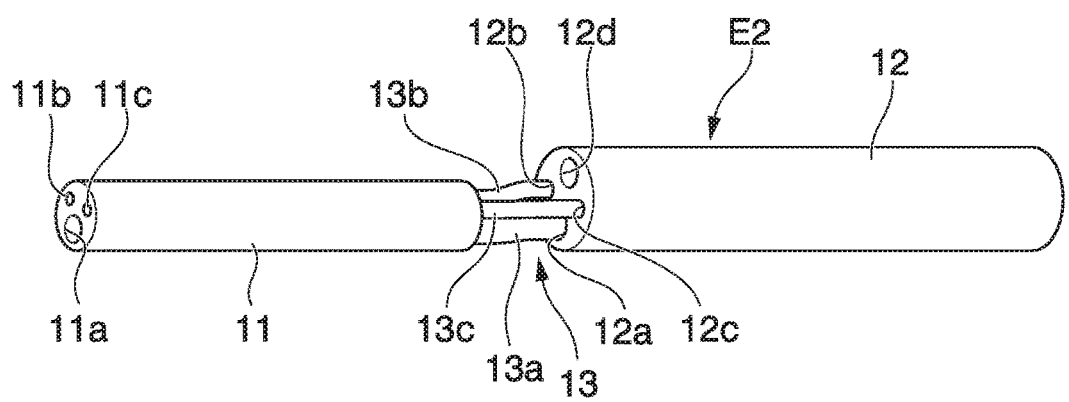
FIG. 8 is a schematic perspective view illustrating a constitution inside a balloon tube of the treatment tool for an endoscope according to the first embodiment of the present invention.
Figure 9:
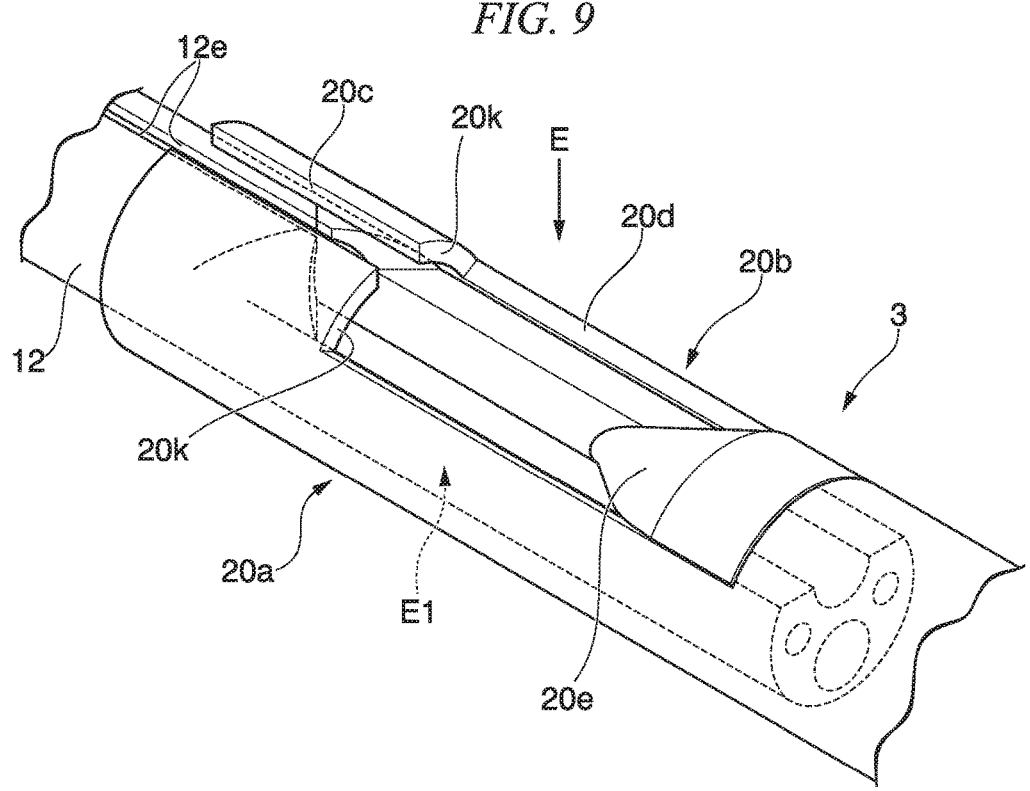
FIG. 9 is a schematic perspective view illustrating a constitution in the vicinity of a guide wire insertion opening of the treatment tool for an endoscope according to the first embodiment of the present invention.
Figure 10:
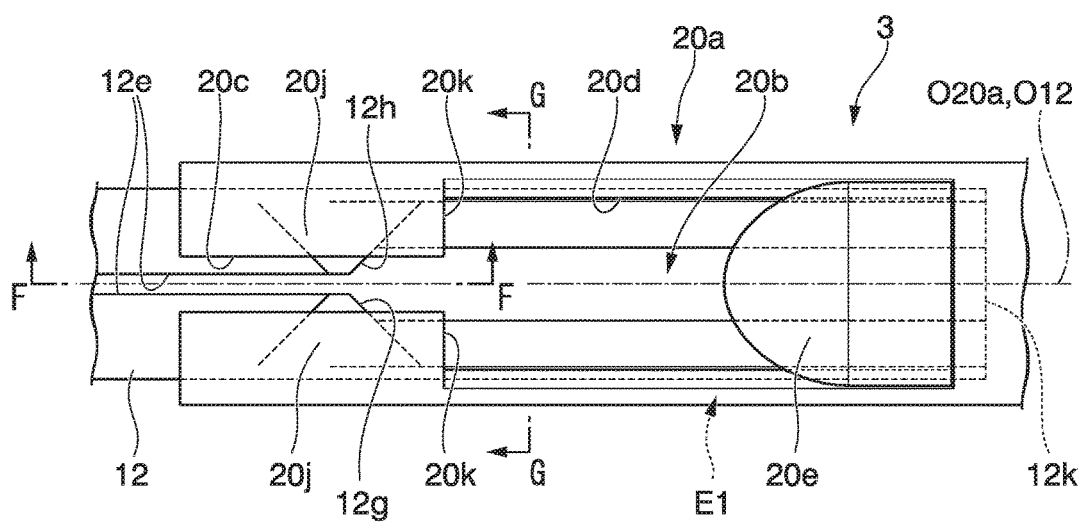
FIG. 10 is a plan view viewed from a direction of E in FIG. 9.
Figure 11:
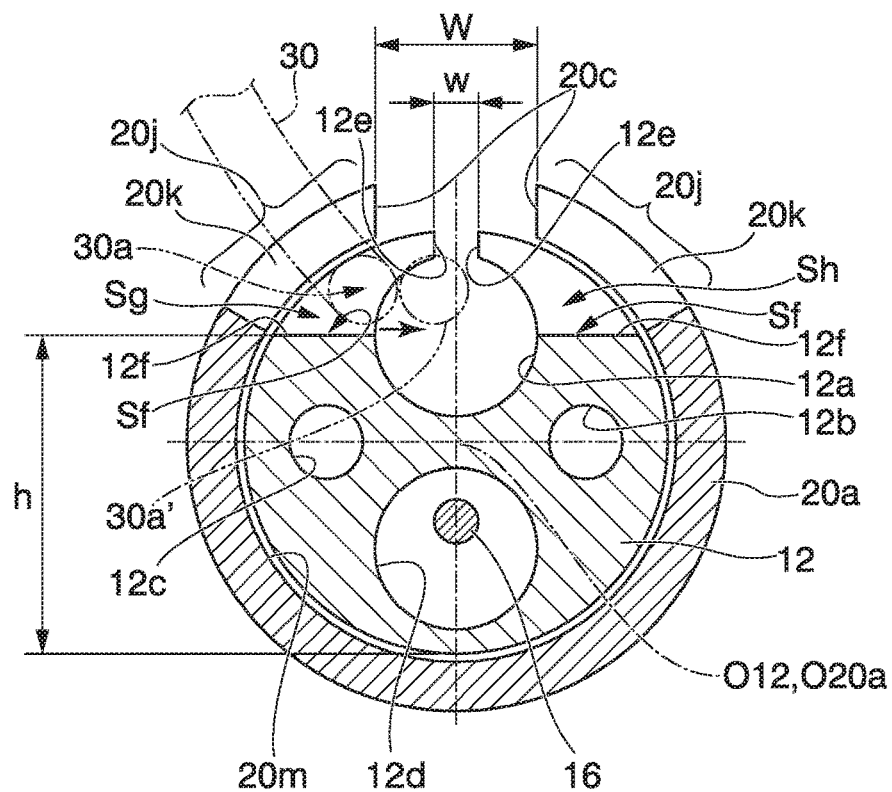
FIG. 11 is a cross-sectional view taken along line G-G in FIG. 10.
Figure 12:
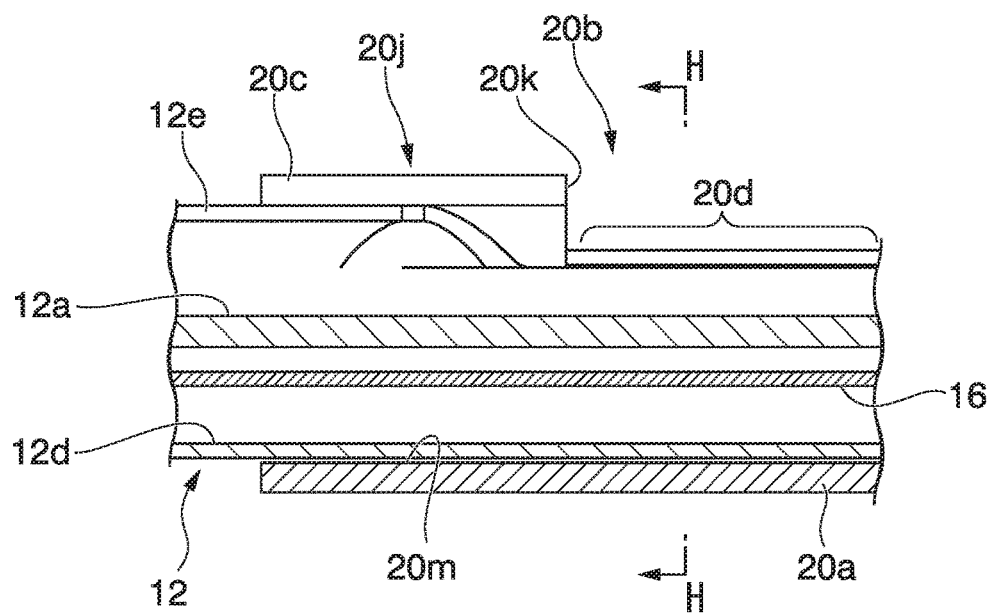
FIG. 12 is a cross-sectional view taken along line F-F in FIG. 10.
Figure 13:
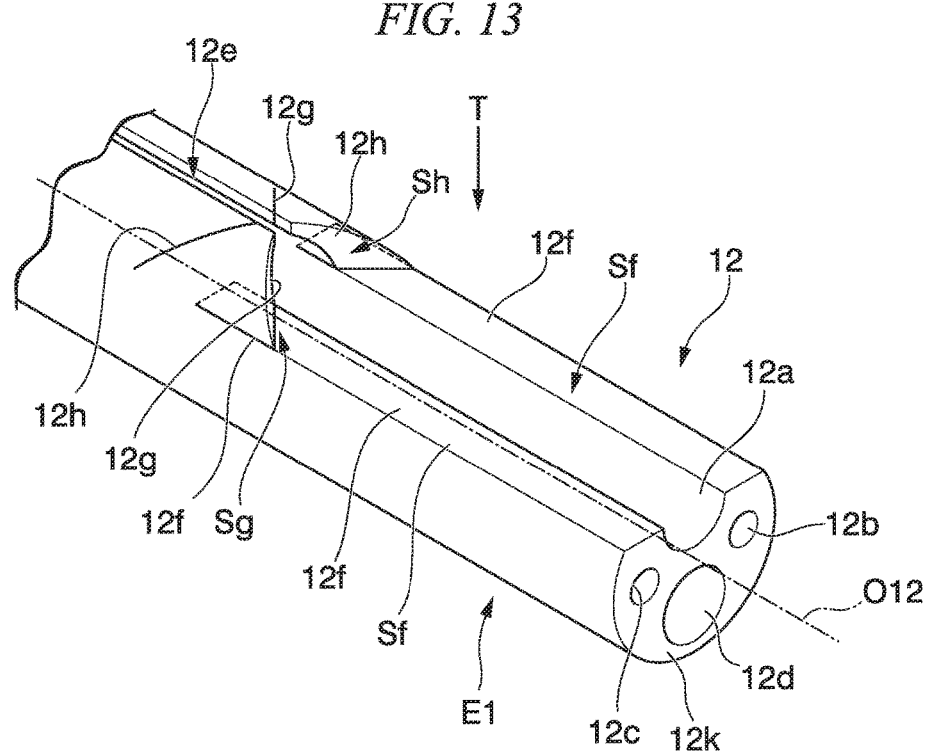
FIG. 13 is a schematic perspective view illustrating a constitution of a second end portion of a second sheath of the treatment tool for an endoscope according to the first embodiment of the present invention.
Figure 14:
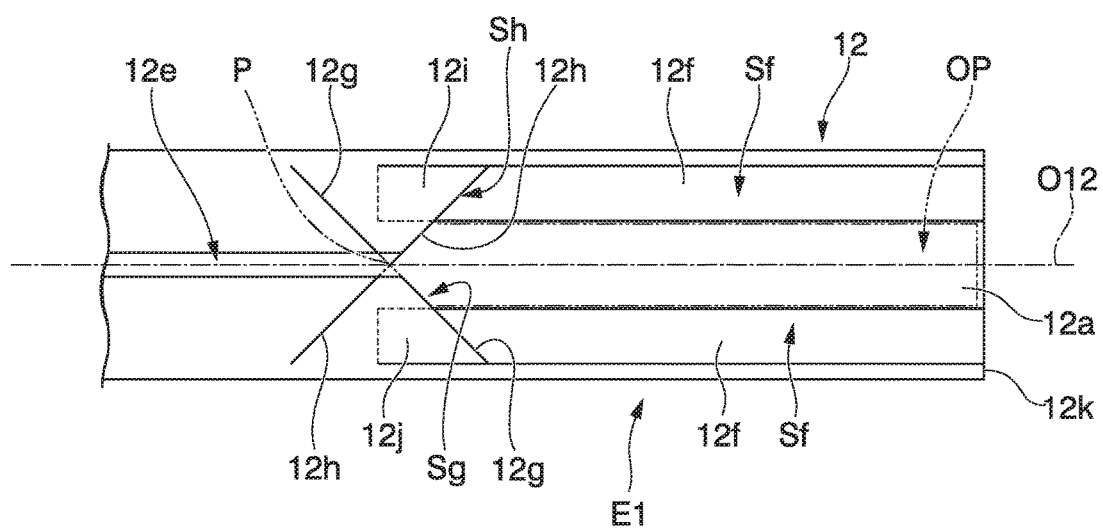
FIG. 14 is a plan view viewed from a direction of T in FIG. 13.
Figure 15:
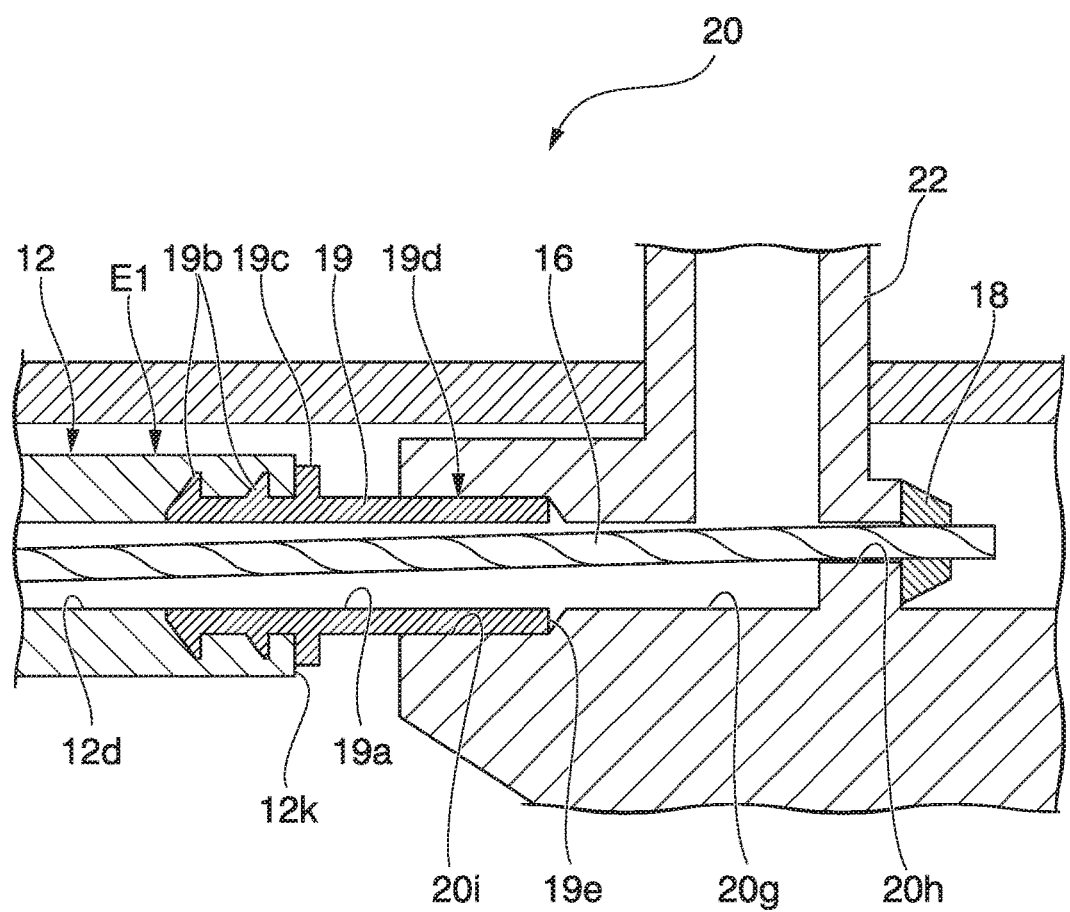
FIG. 15 is an enlarged view of portion D in FIG. 3.

FIG. 1 is a schematic perspective view illustrating a constitution of the treatment tool for an endoscope according to the first embodiment of the present invention. FIG. 2 is a schematic front view illustrating the constitution of the treatment tool for an endoscope according to the first embodiment of the present invention. FIG. 3 is a schematic cross-sectional view along a longitudinal direction of the treatment tool for an endoscope according to the first embodiment of the present invention. FIG. 4 is a cross-sectional view taken along line A-A in FIG. 3. FIG. 5 is an enlarged view of portion C in FIG. 3. FIG. 6 is a schematic perspective view illustrating a constitution of an elongation suppressing wire of the treatment tool for an endoscope according to the first embodiment of the present invention. FIG. 7 is a cross-sectional view taken along line B-B in FIG. 3. FIG. 8 is a schematic perspective view illustrating a constitution inside a balloon tube of the treatment tool for an endoscope according to the first embodiment of the present invention. FIG. 9 is a schematic perspective view illustrating a constitution in the vicinity of a guide wire insertion opening of the treatment tool for an endoscope according to the first embodiment of the present invention. FIG. 10 is a plan view viewed from a direction of E in FIG. 9. FIG. 11 is a cross-sectional view taken along line G-G in FIG. 10. FIG. 12 is a cross-sectional view taken along line F-F in FIG. 10. FIG. 13 is a schematic perspective view illustrating a constitution of a second end portion of a second sheath of the treatment tool for an endoscope according to the first embodiment of the present invention. FIG. 14 is a plan view viewed from a direction of T in FIG. 13. FIG. 15 is an enlarged view of portion D in FIG. 3.

Because each of the drawings is a schematic view, shapes or dimensions are exaggerated therein (the same applies to the drawings below).

As illustrated in FIGS. 1 to 3, a treatment tool 1 (a treatment tool for an endoscope) according to the present embodiment includes an insertion part 2 inserted into a patient's body and an operation part 3 configured to perform an operation of the treatment tool 1 from outside the patient's body.

The insertion part 2 is a long linear member. The insertion part 2 is inserted into the patient's body through a treatment tool channel of an endoscope.

In the present specification, when describing relative positions in the treatment tool 1, a distal end side (distal side) in an insertion direction with respect to a patient is simply referred to as a "distal end side," and a proximal end side (proximal side), which is the opposite side thereof (a side at which the operation part 3 is provided), is simply referred to as a "proximal end side" unless indicated otherwise. In the present specification, when describing relative positions related to an axial or tubular member (including a part) that can specify an axis such as a central axis, an "axial direction," a "circumferential direction," and a "diametric direction" are used in some cases. The axial direction is a direction along an axis. The circumferential direction is a direction that revolves around the axis. The diametric direction is a direction along a line intersecting the axis on a plane orthogonal to the axis. In the diametric direction, a direction receding from the axis is referred to as outward in the diametric direction, and a direction approaching the axis is referred to as inward in the diametric direction in some cases.

The insertion part 2 includes a distal end side insertion part 2A and a proximal end side insertion part 2B in that order from the distal end side toward the proximal end side.

The distal end side insertion part 2A includes a treatment part 4 and a balloon part 5 in that order from the distal end side toward the proximal end side. A first sheath 11 is inserted into the balloon part 5.

As illustrated in FIG. 4, the first sheath 11 is a multi-lumen sheath through which three lumens, a first lumen 11a (guide wire lumen), a second lumen 11b, and a third lumen 11c, pass in the axial direction.

The first lumen 11a is a through-hole into which a guide wire (not illustrated) configured to guide insertion of the treatment tool 1 into a patient's body is inserted. The guide wire can be used as a guide for guiding a distal end portion of the insertion part 2 of the treatment tool 1 to a treatment target site. A guide wire having a predetermined wire diameter is used in combination with the treatment tool 1 according to an inner diameter of a blood vessel or the like at the treatment target site.

The first lumen 11a has an inner diameter that allows the guide wire to be smoothly inserted therein.

The second lumen 11b and the third lumen 11c are through-holes used for inserting a linear member different from the above-described guide wire or circulating a liquid chemical required for treatment. In the present embodiment, inner diameters of the second lumen 11b and the third lumen 11c are both smaller than the inner diameter of the first lumen 11a.

For example, a knife wire 10, which will be described below, can be inserted into the second lumen 11b. For example, liquid such as a contrast medium can circulate through the third lumen 11c.

Although the type of the treatment part 4 is not particularly limited, hereinafter, a case in which the treatment part 4 includes the knife wire 10, as illustrated in FIGS. 1 to 3, will be described as an example.

The knife wire 10 is a conductive wire member capable of incising living tissue by applying a high-frequency current to the living tissue.

The knife wire 10 is exposed outside the first sheath 11 at the distal end side insertion part 2A.

Although not illustrated, a distal end portion of the knife wire 10 is locked to an inside of the second lumen 11b of the first sheath 11 (see FIG. 4).

As illustrated in FIG. 2, the knife wire 10 is exposed outside the first sheath 11 through a first side hole 11d communicating with the second lumen (see FIG. 4) and reenters the second lumen 11b from a second side hole 11e provided to communicate with the second lumen 11b at a more proximal end side than the first side hole 11d. The knife wire 10 that entered the second lumen 11b (see FIG. 4) extends further toward the proximal end side in the second lumen 11b. Further, the knife wire 10 extends to the operation part 3, which will be described below, (see FIG. 3) through a lumen formed in the proximal end side insertion part 2B, which will be described below, and is connected to the operation part 3.

A portion of the knife wire 10 exposed outside the first sheath 11 contributes to the incision of living tissue. In the present embodiment, the knife wire 10 can be used, for example, for a treatment in which a duodenal papilla is incised.

In the present embodiment, the first sheath 11 is formed of a flexible insulating material having heat resistance so that the knife wire 10 is inserted therein. In the present embodiment, the first sheath 11 is formed of, for example, polytetrafluoroethylene (PTFE).

As illustrated in FIG. 1, the balloon part 5 includes a balloon 14 and a balloon tube 15 in that order from the distal end side toward the proximal end side at an outer circumferential portion at the proximal end side of the first sheath 11.

As illustrated in FIG. 3, the balloon 14 has a tubular first neck part 14a having an inner diameter fitted over the first sheath 11 at the distal end side. The balloon 14 has a tubular second neck part 14b slightly larger than an outer diameter of the first sheath 11 at the proximal end side. An intermediate portion in the longitudinal direction of the balloon 14 can be expanded to a diameter larger than inner diameters of the first neck part 14a and the second neck part 14b.

FIG. 3 illustrates a state in which the balloon 14 is expanded. FIGS. 1 and 2 illustrate a state in which the balloon 14 is reduced.

The balloon tube 15 is a tubular member having an outer diameter larger than the first sheath 11 and smaller than an outer diameter of the balloon 14 when the balloon 14 is expanded.

As illustrated in FIG. 5, a cylindrical locking part 15a for locking a fixing pipe 17 is formed at a distal end side of the balloon tube 15.

As illustrated in FIGS. 5 and 6, the fixing pipe 17 includes a tubular part 17a into which the first sheath 11 is inserted and a locking part 17b protruding outward in the diametric direction from a distal end portion of the tubular part 17a.

An elongation suppressing wire 16 configured to suppress elongation of the insertion part 2 in the longitudinal direction is fixed to a proximal end portion of the tubular part 17a. The elongation suppressing wire 16 is formed of a metal wire having higher tensile rigidity than of the first sheath 11 and a second sheath 12, which will be described below, (see FIG. 3). For example, a wire formed of a stainless metal material may be adopted as the elongation suppressing wire 16.

As illustrated in FIG. 3, the elongation suppressing wire 16 extends to the operation part 3 through the balloon tube 15 and a lumen formed in the second sheath 12, which will be described below. A method of fixing between the elongation suppressing wire 16 and the operation part 3 will be described below.

As illustrated in FIG. 5, the fixing pipe 17 is arranged such that the locking part 17b faces the distal end side. The first sheath 11 is inserted into the fixing pipe 17. The tubular part 17a of the fixing pipe 17 is fitted in the locking part 15a of the balloon tube 15. The locking part 17b of the fixing pipe 17 is locked to a distal end surface 15d of the locking part 15a of the balloon tube 15.

As will be described below, because the treatment tool 1 receives an external force from a treatment tool channel or the like of an endoscope and tension is generated in the elongation suppressing wire 16 when the treatment tool 1 is operated, the locking part 17b is pulled by the elongation suppressing wire 16 and locked to the distal end surface of the locking part 15a.

The second neck part 14b of the balloon 14 is arranged to be fitted over the locking part 17b of the fixing pipe 17 and the locking part 15a of the balloon tube 15. Also, the second neck part 14b is fixed to be watertight at a first fixing part 15b at an outer circumferential surface of the balloon tube 15 at the proximal end side of the locking part 15a.

For example, the first fixing part 15b may be formed by thermally welding the second neck part 14b to the outer circumferential portion at the proximal end side about several mm from the distal end of the balloon tube 15. In this case, because the locking part 15a is disposed further toward the distal end side than the first fixing part 15b, the locking part 15a is not deformed due to an influence of heating. Because of this, the locking part 15a retains a cylindrical shape even after the first fixing part 15b is formed. In such an assembled state, the balloon 14 and the balloon tube 15 constitute a tubular part connected to be watertight. A distal end of the tubular part is closed by the first neck part 14a fixed to the first sheath 11.

As illustrated in FIG. 3, a second fixing part 15c at a proximal end portion of the balloon tube 15 is fitted over a second end portion E2 of the second sheath 12, which will be described below, and is fixed to the second sheath 12 to be watertight.

A clearance extending along the axial direction of the balloon part 5 is formed between the outer circumferential surface of the first sheath 11 and inner circumferential surfaces of the balloon 14 and the balloon tube 15. The clearance constitutes a liquid-sending space S1 which serves as a flow path of a fluid for expanding the balloon 14.

In the balloon part 5, the elongation suppressing wire 16 extends toward the proximal end side through the liquid-sending space S1.

The balloon 14 is a compliance balloon whose expansion diameter changes according to pressure of a fluid in the balloon 14. In the present embodiment, a correlation between the outer diameter of the balloon 14 and internal pressure of the balloon 14 is nonlinear.

The outer diameter of the balloon 14 has a one-to-one relationship with at least three internal pressures. Hereinafter, an outer diameter value of the balloon 14 with respect to each of the three internal pressures is defined as "compliance." Although not particularly illustrated, a compliance value of the balloon 14 is attached to, for example, the operation part 3 as a display label to be recognized by the operator.

As a material of the balloon 14, for example, polyamide, polyamide elastomer, polyethylene terephthalate (PET) elastomer, polyurethane, or the like may be adopted.

The balloon 14 of the present embodiment manufactured with the above material has a compliance set to, for example, 15 mm/3 ATM, 17 mm/4 ATM, or 18 mm/5 ATM.

For example, the notation "15 mm/3 ATM" means that the outer diameter of the balloon 14 is 15 mm when the internal pressure of the balloon 14 is 3 ATM.

The balloon 14 may also be formed of a very flexible material such as latex although an expansion force thereof is extremely small.

As illustrated in FIG. 3, the proximal end side insertion part 2B includes the second sheath 12 (multi-lumen sheath).

As illustrated in FIG. 7, the second sheath 12 is a multi-lumen sheath through which four lumens, a first lumen 12a (guide wire lumen), a second lumen 12b, a third lumen 12c, and a fourth lumen 12d, pass in the axial direction.

Like the first lumen 11a of the first sheath 11 (see FIG. 4), the first lumen 12a is a through-hole into which a guide wire (not illustrated) configured to guide insertion of the treatment tool 1 into a patient's body is inserted. The first lumen 12a has an inner diameter that allows the guide wire to be smoothly inserted therein.

A slit 12e (first slit) having a clearance of a predetermined width w is formed in a part of the first lumen 12a. The width w of the clearance in the slit 12e of the second sheath 12 is narrower than an outer diameter of the guide wire inserted into the first lumen 12a.

As illustrated in FIG. 3, the slit 12e extends from the vicinity of the second fixing part 15c at a distal end side of the second sheath 12 toward an end portion at a proximal end side thereof.

The inner diameter of the first lumen 12a is almost the same (including the case of being the same) as that of the first lumen 11a of the first sheath 11.

The second lumen 12b and the third lumen 12c illustrated in FIG. 7 are through-holes used for inserting a linear member different from the above-described guide wire or circulating liquid chemical required for treatment. In the present embodiment, inner diameters of the second lumen 12b and the third lumen 12c are almost the same (including the case of being the same) as those of the second lumen 11b and the third lumen 11c of the first sheath 11.

The inner diameters of the second lumen 12b and the third lumen 12c are both smaller than the inner diameter of the first lumen 11a.

For example, the knife wire 10 can be inserted into the second lumen 12b. For example, liquid such as a contrast medium can circulate through the third lumen 12c.

The fourth lumen 12d is a through-hole (balloon lumen) for forming a flow path of a fluid for expanding the balloon 14. Further, in the present embodiment, the elongation suppressing wire 16 is inserted into the fourth lumen 12d.

To shorten a contraction time of the balloon 14, an inner diameter of the fourth lumen 12d should be made as large as possible. In the present embodiment, for example, the inner diameter of the fourth lumen 12d is substantially the same (includes the case of being the same) as the inner diameter of the first lumen 12a.

The first lumen 12a and the fourth lumen 12d are arranged at positions facing each other across a central axis O12 of the second sheath 12. The second lumen 12b and the third lumen 12c are also arranged at positions facing each other across the central axis O12 of the second sheath 12. However, a direction in which the second lumen 12b and the third lumen 12c face each other is a direction orthogonal to a direction in which the first lumen 12a and the fourth lumen 12d face each other.

The second fixing part 15c of the balloon tube 15 is fixed to an outer circumferential surface of the second end portion E2, which is the distal end portion of the second sheath 12, to be watertight.

As illustrated in FIG. 8, the proximal end portion of the first sheath 11 faces the second end portion E2 of the second sheath 12. The second sheath 12 and the first sheath 11 are connected to each other via a connecting tube 13.

The connecting tube 13 includes a first connecting tube 13a, a second connecting tube 13b, and a third connecting tube 13c.

The first connecting tube 13a is connected to the first lumen 11a of the first sheath 11 and the first lumen 12a of the second sheath 12 to be watertight.

The second connecting tube 13b is connected to the second lumen 11b of the first sheath 11 and the second lumen 12b of the second sheath 12 to be watertight.

The third connecting tube 13c is connected to the third lumen 11c of the first sheath 11 and the third lumen 12c of the second sheath 12 to be watertight.

The first lumens 11a and 12a, the second lumens 11b and 12b, and the third lumens 11c and 12c constitute independent communication paths via the connecting tube 13. Because the communication paths do not communicate with the liquid-sending space S1, a fluid in the liquid-sending space Si does not enter each of the communication paths.

The first lumens 11a and 12a communicate with the outer circumferential surroundings of the second sheath 12 by the slit 12e formed in the first lumen 12a.

As illustrated in FIG. 3, the fourth lumen 12d of the second sheath 12 opens into the liquid-sending space Si at the second end portion E2. Because of this, the fourth lumen 12d communicates with the liquid-sending space S1.

The elongation suppressing wire 16 extending from the fourth lumen 12d into the liquid-sending space S1 extends from a first end portion E1, which is the proximal end portion of the second sheath 12, to the operation part 3, which will be described below.

A schematic constitution of the operation part 3 will be described prior to describing a shape of the first end portion E1 of the second sheath 12.

As illustrated in FIG. 2, the operation part 3 is arranged at the proximal end portion of the insertion part 2. The operation part 3 is provided to operate the balloon 14 and the knife wire 10.

The operation part 3 includes an operation part main body 20 (sheath-retaining part), a mouthpiece part 22, a fixture 26, a slider 21, and a plug 25.

The operation part main body 20 has a distal end tubular part 20a (tubular part) at a distal end side and has a slide guide part 20f at a proximal end side. The mouthpiece part 22, a connector 23, and the fixture 26 are arranged at an intermediate portion between the distal end tubular part 20a and the slide guide part 20f in the operation part main body 20.

The distal end tubular part 20a is formed in a tubular shape having a hole portion into which the proximal end portion of the insertion part 2 is inserted. As will be described below, the first end portion E1 of the second sheath 12 is fixed to the hole portion of the distal end tubular part 20a.

The slide guide part 20f slidably retains the slider 21, which will be described below. As illustrated in FIG. 3, a slide hole 20n extending to the hole portion of the distal end tubular part 20a is formed inside the slide guide part 20f.

A discharge port of a pressurizer 120 configured to control an amount of expansion of the balloon 14 can be attached to the mouthpiece part 22 to be watertight. Since the pressurizer 120 is attached to the mouthpiece part 22, a fluid for expanding the balloon 14 can be introduced from the pressurizer 120 to the balloon 14.

The connector 23 is, for example, a luer lock connector. The connector 23 communicates with the third lumen 12c of the second sheath 12 via a flow path (not illustrated). A syringe 126, which will be described below, (see FIG. 30) configured to supply a contrast medium can be attached to the connector 23.

The fixture 26 is a member configured to detachably fix the operation part 3 to the pressurizer 120. The fixture 26 is formed at a side surface of the operation part main body 20. In the present embodiment, the fixture 26 is formed in a C-shape that can be locked to an outer circumference of the pressurizer 120.

The operation part main body 20 and the fixture 26 have rigidity such that, when a force for operating the slider 21, which will be described below, and the pressurizer 120 is applied to the slider 21 and the pressurizer 120, the operation part main body 20 and the fixture 26 are not substantially deformed.

The operation part main body 20 and the fixture 26 may be formed by integrally molding a mold as a synthetic resin or may be formed by combining molded parts of a synthetic resin.

In the present embodiment, the fixture 26 is attachable to and detachable from the pressurizer 120 and is selectively attachable to and detachable from any one of the pressurizer 120 and an endoscope 130, which will be described below. That is, when the pressurizer 120 is not used, the fixture 26 may be used for a purpose of fixing the treatment tool 1 to the endoscope.

In a state in which the fixture 26 is fixed to the pressurizer 120, the fixture 26 is arranged at a position at which display of the compliance of the balloon 14 and display of a pressure of the pressurizer 120 are simultaneously visible.

As illustrated in FIG. 2, the slider 21 is an operation portion configured to advance and retract the knife wire 10 in a direction of a central axis of the knife wire 10. The slider 21 is movably attached to the slide guide part 20f. The slider 21 is formed of an insulating material.

An operation rod 24 configured to connect the slider 21 and a proximal end portion of the knife wire 10 is fixed to the slider 21.

As illustrated in FIG. 3, the operation rod 24 is slidably inserted into the slide hole 20n in the operation part main body 20.

The knife wire 10 extending from the second sheath 12 toward the proximal end side is connected to a distal end portion of the operation rod 24. Because of this, the knife wire 10 inserted into the insertion part 2 can be advanced and retracted at the proximal end side by the operator sliding the slider 21 along the slide guide part 20f. Because of this, the operator can pull the knife wire 10, exposed outside the first sheath 11 in the distal end side insertion part 2A, into an arc shape or loosen the knife wire 10.

The operation rod 24 is formed of a conductor and electrically connects the knife wire 10 and the plug 25, which will be described below.

The plug 25 is a conductor fixed to the slider 21. The plug 25 is fixed to the proximal end portion of the knife wire 10 via the operation rod 24. The plug 25 and the knife wire 10 are electrically conducted via the operation rod 24. The plug 25 can be connected to a high-frequency power supply device 128, which will be described below, (see FIG. 45) configured to supply high-frequency current to the knife wire 10.

A guide wire insertion opening 20b formed in the distal end tubular part 20a is provided to insert the guide wire from the operation part 3 into the insertion part 2. However, the guide wire insertion opening 20b is not provided only for inserting the guide wire. The guide wire insertion opening 20b can also be used as an opening for pulling out the guide wire.

As illustrated in FIGS. 9 and 10, the guide wire insertion opening 20b includes a slit 20c (second slit) and a main opening 20d.

The slit 20c extends along the central axis O20a (see FIG. 10) of the distal end tubular part 20a and passes through a side surface of the distal end tubular part 20a in the diametric direction. In an extending direction, the slit 20c opens to a distal end surface of the distal end tubular part 20a and an inner circumferential portion of the main opening 20d.

As illustrated in FIG. 11, the width W of a clearance of the slit 20c is wider than the slit 12e of the second sheath 12 and wider than an outer diameter of the guide wire 30.

As illustrated in FIG. 10, the main opening 20d is a substantially rectangular opening elongated in a direction along the central axis O20a when viewed from the diametric direction. A main opening distal end surface 20k, which is a wall surface at a distal end side of an inner circumferential surface of the main opening 20d, is formed of a plane orthogonal to the central axis O20a.

An opening width in a short-side direction of the main opening 20d is wider than a clearance width of the slit 20c. The slit 20c opens at a central part of the main opening distal end surface 20k at the distal end side (the left side in the drawing) of the main opening 20d.

A pair of guide parts 20j protruding farther inward than the inner circumferential portion in the short-side direction of the main opening 20d are formed further toward the distal end side than the main opening 20d. The pair of guide parts 20j face each other in a circumferential direction of the distal end tubular part 20a. The slit 20c is formed by end surfaces in the circumferential direction of each of the guide parts 20j.

As illustrated in FIG. 11, when viewed from the axial direction, each of the guide parts 20j are bent in an arc shape along a cylindrical tubular shape of the distal end tubular part 20a. In the distal end tubular part 20a, a shape of a cross-section orthogonal to the axial direction at a more distal end side than the guide wire insertion opening 20b is a C-shape.

An inclined portion 20e is a portion configured to guide an insertion posture of the guide wire 30 (see FIG. 11) so that it is easy for the guide wire 30 to be inserted from the proximal end side toward the distal end side with respect to the main opening 20d.

The inclined portion 20e is formed at the proximal end side of the main opening 20d. The inclined portion 20e is inclined inward from the outer circumferential portion of the distal end tubular part 20a in a direction from the proximal end side toward the distal end side.

As illustrated in FIGS. 9 to 12, the first end portion E1 of the second sheath 12 is inserted into a space defined by an inner circumferential surface 20m (see FIGS. 11 and 12) of the distal end tubular part 20a.

As illustrated in FIGS. 13 and 14, an opening OP is formed in the first end portion E1 of the second sheath 12 by cutting a side portion of the second sheath 12. The inner circumferential surface of the first lumen 12a is exposed to an inside of the opening OP.

When viewed from the diametric direction, the opening OP is surrounded by a pair of exposed surfaces Sf and exposed surfaces Sg and Sh being arranged in a substantially U-shape.

The pair of exposed surfaces Sf extend in a longitudinal direction of the first lumen 12a from an end surface 12k in the axial direction at the proximal end side of the second sheath 12 toward the distal end side. The pair of exposed surfaces Sf extend parallel to each other across the exposed portion of the first lumen 12a.

In the present embodiment, the pair of exposed surfaces Sf are formed of planes at equal distances from the central axis O12.

In the present embodiment, as illustrated in FIG. 11, the pair of exposed surfaces Sf are formed at positions passing through a substantial center (including the center) of the first lumen 12a. A distance from each of the exposed surfaces Sf to the outer circumferential surface of the second sheath 12, which is the outside of the fourth lumen 12d, is a distance h which is longer than a radius of the second sheath 12. In the present embodiment, each of the exposed surfaces Sf extends substantially parallel (including parallel) to the second lumen 12b and the third lumen 12c.

When viewed from the diametric direction, as illustrated in FIG. 14, the exposed surfaces Sg and Sh form a V-shape having a top part on the central axis O12. The exposed surfaces Sg and Sh are planes extending toward the exposed surfaces Sf from the outer circumferential surface of the second sheath 12 in which the slit 12e is formed. In the present embodiment, both of the exposed surfaces Sg and Sh are planes orthogonal to the exposed surfaces Sf. In the present embodiment, when viewed from the diametric direction passing through the center of the slit 12e, the exposed surfaces Sg and Sh, for example, intersect at an angle of about 45° (includes 45°) with respect to the central axis O12.

Each of the exposed surfaces Sf is formed by an axially cut surface 12f. The exposed surfaces Sg and Sh are formed by a first side cut surface 12g and a second side cut surface 12h.

The axially cut surface 12f is a surface formed by passing through substantially the center of the first lumen 12a from the end surface 12k and cutting in a direction substantially parallel to the central axis O12, the second lumen 12b, an the third lumen 12c.

The axially cut surface 12f is formed as two surfaces facing each other when the cutting is performed. However, as will be described below, the axially cut surface 12f facing the exposed surfaces Sf are removed when all of the cutting is completed.

As illustrated in FIG. 14, the first side cut surface 12g and the second side cut surface 12h are cut surfaces intersecting in an X-shape with respect to the second sheath 12 when viewed from the diametric direction, which passes through the center of the slit 12e, and reaching a position on the same plane as the axially cut surface 12f.

When viewed from the diametric direction passing through the center of the slit 12e, the first side cut surface 12g and the second side cut surface 12h intersect in an X-shape at a point P on the central axis O12 disposed slightly further toward the proximal end side than the distal end portion of the axially cut surface 12f.

When viewed from the diametric direction passing through the center of the slit 12e, the first side cut surface 12g and the second side cut surface 12h intersect at an angle of about 45° with respect to the central axis O12.

When cutting is performed, the first side cut surface 12g (the second side cut surface 12h) is formed as two surfaces facing each other. However, as will be described below, the first side cut surface 12g (the second side cut surface 12h) facing the exposed surface Sg (Sh) is removed when all of the cutting is completed.

Because of this, in the present embodiment, the first side cut surface 12g (the second side cut surface 12h) forming the two surfaces facing each other is formed further toward the distal end side in the second sheath 12 than the point P.

The axially cut surface 12f forming the two surfaces facing each other is formed in an area ranging from a position at which the axially cut surface 12f intersects the exposed surfaces Sg and Sh to a distal end portion in a cutting direction of the axially cut surface 12f.

When cutting is performed by a cutter, a cutting edge of the cutter often performs movement in which movement parallel to the cutting edge and movement perpendicular to the cutting edge are combined. The "cutting direction" in the present specification refers to a direction orthogonal to a cutting edge among movement directions of the cutting edge when cutting is performed.

In this way, since the distal end portion of the axially cut surface 12f is disposed further toward the distal end side than an intersecting position thereof with the exposed surface Sg, a triangular piece-like part 12j (first piece-like part) having the exposed surface Sg and the axially cut surface 12f at an outer edge thereof is formed. Likewise, since the distal end portion of the axially cut surface 12f is disposed further toward the distal end side than an intersecting position thereof with the exposed surface Sh, a triangular piece-like part 12i (second piece-like part) having the exposed surface Sh and the axially cut surface 12f at an outer edge thereof is formed.

The first end portion E1 of the second sheath 12 having the above constitution is inserted into the distal end tubular part 20a so that the slit 12e is disposed at the center of the slit 20c when viewed from the diametric direction, as illustrated in FIG. 10. A position of the first end portion E1 in the axial direction is a position at which the first side cut surface 12g and the second side cut surface 12h are closer to the distal end side than the main opening distal end surface 20k (see FIGS. 10 and 12) and at which the end surface 12k of the second sheath 12 is further toward the proximal end side than the inclined portion 20e (see FIG. 10).

As illustrated in FIG. 15, the second sheath 12 is fixed to the operation part main body 20 via a fixing member 19.

The fixing member 19 is a tubular member having a distal end portion fitted in the fourth lumen 12d and a proximal end portion locked to the operation part main body 20. An inner diameter of a through-hole 19a passing through the fixing member 19 in the axial direction is larger than the outer diameter of the elongation suppressing wire 16.

An engaging protrusion 19b biting into an inner circumferential surface of the fourth lumen 12d is formed at an outer circumferential surface of the distal end portion of the fixing member 19. The engaging protrusion 19b protrudes outward in the diametric direction from the outer circumferential surface of the fixing member 19.

A cylindrical proximal end side tubular part 19d is formed at the proximal end portion of the fixing member 19.

In the second sheath 12, a locking part 19c configured to lock the end surface 12k at the outer circumferential side of the fourth lumen 12d in the axial direction is formed at an intermediate portion of the fixing member 19 in the axial direction. The locking part 19c protrudes outward in the diametric direction from the outer circumferential surface of the fixing member 19.

The distal end portion of the fixing member 19 is inserted into the proximal end side of the fourth lumen 12d, and the fixing member 19 is connected to the second sheath 12 by being pushed until the end surface 12k comes into contact with the locking part 19c. An outer diameter of the fixing member 19 is a slightly larger diameter than the fourth lumen 12d. The locking part 19c and the end surface 12k are adhered to each other. Because of this, the fixing member 19 is mounted to be watertight on the fourth lumen 12d.

A locking hole portion 20i is provided at a distal end portion of a liquid-sending duct 20g (a left end portion of the liquid-sending duct 20g in FIG. 15) communicating with the mouthpiece part 22. The proximal end side tubular part 19d of the fixing member 19 is fitted in the locking hole portion 20i to be watertight. An inner diameter of the locking hole portion 20i is larger than the inner diameter of the liquid-sending duct 20g. Because of this, at the proximal end side of the locking hole portion 20i, a step is formed between the locking hole portion 20i and the liquid-sending duct 20g. The step restricts movement of the fixing member 19 so that an end surface 19e of the proximal end side tubular part 19d of the fixing member 19 does not move over the step toward the proximal end side in the axial direction.

In this way, because the fourth lumen 12d communicates with the inside of the liquid-sending duct 20g and the mouthpiece part 22, a fluid can be introduced into the liquid-sending space S1 or the fluid in the liquid-sending space S1 can be discharged through the mouthpiece part 22.

The elongation suppressing wire 16 inserted into the fourth lumen 12d extends into the liquid-sending duct 20g through the through-hole 19a of the fixing member 19.

A through-hole 20h into which the elongation suppressing wire 16 is inserted is formed in the liquid-sending duct 20g. The proximal end portion of the elongation suppressing wire 16 is inserted into the through-hole 20h. The proximal end portion of the elongation suppressing wire 16 is fixed to a wall surface through which the through-hole 20h passes via a fixing part 18.

The fixing part 18 fixes a position of the elongation suppressing wire 16 and seals the through-hole 20h to be watertight.

As illustrated in FIG. 3, in the treatment tool 1, the distal end portion of the elongation suppressing wire 16 is fixed to the fixing pipe 17, and the proximal end portion of the elongation suppressing wire 16 is fixed to the operation part main body 20. Because of this, the elongation suppressing wire 16 is arranged in parallel with the first sheath 11 and the second sheath 12 in a communicating space of the liquid-sending space S1 and the fourth lumen 12d. Because the elongation suppressing wire 16 is formed of a metal wire, tensile rigidity thereof is higher than the first sheath 11 and the second sheath 12. Because of this, when the insertion part 2 is pulled in a range in which the elongation suppressing wire 16 is parallel thereto, elongation of the insertion part 2 in the axial direction is suppressed by the tensile rigidity of the elongation suppressing wire 16.

Next, a method for manufacturing the treatment tool 1 will be described mainly with reference to a method for manufacturing the second sheath 12.

Figure 16:
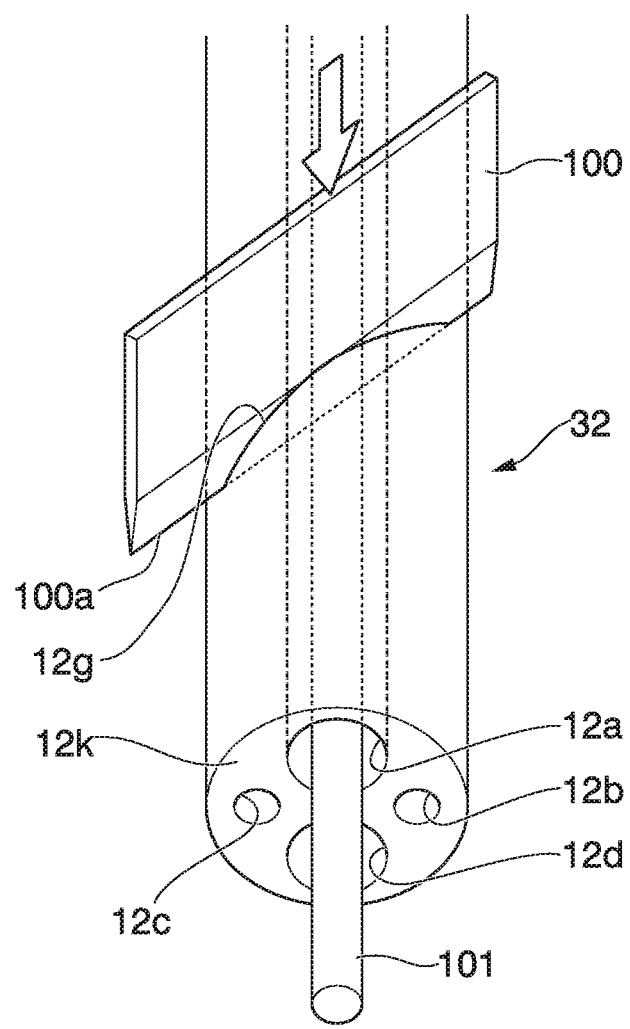
FIG. 16 is a perspective process explanatory view of a process for manufacturing the treatment tool for an endoscope according to the first embodiment of the present invention.
Figure 17:
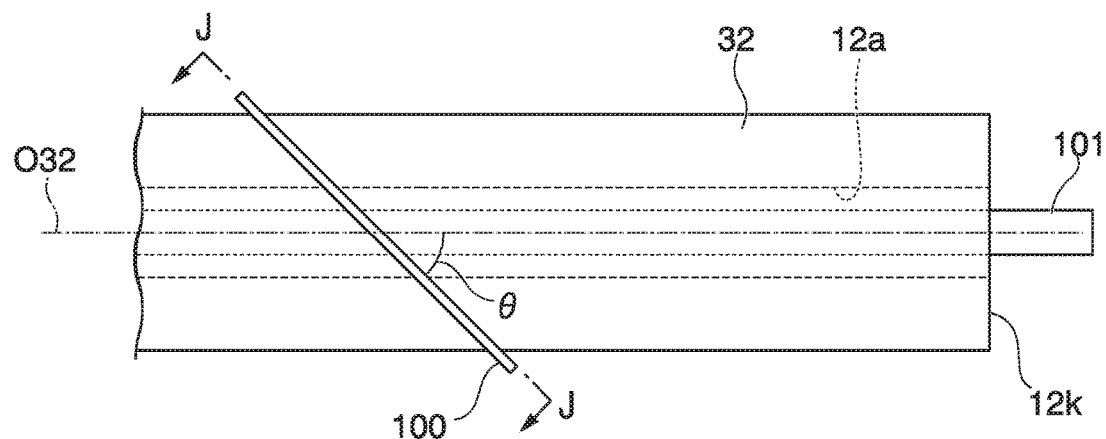
FIG. 17 is a plan process explanatory plan view of the process for manufacturing the treatment tool for an endoscope according to the first embodiment of the present invention.
Figure 18:
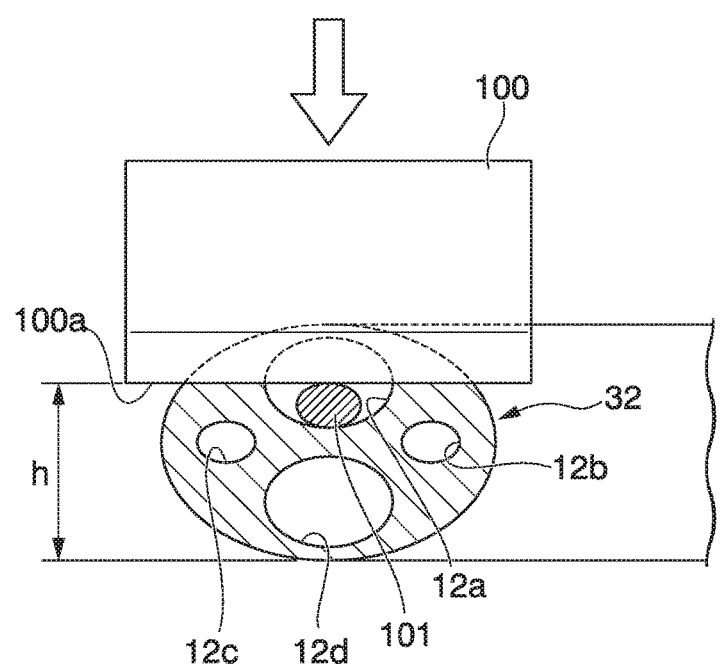
FIG. 18 is a cross-sectional view taken along line J-J in FIG. 17.
Figure 19:
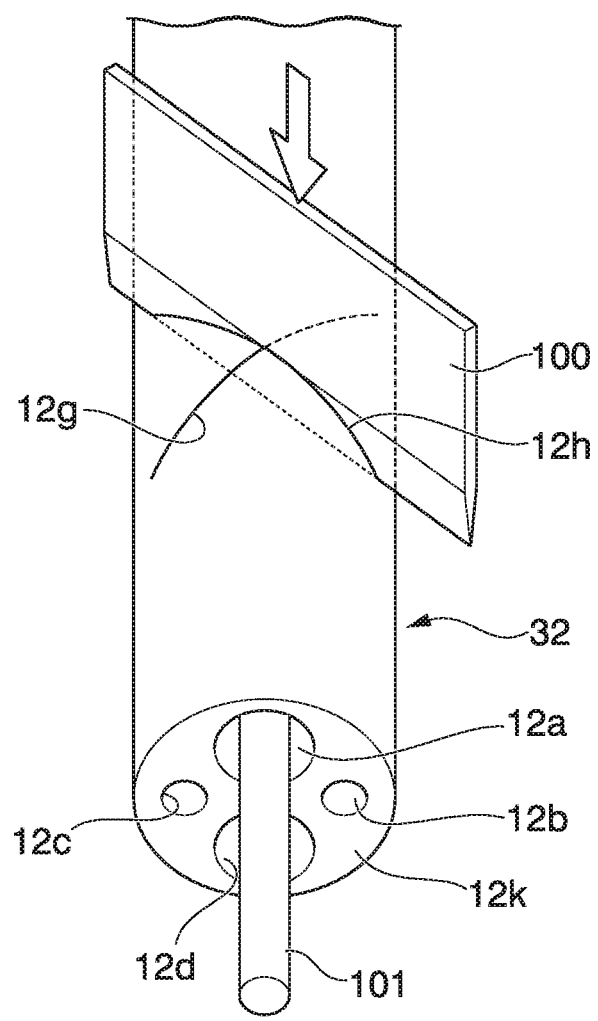
FIG. 19 is a perspective process explanatory view of the process for manufacturing the treatment tool for an endoscope according to the first embodiment of the present invention.
Figure 20:
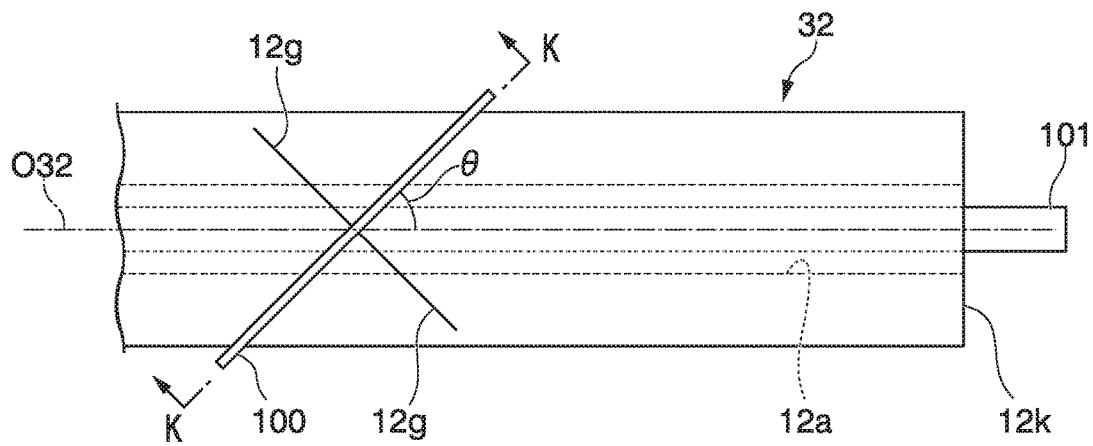
FIG. 20 is a plan process explanatory view of the process for manufacturing the treatment tool for an endoscope according to the first embodiment of the present invention.
Figure 21:
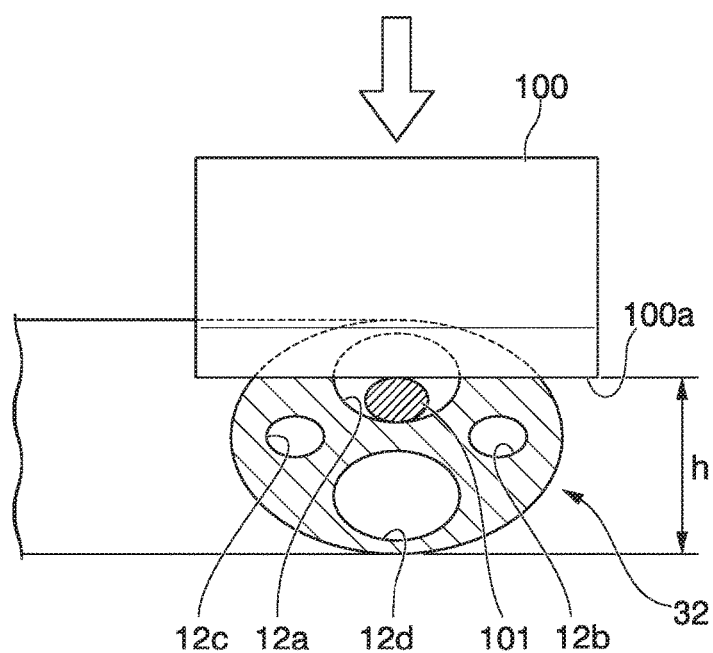
FIG. 21 is a cross-sectional view taken along line K-K in FIG. 20.
Figure 22:
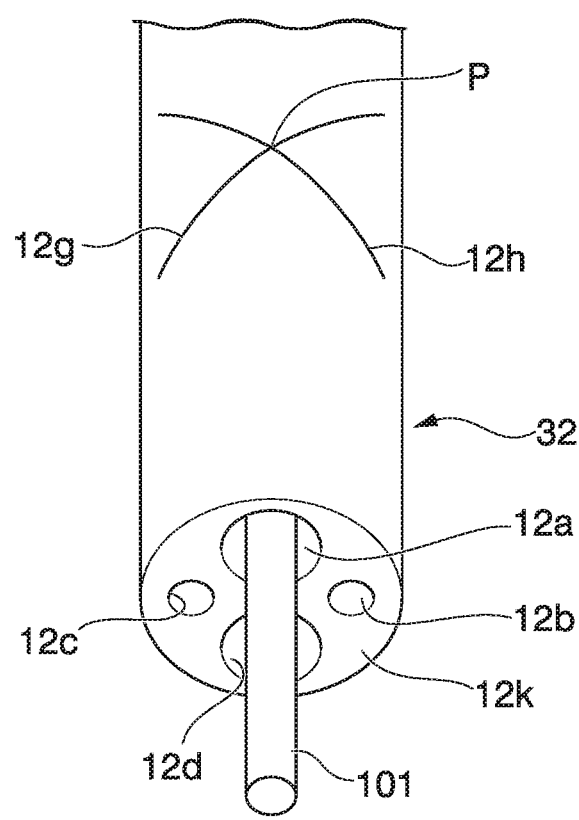
FIG. 22 is a perspective process explanatory view of the process for manufacturing the treatment tool for an endoscope according to the first embodiment of the present invention.
Figure 23:
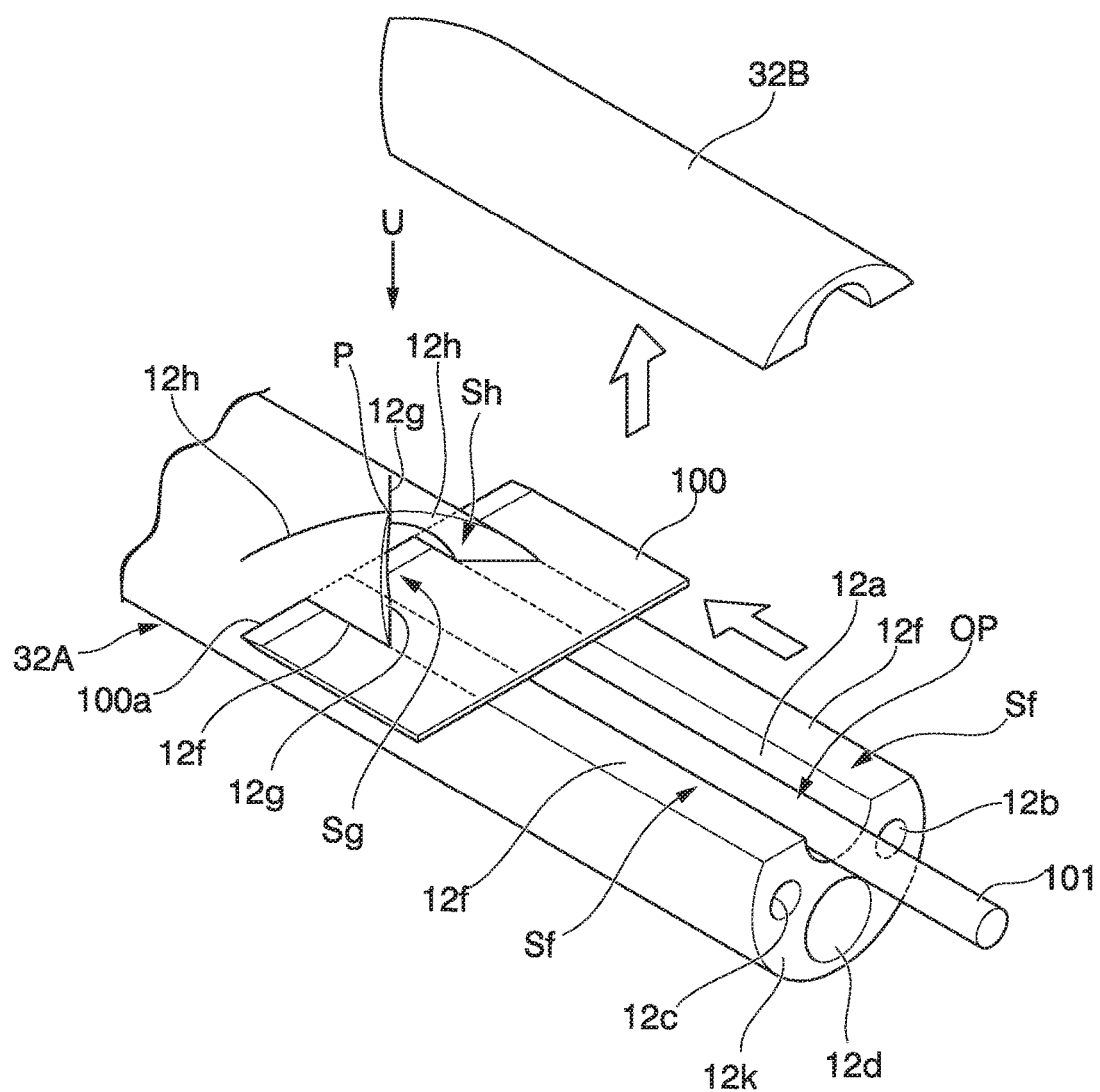
FIG. 23 is a perspective process explanatory view of the process for manufacturing the treatment tool for an endoscope according to the first embodiment of the present invention.
Figure 24:
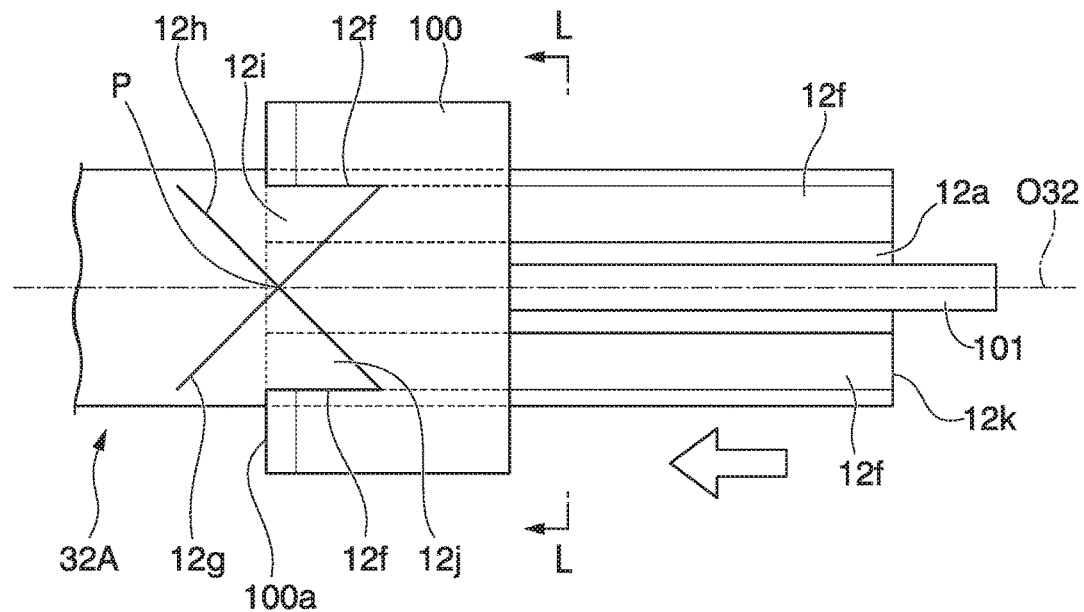
FIG. 24 is a plan view viewed from a direction of U in FIG. 23.
Figure 25:
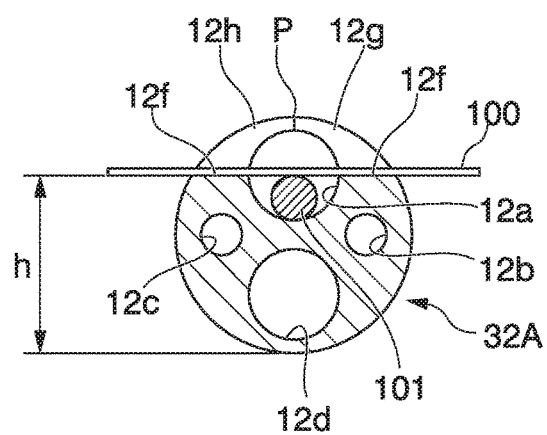
FIG. 25 is a cross-sectional view taken along line L-L in FIG. 24.

FIG. 16 is a perspective process explanatory view of a process for manufacturing the treatment tool for an endoscope according to the first embodiment of the present invention. FIG. 17 is a plan process explanatory plan view of the process for manufacturing the treatment tool for an endoscope according to the first embodiment of the present invention. FIG. 18 is a cross-sectional view taken along line J-J in FIG. 17. FIG. 19 is a perspective process explanatory view of the process for manufacturing the treatment tool for an endoscope according to the first embodiment of the present invention. FIG. 20 is a plan process explanatory view of the process for manufacturing the treatment tool for an endoscope according to the first embodiment of the present invention. FIG. 21 is a cross-sectional view taken along line K-K in FIG. 20. FIG. 22 is a perspective process explanatory view of the process for manufacturing the treatment tool for an endoscope according to the first embodiment of the present invention. FIG. 23 is a perspective process explanatory view of the process for manufacturing the treatment tool for an endoscope according to the first embodiment of the present invention. FIG. 24 is a plan view viewed from a direction of U in FIG. 23. FIG. 25 is a cross-sectional view taken along line L-L in FIG. 24.

As illustrated in FIG. 16, when manufacturing the second sheath 12, first, a multi-lumen tube 32 in which the first lumen 12a, the second lumen 12b, the third lumen 12c, and the fourth lumen 12d are formed is manufactured.

Then, a process for forming the first side cut surface 12g, the second side cut surface 12h, and the axially cut surface 12f at an end portion of the multi-lumen tube 32, which becomes the first end portion E1 in the second sheath 12, is performed.

First, as illustrated in FIG. 16, the multi-lumen tube 32 is horizontally arranged so that the first lumen 12a is on an upper side thereof and the fourth lumen 12d is on a lower side, and a core metal 101 is inserted into the first lumen 12a.

The core metal 101 comes into contact with the lowermost inner circumferential surface of the first lumen 12a due to its own weight. The core metal 101 is inserted to a position more inward than the position at which the first side cut surface 12g and the second side cut surface 12h intersect.

The core metal 101 is a member configured to regulate a cutting amount of a cutter 100 configured to form the first side cut surface 12g and the second side cut surface 12h.

First, to form the first side cut surface 12g, cutting in a cutting direction from the outer circumferential side facing the first lumen 12a toward the multi-lumen tube 32 is performed by the cutter 100.

A posture of the cutter 100 is a posture in which a cutting edge 100a is horizontally arranged and the cutting direction is along a vertical direction. Further, the posture of the cutter 100 in a plan view with respect to the multi-lumen tube 32 is inclined by an angle θ with respect to a central axis O32 of the multi-lumen tube 32, as illustrated in FIG. 17. The angle θ is equal to an angle of inclination between the first side cut surface 12g and the central axis O12 in the second sheath 12. In the present embodiment, the angle θ is about 45°.

When such a cutting operation is performed, as illustrated in FIG. 18, the cutter 100 causes a cut in a part of the multi-lumen tube 32 and forms the first side cut surface 12g. However, when the cutting edge 100a of the cutter 100 comes into contact with the core metal 101, the cutting cannot be performed further. Because of this, the first side cut surface 12g stops at a position of the cutting edge 100a.

By appropriately setting an outer diameter of the core metal 101, the cutting edge 100a may be placed on a horizontal plane where a distance from the outer circumferential surface becomes h at a side opposite the first lumen 12a.

In this state, the cutting edge 100a is at a position equally distant from the centers of the second lumen 12b and the third lumen 12c.

When the cutting edge 100a comes into contact with the core metal 101, the cutter 100 is pulled out.

Then, as illustrated in FIGS. 19 and 20, the cutter 100 is rotated around a vertical axis to cut into the multi-lumen tube 32 in a posture inclined by the angle θ at a side of the multi-lumen tube 32 opposite the central axis O32 (see FIG. 20). The cutter 100 cuts into a position intersecting the center of the first side cut surface 12g.

As illustrated in FIG. 21, the cutter 100 cuts until the cutting edge 100a comes into contact with the core metal 101 as described above. When the cutting edge 100a comes into contact with the core metal 101, the cutter 100 is pulled out.

As a result, the second side cut surface 12h is formed.

In this way, as illustrated in FIG. 22, at a side surface of the multi-lumen tube 32, the first side cut surface 12g and the second side cut surface 12h intersecting in an X-shape at the point P when viewed from the diametric direction are formed.

In the present embodiment, the first side cut surface 12g and the second side cut surface 12h pass through an upper half of the first lumen 12a.

Then, the axially cut surface 12f is formed.

The cutter 100 is arranged at an upper portion of the core metal 101 extending from the multi-lumen tube 32. Then, as illustrated in FIGS. 23 and 24, the cutter 100 performs cutting in a cutting direction which is a direction from the end surface 12k along the central axis of the multi-lumen tube 32.

The cutting edge 100a of the cutter 100 retains a posture orthogonal to the central axis O32 of the multi-lumen tube 32 (see FIG. 23).

Further, the cutter 100 comes into contact with the core metal 101 from above and horizontally moves with the core metal 101 as a guide. By the cutting operation of the cutter 100, the axially cut surface 12f is formed from the end surface 12k along the horizontal plane parallel to the central axis O32.

An end portion of the multi-lumen tube 32 is divided into two with the axially cut surface 12f as a boundary therebetween due to the cutting operation. The two divided parts are connected to each other at a distal end side of the cutting edge 100a as long as the two divided parts do not intersect any of the first side cut surface 12g and the second side cut surface 12h.

However, when the cutting edge 100a passes through the first side cut surface 12g and the second side cut surface 12h, which are closest to the end surface 12k, the axially cut surface 12f intersects lower end portions of the first side cut surface 12g and the second side cut surface 12h.

Because of this, a cutout portion 32B above the cutter 100 is spaced apart from a tube main body portion 32A.

When the cutter 100 is moved further toward the distal end side to the position at which the first side cut surface 12g and the second side cut surface 12h intersect, the cutout portion is further increased. However, in the present embodiment, the cutting operation is stopped to prevent this when the cutting edge 100a of the cutter 100 moves slightly further than the point P toward the distal end side when viewed from the diametric direction.

As illustrated in FIG. 24, the piece-like parts 12j and 12i are formed in a range in which the first side cut surface 12g and the second side cut surface 12h overlap the axially cut surface 12f when viewed from the diametric direction.

Then, the cutter 100 and the core metal 101 are removed.

As illustrated in FIGS. 23 and 24, when the cutout portion 32B is removed, the tube main body portion 32A, of which the side portion is cut out, remains in the multi-lumen tube 32. Since the cutout portion 32B is removed, the first side cut surface 12g and the second side cut surface 12h closer to the end surface 12k than the point P are exposed. As a result, the exposed surfaces Sg and Sh are formed in the tube main body portion 32A.

Further, the axially cut surface 12f between the exposed surfaces Sg and Sh and the end surface 12k is exposed, and the exposed surface Sf is formed in the tube main body portion 32A therefrom.

The first lumen 12a is exposed in an area surrounded by the exposed surfaces Sg, Sh, and Sf arranged in a substantially U-shape when viewed from the diametric direction. As a result, the opening OP is formed in the tube main body portion 32A.

In this way, since the first side cut surface 12g, the second side cut surface 12h, and the axially cut surface 12f are formed, the tube main body portion 32A of which the side portion is cut out is formed.

Then, the slit 12e is processed along the central axis O32 from the point P of the tube main body portion 32A, which is a portion at which the first side cut surface 12g and the second side cut surface 12h intersect. A method of processing the slit 12e is not particularly limited. For example, the slit 12e may be processed using a cutter having two cutting edges spaced apart by a clearance width of the slit 12e.

In this way, when the slit 12e is formed through an entire length of the tube main body portion 32A, the second sheath 12 is formed.

At the second end portion E2, the second sheath 12 is connected to the first sheath 11 via the connecting tube 13. Also, the knife wire 10 is inserted into the second sheath 12.

Also, the fixing pipe 17 is inserted into the first sheath 11, and the elongation suppressing wire 16 of the fixing pipe 17 is inserted into the fourth lumen 12d of the second sheath 12.

Further, the balloon 14 and the balloon tube 15 are fixed to the first sheath 11 and the second sheath 12 by inserting the second end portion E2 of the first sheath 11 and the second sheath 12 into the balloon 14 and the balloon tube 15.

At the first end portion E1 of the second sheath 12, the fixing member 19 is fitted to the fourth lumen 12d, and the first end portion E1 of the second sheath 12 is inserted into the distal end tubular part 20a together with the fixing member 19. The second sheath 12 is retained by the operation part main body 20, which is a sheath-retaining part.

The opening OP of the second sheath 12 is aligned with the guide wire insertion opening 20b of the second sheath 12, and the elongation suppressing wire 16 extending from the fixing member 19 is fixed to the operation part main body 20.

The knife wire 10 extending from the first lumen 12a is fixed to the operation rod 24.

In this way, the treatment tool 1 is manufactured.

Next, an action of the treatment tool 1 will be described mainly with reference to an action thereof in the insertion operation of the guide wire 30.

Figure 26:
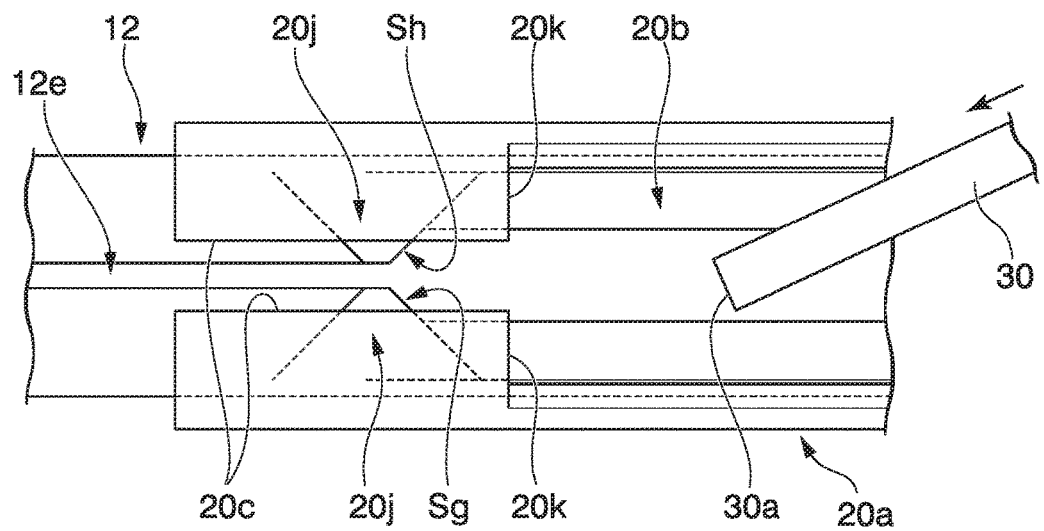
FIG. 26 is a plan explanatory view of operation of the treatment tool for an endoscope according to the first embodiment of the present invention.
Figure 27:
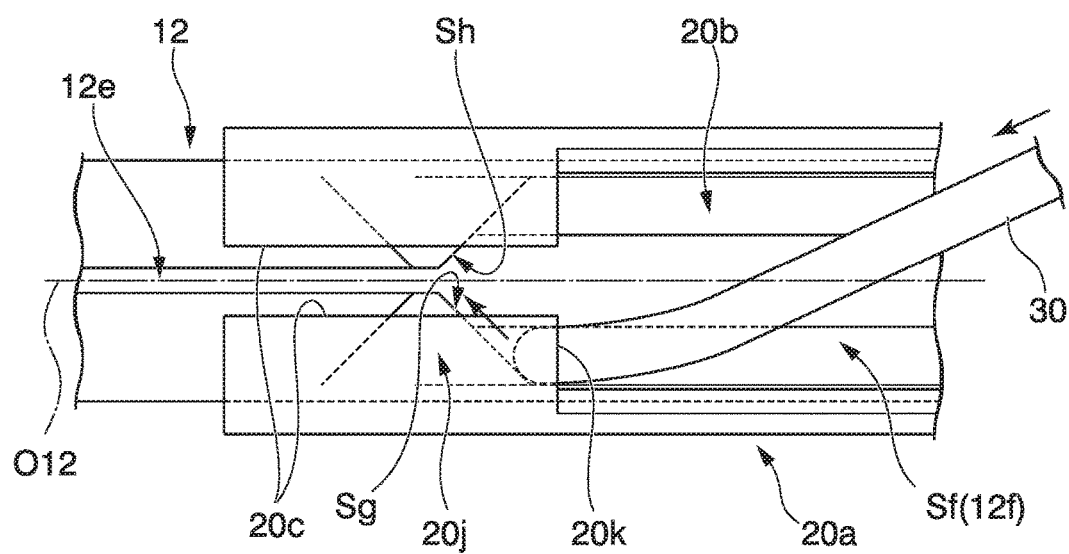
FIG. 27 is a plan explanatory view of operation of the treatment tool for an endoscope according to the first embodiment of the present invention.
Figure 28:
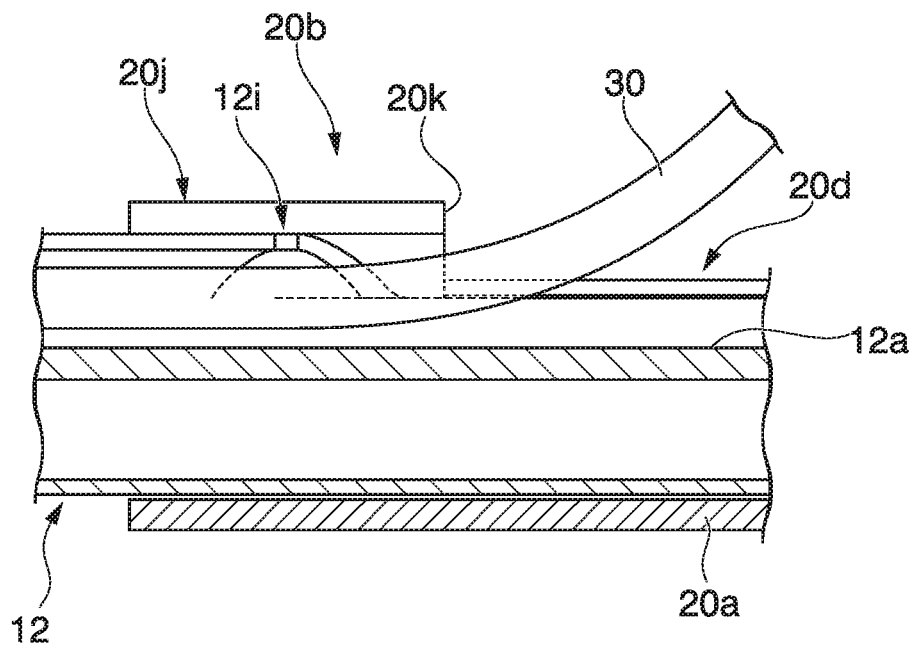
FIG. 28 is a cross-sectional view for describing an action of the treatment tool for an endoscope according to the first embodiment of the present invention.
Figure 29:
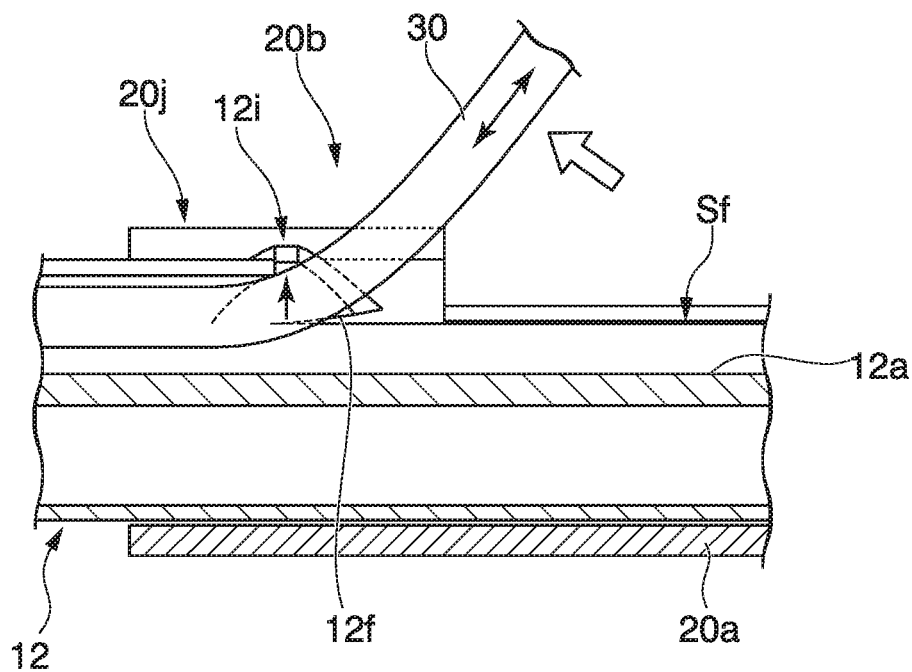
FIG. 29 is a cross-sectional view for describing the action of the treatment tool for an endoscope according to the first embodiment of the present invention.

FIGS. 26 and 27 are plan explanatory views of operation of the treatment tool for an endoscope according to the first embodiment of the present invention. FIGS. 28 and 29 are cross-sectional views for describing an action of the treatment tool for an endoscope according to the first embodiment of the present invention.

The guide wire 30 needs to be inserted into the first lumen 12a to insert the treatment tool 1 along the guide wire 30 into a patient's body.

As illustrated in FIG. 26, in the treatment tool 1, the guide wire 30 can be inserted into the guide wire insertion opening 20b of the operation part 3.

The operator inserts the distal end of the guide wire 30 into the guide wire insertion opening 20b along the inclined portion 20e (not illustrated) of the operation part 3.

As illustrated in FIG. 27, when the operator inserts the distal end portion of the guide wire 30 between the exposed surface Sf seen from the guide wire insertion opening 20b and the guide part 20j of the distal end tubular part 20a, the guide wire 30 can be smoothly inserted.

When the guide wire 30 is inserted between the exposed surface Sf and the guide part 20j, the guide part 20j prevents the guide wire 30 from deviating outward in the diametric direction.

When the operator pushes the guide wire 30, a distal end 30a of the guide wire 30 comes into contact with the exposed surface Sg or the exposed surface Sh. FIG. 27 illustrates an example of a case in which the distal end 30a comes into contact with the exposed surface Sg.

In the present embodiment, because the second sheath 12 has four lumens, as illustrated in FIG. 11, the exposed surface Sg has a portion wider than the outer diameter of the guide wire 30 when viewed from the axial direction, and there is a positional relationship in which most of the distal end 30a of the guide wire 30 overlap the exposed surface Sg.

However, as illustrated in FIG. 27, the exposed surface Sg is inclined with respect to the central axis O12 when viewed from the diametric direction. Because of this, since the distal end 30a of the guide wire 30 does not entirely come into contact with the exposed surface Sg, a large frictional force that prevents movement of the guide wire 30 does not act thereon. Further, because the exposed surface Sg is inclined at a slant with respect to an insertion direction of the guide wire 30, the distal end 30a of the guide wire 30 can smoothly move in a direction approaching the central axis O12 along the inclination of the exposed surface Sg when viewed from the diametric direction.

When the distal end 30a of the guide wire 30 moves in the direction approaching the central axis O12 when viewed from the diametric direction, the distal end 30a moves into the first lumen 12a as indicated by the two-dot chain line in FIG. 11. As a result, the guide wire 30 is inserted into the first lumen 12a.

Because the guide wire 30 has an outer diameter larger than the clearance width w of the slit 12e, when the distal end portion of the guide wire 30 enters the first lumen 12a, the guide wire 30 is inserted toward the distal end side without deviating from the inside of the first lumen 12a.

Conversely, for example, when the exposed surfaces Sg and Sh are in a positional relationship orthogonal to the central axis O12, the problems described above in [Technical Problem] occur. For example, in the above-described treatment tool 241, because the distal end portion 230a of the guide wire 230 may be easily caught by the side cut surface 242g and become unable to advance, workability of the operation of inserting the guide wire 230 is deteriorated.

In this way, according to the treatment tool 1, even when the guide wire 30 is deviated from the guide wire lumen at a time of inserting the guide wire 30, the guide wire 30 moves along the first side cut surface 12g and the second side cut surface 12h which intersect in an X-shape. Because of this, according to the treatment tool 1, the guide wire can be easily inserted into the guide wire lumen when the treatment tool 1 includes a multi-lumen sheath.

Also, in the treatment tool 1, because the axially cut surface 12f is formed by the first side cut surface 12g and the second side cut surface 12h being intersected, the piece-like parts 12j and 12i are formed. The first side cut surface 12g and the second side cut surface 12h at an outer edge of each of the piece-like parts 12j and 12i face the axially cut surface 12f continuous with the exposed surface Sf.

For example, in some cases, after the guide wire 30 is inserted without coming into contact with the piece-like part 12i, as illustrated in FIG. 28, an external force acts on the guide wire 30, as illustrated in FIG. 29, and the guide wire 30 is pulled outward in the diametric direction.

In this case, when the guide wire 30 is pulled outward and the piece-like part 12i receives an external force outward in the diametric direction, the first side cut surface 12g at the outer edge of the piece-like part 12i moves in a direction receding from the axially cut surface 12f continuous with the exposed surface Sf.

Because of this, since a reaction force acting on the guide wire 30 from the piece-like part 12i is reduced, a load at the time of inserting the guide wire 30 is reduced.

Even in this respect, the workability of the operation of inserting the guide wire 30 is improved.

An action of the piece-like part 12i is similar when the guide wire 30 is withdrawn toward the proximal end side.

Although a description thereof is omitted, the piece-like part 12j performs exactly the same action as the piece-like part 12i.

The piece-like parts 12i and 12j are not only deformed in the direction receding from the axially cut surface 12f continuous with the exposed surface Sf, but are also deformable by being moved in a direction along the axially cut surface 12f. Because of this, even when the piece-like parts 12i and 12j receive an external force from the guide wire 30 in the direction along the axially cut surface 12f, the reaction force acting on the guide wire 30 is reduced.

Also, in the treatment tool 1, because the first lumen 12a is formed of a resin material, the slit 12e is deformed when a force is applied to the guide wire 30 inserted therein. Because of this, the guide wire 30 can be retracted to the outside through the slit 12e. For example, when the guide wire 30 extending outward from the guide wire insertion opening 20b is moved toward the slit 20c, the guide wire 30 moves toward the opening of the slit 12e along the V-shaped portion formed by the exposed surfaces Sg and Sh.

When the operator applies force to retract the guide wire 30 outward in the diametric direction and toward the distal end side, the guide wire 30 enters between the slit 12e and the slit 20c. Since the clearance width W of the slit 20c is larger than the outer diameter of the guide wire 30, the guide wire 30 does not come into contact with the slit 20c having high rigidity.

Meanwhile, because the slit 12e has low rigidity, when the guide wire 30 is inserted therein, the clearance width thereof increases, and the guide wire 30 can be withdrawn to the outside of the first lumen 12a.

In this way, the operator can extend the guide wire 30 to the outside of the first lumen 12a from any position at which the slit 12e is provided in the longitudinal direction of the treatment tool 1.

Further, the guide wire 30 extending outward from the slit 12e is returned into the first lumen 12a when pushed inward in the diametric direction by the operator.

Because of this, for example, when the treatment tool 1 is outside a body or at a shallow position inside the body, the guide wire 30 can be extended from the slit 12e at the distal end side of the treatment tool 1. In this case, because an operator located in the vicinity of a patient can perform the insertion of the guide wire 30 by hand, the operability of the guide wire 30 is improved.

When the operator moves the treatment tool 1 further into the body, the operator returns the guide wire 30 to the first lumen 12a by sequentially pushing the guide wire 30 back into the slit 12e.

Next, a method of using the treatment tool 1 according to the present embodiment will be described.

FIGS. 30 to 52 are schematic view illustrating one process during use of the treatment tool for an endoscope according to the first embodiment of the present invention.

Hereinafter, a method of using the treatment tool 1 will be described on the basis of an example in which the treatment tool 1 is used to perform a series of treatments including retrograde cholangiography, an incision of a duodenal papilla PV, and dilation of the duodenal papilla PV, and enable stones to be removed.

Figure 30:
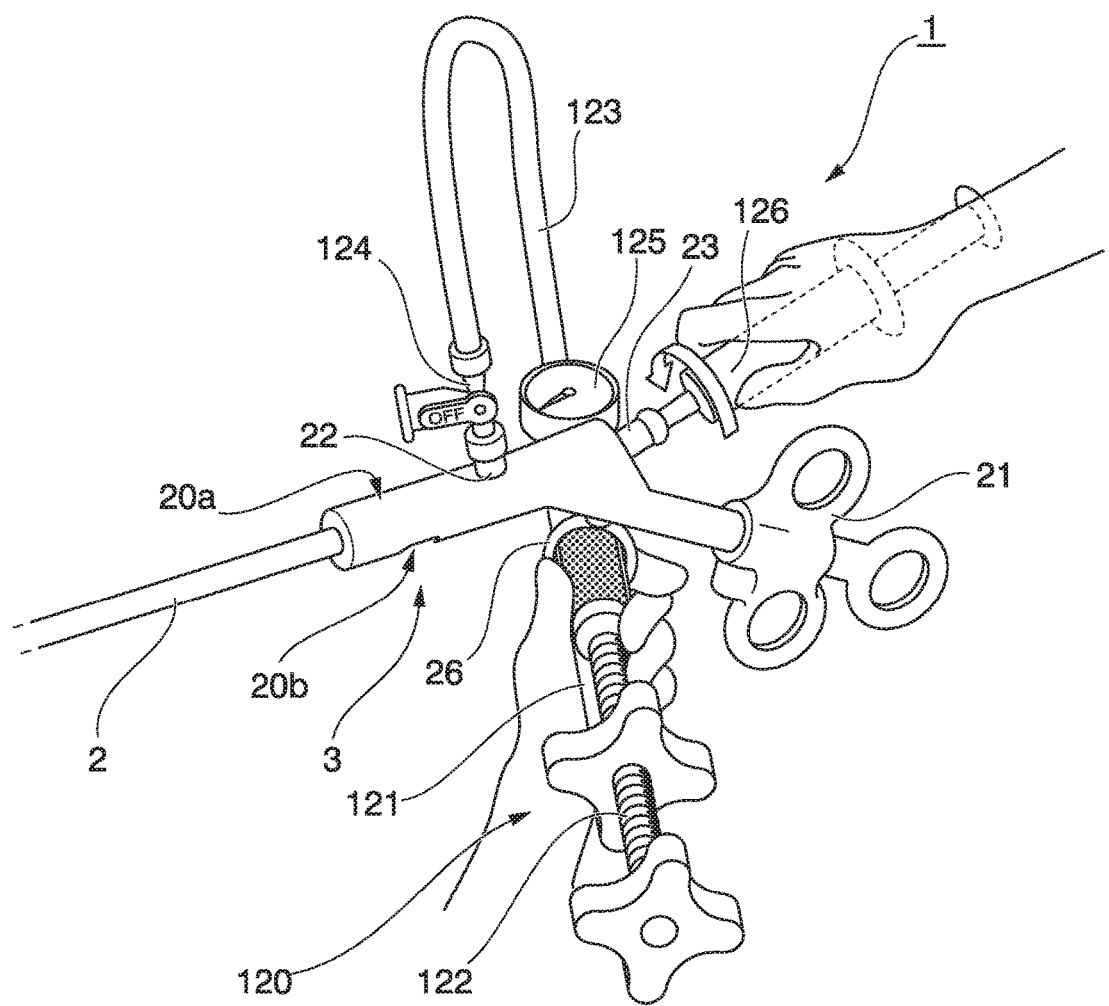
FIG. 30 is a schematic view illustrating one process during use of the treatment tool for an endoscope according to the first embodiment of the present invention.

First, as illustrated in FIG. 30, after preparing for air bleeding or the like of the balloon 14, the treatment tool 1 and the pressurizer 120 are connected to the mouthpiece part 22 via a connecting tube 123. The pressurizer 120 contains a dilation liquid composed of a mixture of a contrast medium and a physiological saline solution.

Then, the syringe 126 for injecting a contrast medium is attached to the connector 23. The syringe 126 for injecting a contrast medium is filled with the contrast medium. The syringe 126 and the connector 23 are connected to be watertight, and the contrast medium can be discharged from the distal end of the insertion part 2 through the third lumen 12c and the third lumen 11c by extruding the contrast medium from the syringe 126.

A cylinder 121 of the pressurizer 120 has an outer circumferential portion retained by the fixture 26 of the treatment tool 1 and a fixed positional relationship with the treatment tool 1.

Figure 31:
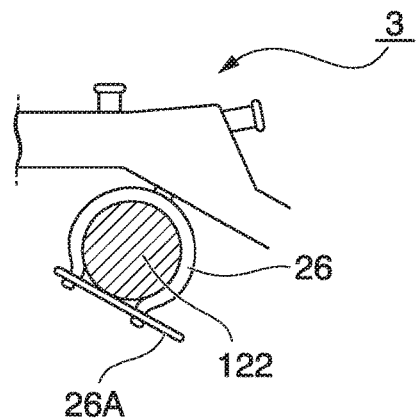
FIG. 31 is a schematic view illustrating one process during use of the treatment tool for an endoscope.

To further increase a fixing force due to the fixture 26, as illustrated in FIG. 31, both ends of the fixture 26 may be fastened by an elastic band 26A.

Figure 32:
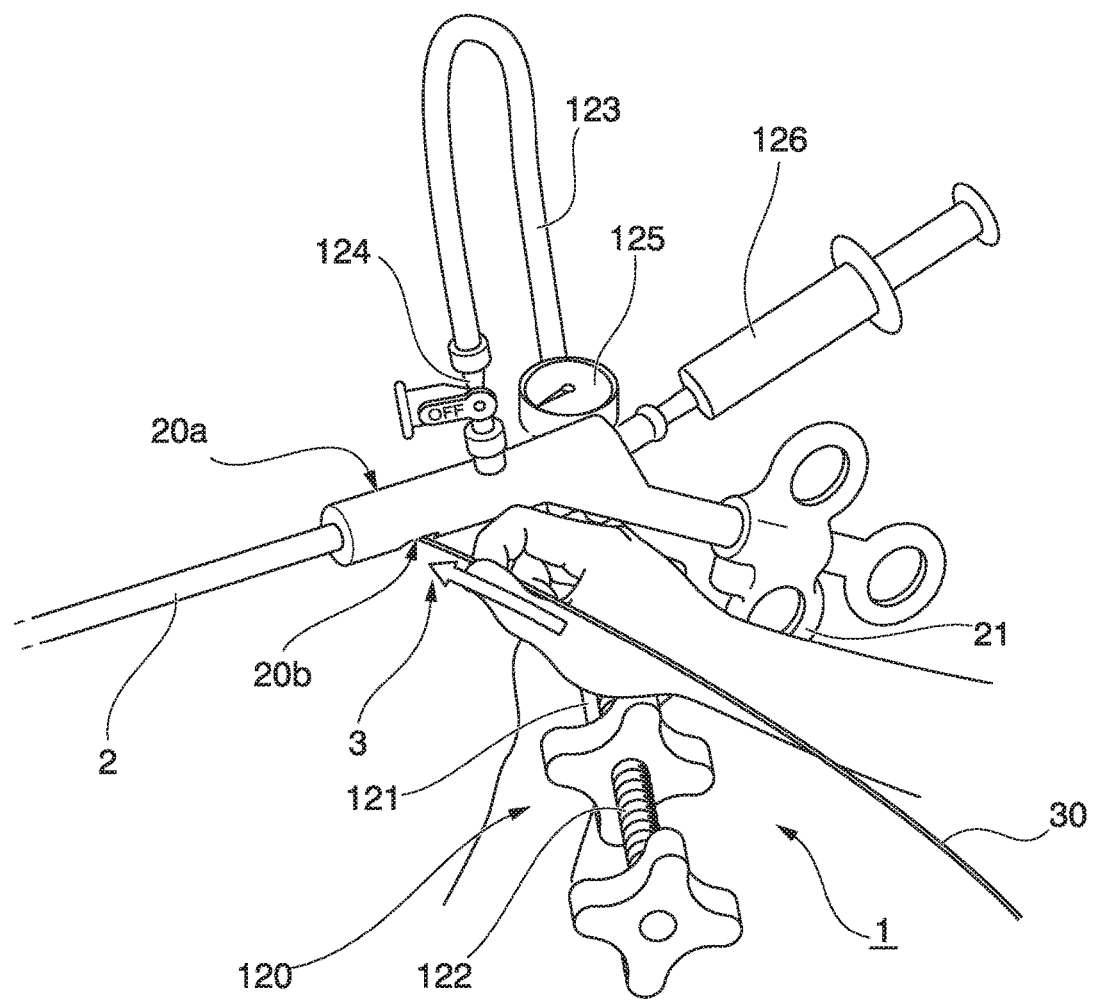
FIG. 32 is a schematic view illustrating one process during use of the treatment tool for an endoscope.

Then, the guide wire 30 configured to guide the distal end of the treatment tool 1 to a treatment target site is prepared. As illustrated in FIG. 32, the guide wire 30 is inserted into the proximal end portion of the insertion part 2 via the guide wire insertion opening 20b of the operation part 3.

The insertion operation of the guide wire 30 and the action of the second sheath 12 during the insertion are the same as the above descriptions.

The guide wire 30 is inserted into the first lumen 12a of the second sheath 12 (not illustrated) through the guide wire insertion opening 20b and is conveyed to an opening at the distal end side (distal end side) of the first lumen 11a of the first sheath 11.

Figure 33:
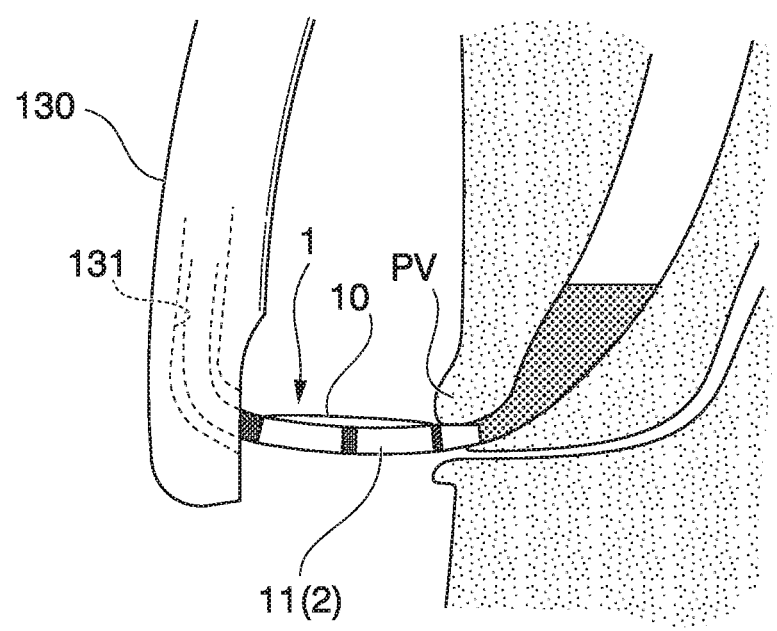
FIG. 33 is a schematic view illustrating one process during use of the treatment tool for an endoscope.

Then, as illustrated in FIG. 33, the insertion part 2 of the treatment tool 1 is inserted from the distal end side into a treatment tool channel 131 of the endoscope 130.

When the distal end of the insertion part 2 of the treatment tool 1 protrudes from a distal end of the treatment tool channel 131 of the endoscope 130, the distal end of the treatment tool 1 is inserted into a duodenal papilla PV by operating the endo scope 130 and operating the treatment tool 1.

Figure 34:
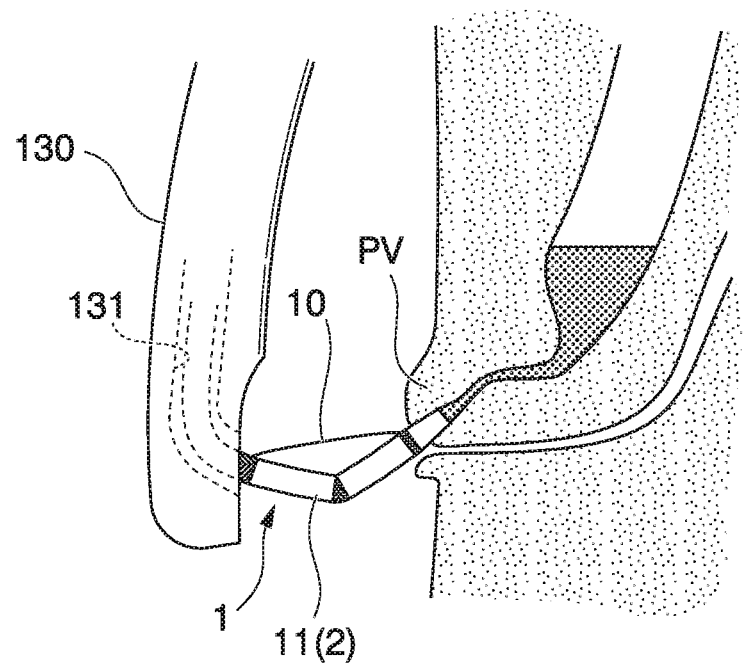
FIG. 34 is a schematic view illustrating one process during use of the treatment tool for an endoscope.
Figure 35:
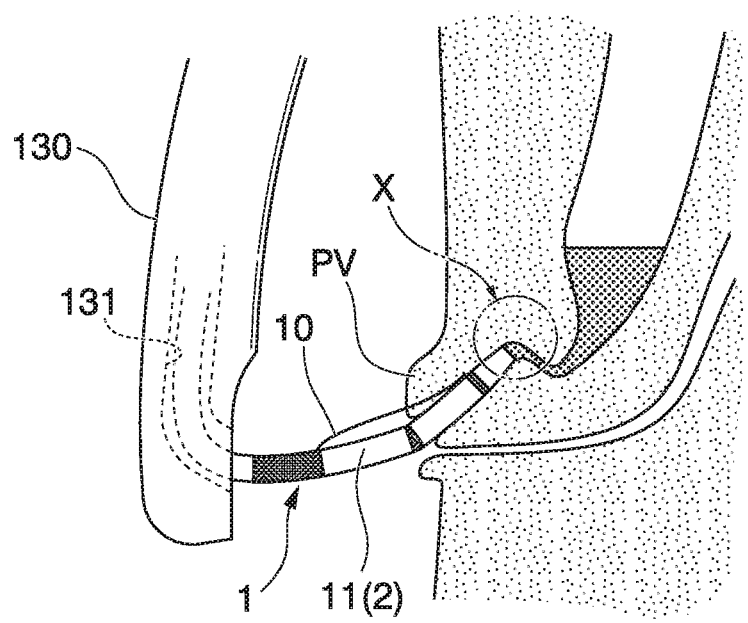
FIG. 35 is a schematic view illustrating one process during use of the treatment tool for an endoscope.

The guide wire 30 is used as a technique for inserting the distal end of the treatment tool 1 into the duodenal papilla PV in some cases. As illustrated in FIG. 34, a tube inside the duodenal papilla PV is rarely bent in some cases. In such a duodenal papilla PV, it is sometimes difficult to insert the insertion part 2 into a bile duct just by aligning a direction of the insertion part 2 of the treatment tool 1 with a direction of the bile duct because the distal end of the insertion part 2 of the treatment tool 1 bumps into a bent portion X (see FIG. 35) of a lumen bent from the duodenal papilla PV to the bile duct.

Figure 36:
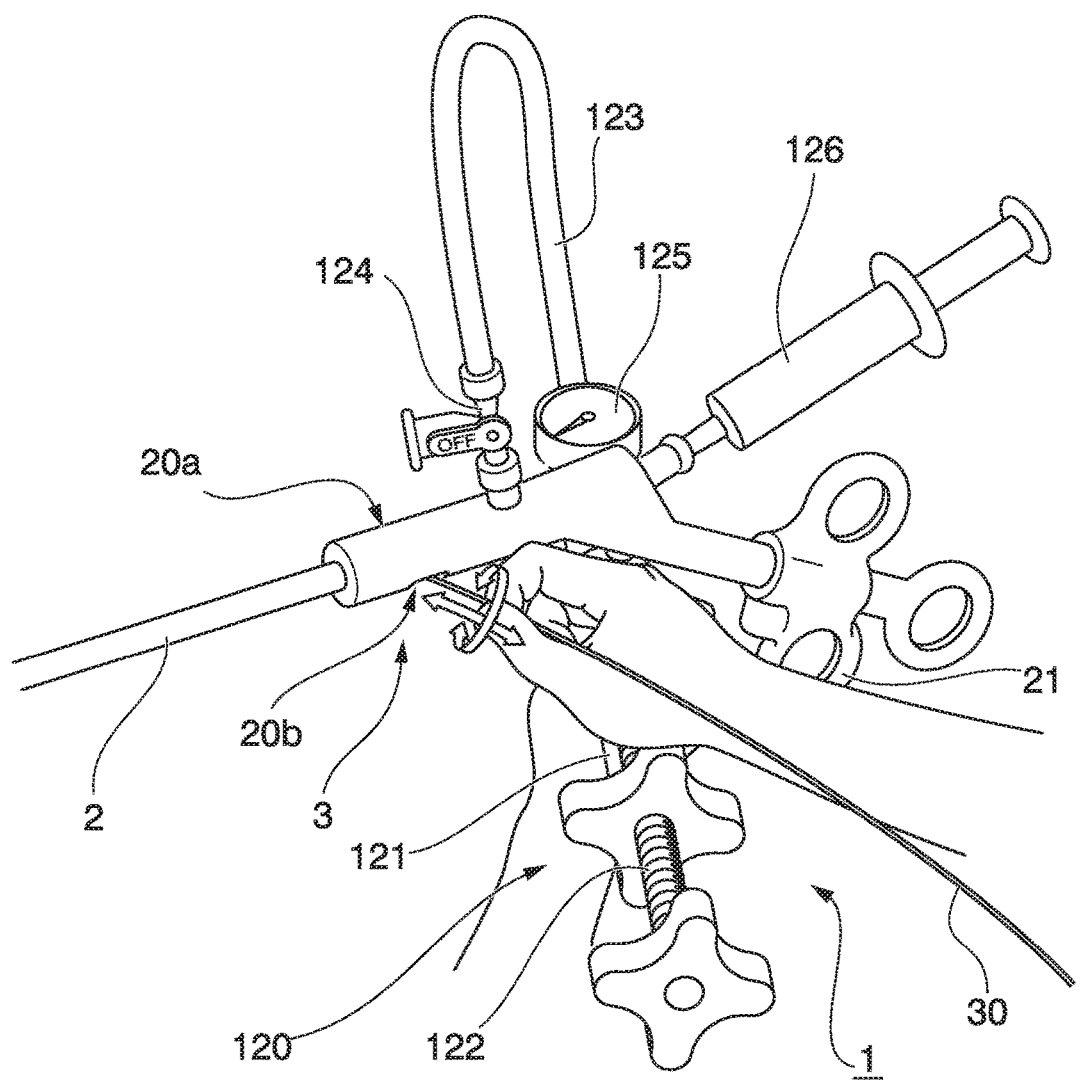
FIG. 36 is a schematic view illustrating one process during use of the treatment tool for an endoscope.
Figure 37:
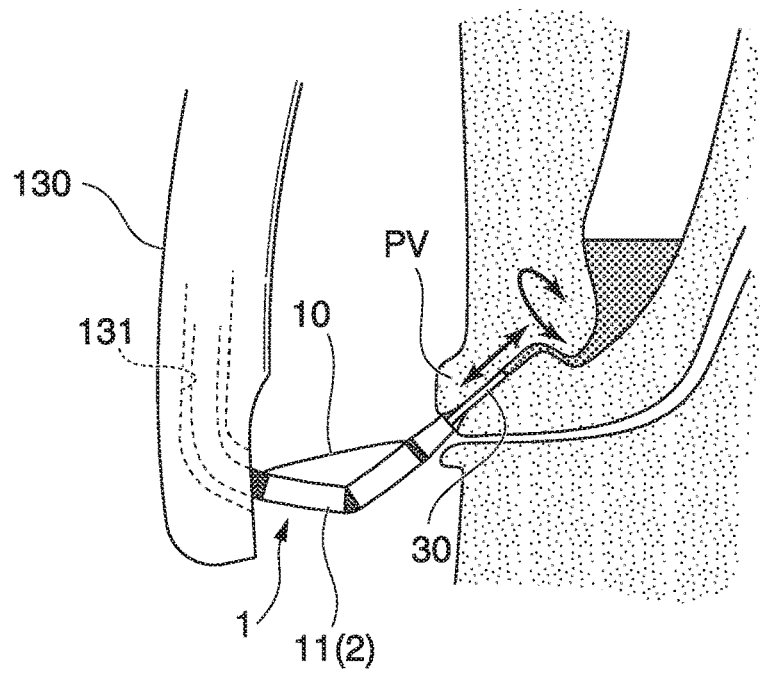
FIG. 37 is a schematic view illustrating one process during use of the treatment tool for an endoscope.
Figure 38:
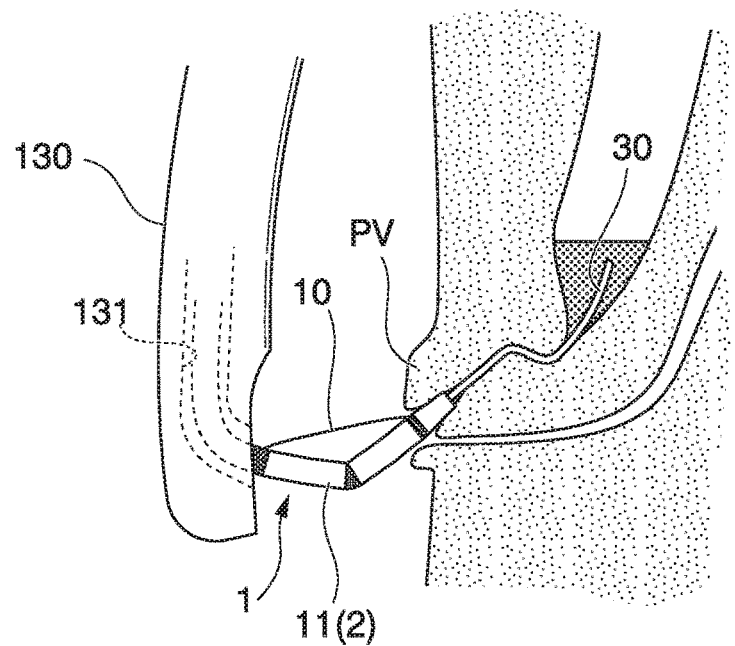
FIG. 38 is a schematic view illustrating one process during use of the treatment tool for an endoscope.
Figure 39:
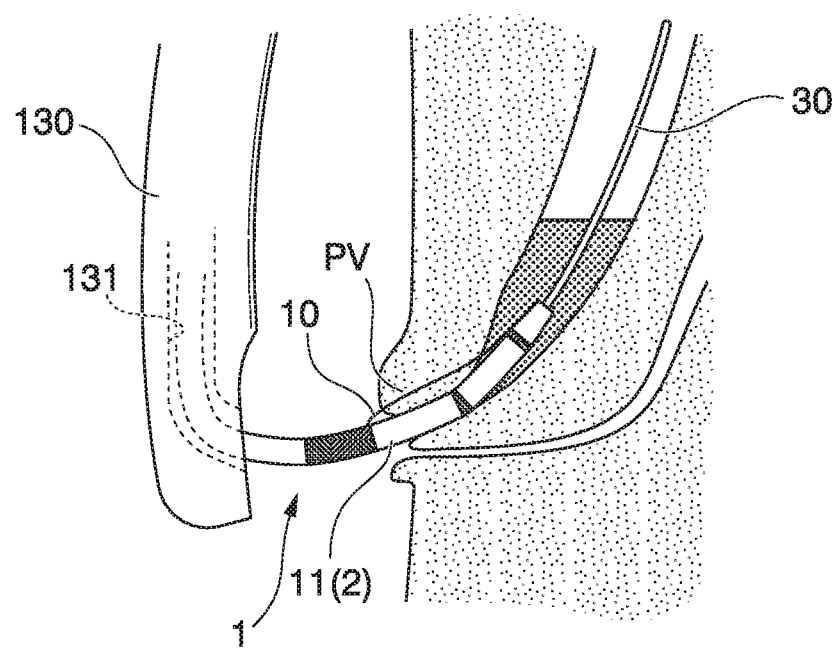
FIG. 39 is a schematic view illustrating one process during use of the treatment tool for an endoscope.

When the distal end of the insertion part 2 of the treatment tool 1 bumps into the bent portion of the lumen bent from the duodenal papilla PV to the bile duct, as illustrated in FIGS. 36 and 37, the guide wire 30 having a more flexible distal end portion than the insertion part 2 is used, and the guide wire 30 is first inserted from the duodenal papilla PV toward the bile duct.

As a specific operation, the guide wire 30 slightly protrudes from the distal end of the treatment tool 1 in a state in which the distal end of the insertion part 2 of the treatment tool 1 is placed at an entrance of the duodenal papilla PV (see FIG. 37). In this state, a direction of the flexible distal end of the guide wire 30 is oriented along a curve in the duodenal papilla PV by gently and slowly advancing or rotating the proximal end portion of the guide wire 30. As a result, the guide wire 30 can advance toward the bile duct over the curve of the duodenal papilla PV (see FIG. 38). Due to this, the guide wire 30 configured to guide the treatment tool 1 is installed in the duodenal papilla PV before the treatment tool 1 is inserted into the duodenal papilla PV. Then, the insertion part 2 of the treatment tool 1 may be inserted deeply into the duodenal papilla PV along the guide wire 30 (see FIG. 39).

Figure 40:
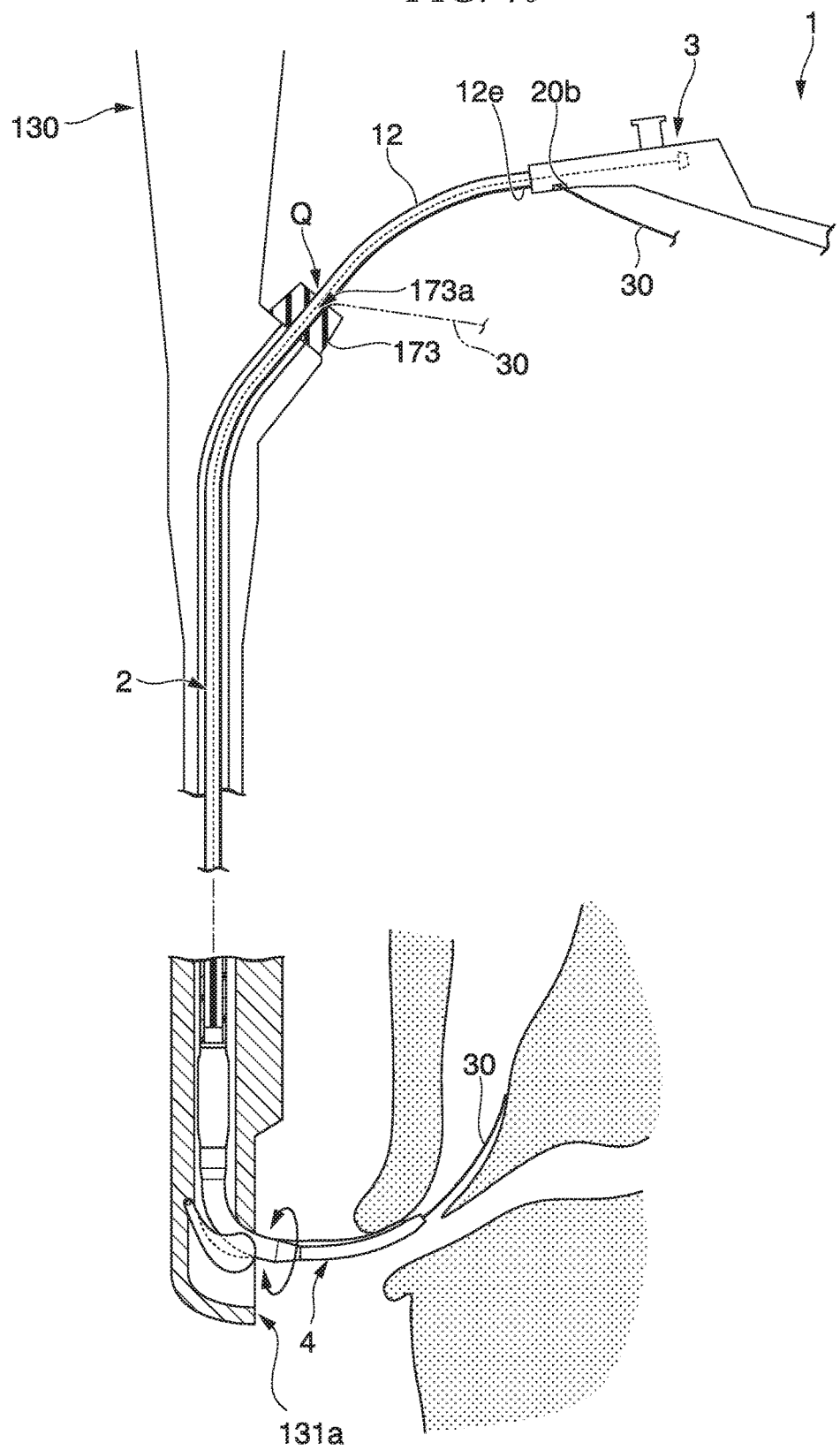
FIG. 40 is a schematic view illustrating one process during use of the treatment tool for an endoscope.

As illustrated in FIG. 40, the slit 12e having a width slightly smaller than the outer diameter of the guide wire 30 is formed in the second sheath 12 of the insertion part 2. The slit 12e is formed in the first lumen 12a (not illustrated), which is a guide wire lumen.

Due to the second sheath 12 being formed of a resin material, the second sheath 12 can be elastically deformed. The second sheath 12 may withdraw the guide wire 30 to the outside even through the slit 12e by being elastically deformed. For example, a position at which the guide wire 30 is withdrawn to the outside of the second sheath 12 may be moved to a guide wire operation position Q in the vicinity of a forceps plug 173 of the endoscope 130.

In this case, it is easy for a user operating the endoscope 130 to operate (insert, retract, or the like) the guide wire 30.

Even when the operation begins with only the treatment tool 1 and it is desired for the guide wire 30 to be inserted from the guide wire insertion opening 20b in the middle, because the slit 12e is smaller than the outer diameter of the guide wire 30, there is no possibility that the guide wire 30 is withdrawn to the outside of the slit 12e in the middle. Because of this, the guide wire 30 can be inserted into the distal end of the treatment tool 1.

Figure 41:
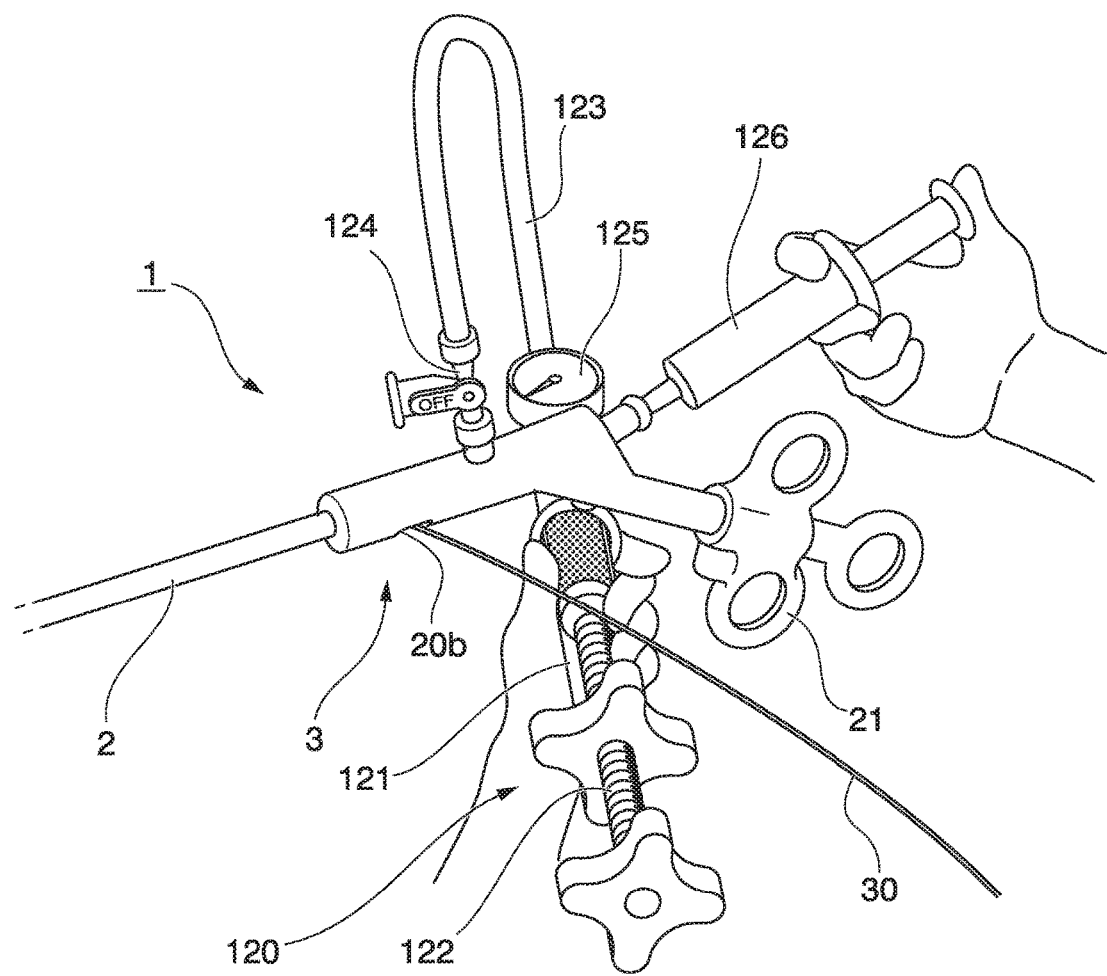
FIG. 41 is a schematic view illustrating one process during use of the treatment tool for an endoscope.
Figure 42:
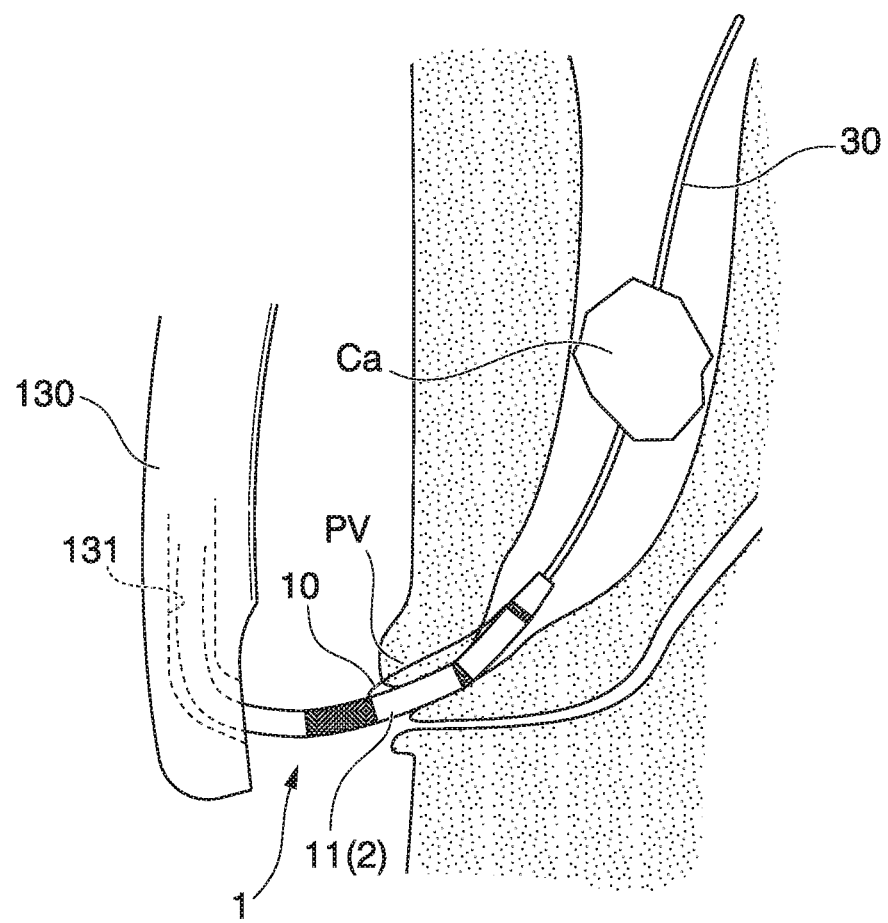
FIG. 42 is a schematic view illustrating one process during use of the treatment tool for an endoscope.
Figure 43:
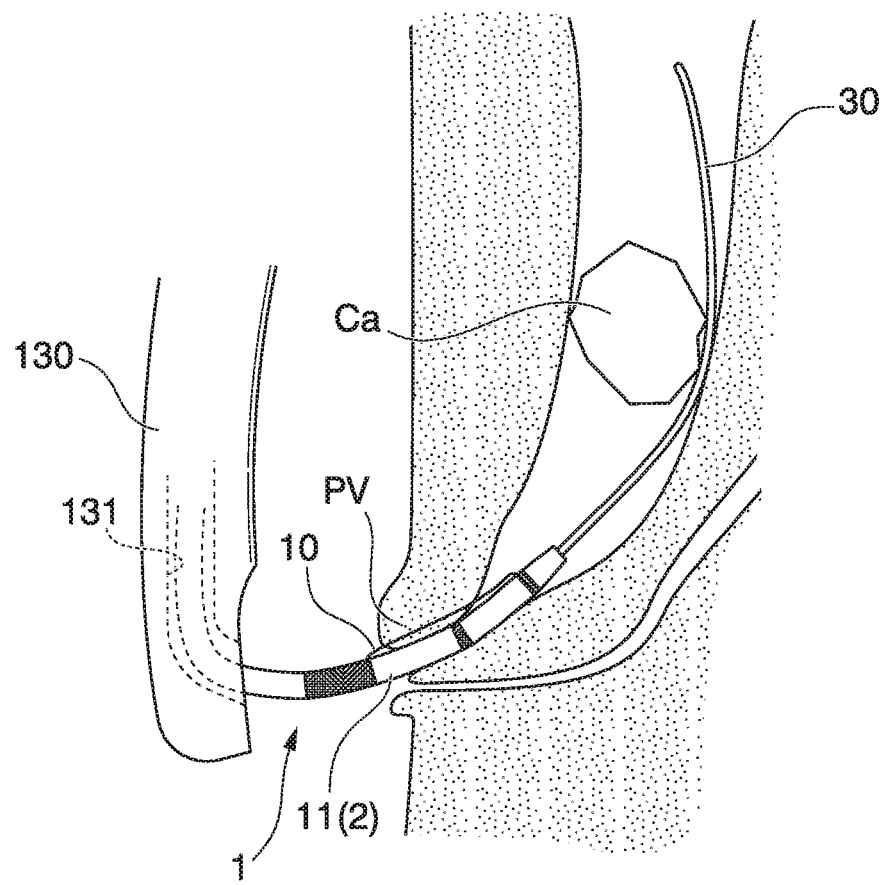
FIG. 43 is a schematic view illustrating one process during use of the treatment tool for an endoscope.
Figure 44:
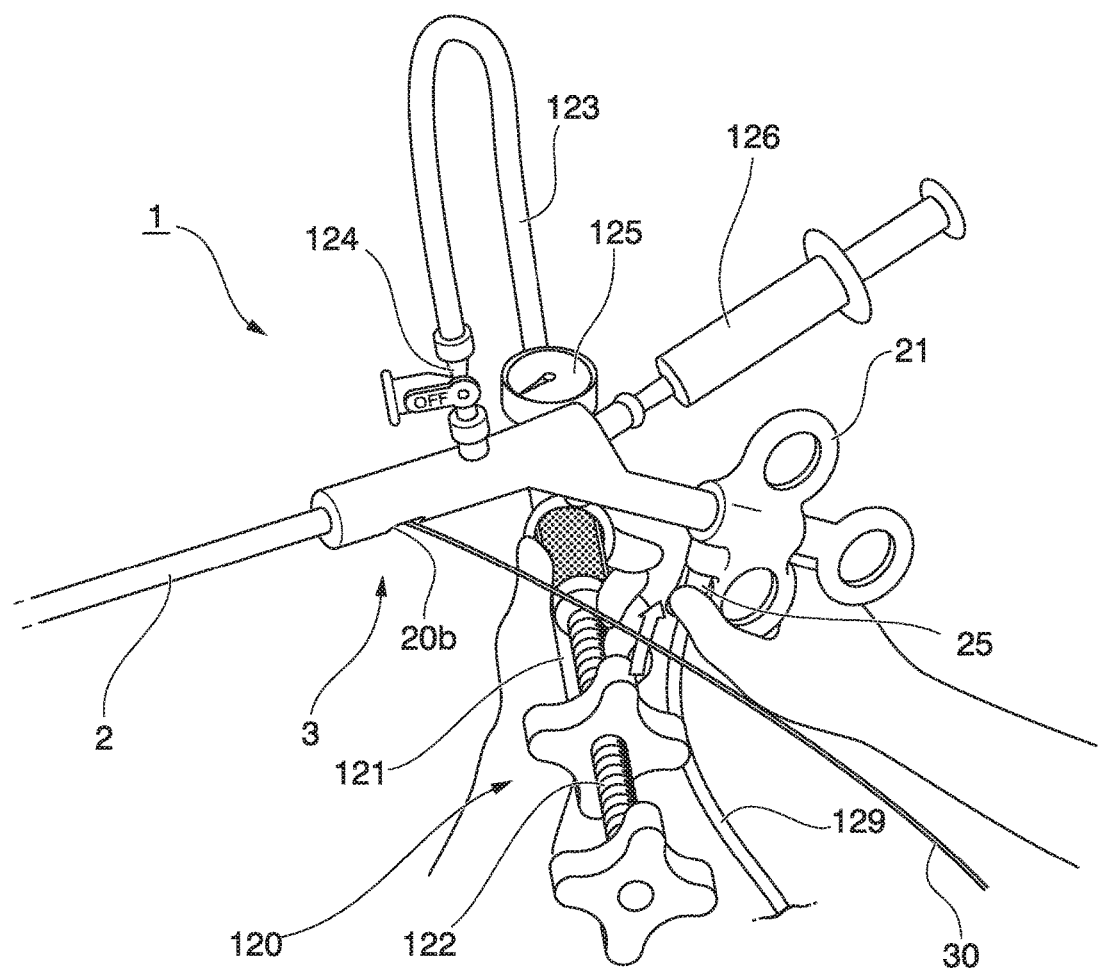
FIG. 44 is a schematic view illustrating one process during use of the treatment tool for an endoscope.

When the insertion part 2 of the treatment tool 1 is inserted into the bile duct, as illustrated in FIG. 41, the bile duct is filled with the contrast medium from the syringe 126 attached to the operation part 3. When the bile duct is imaged and a stone Ca is checked, as illustrated in FIG. 42, the distal end portion of the knife wire 10 is moved to an incision position of the duodenal papilla PV, as illustrated in FIG. 43. Also, as illustrated in FIG. 44, a connecting cord 129 of the high-frequency power supply device 128 is connected to the plug 25 of the operation part 3.

Figure 45:
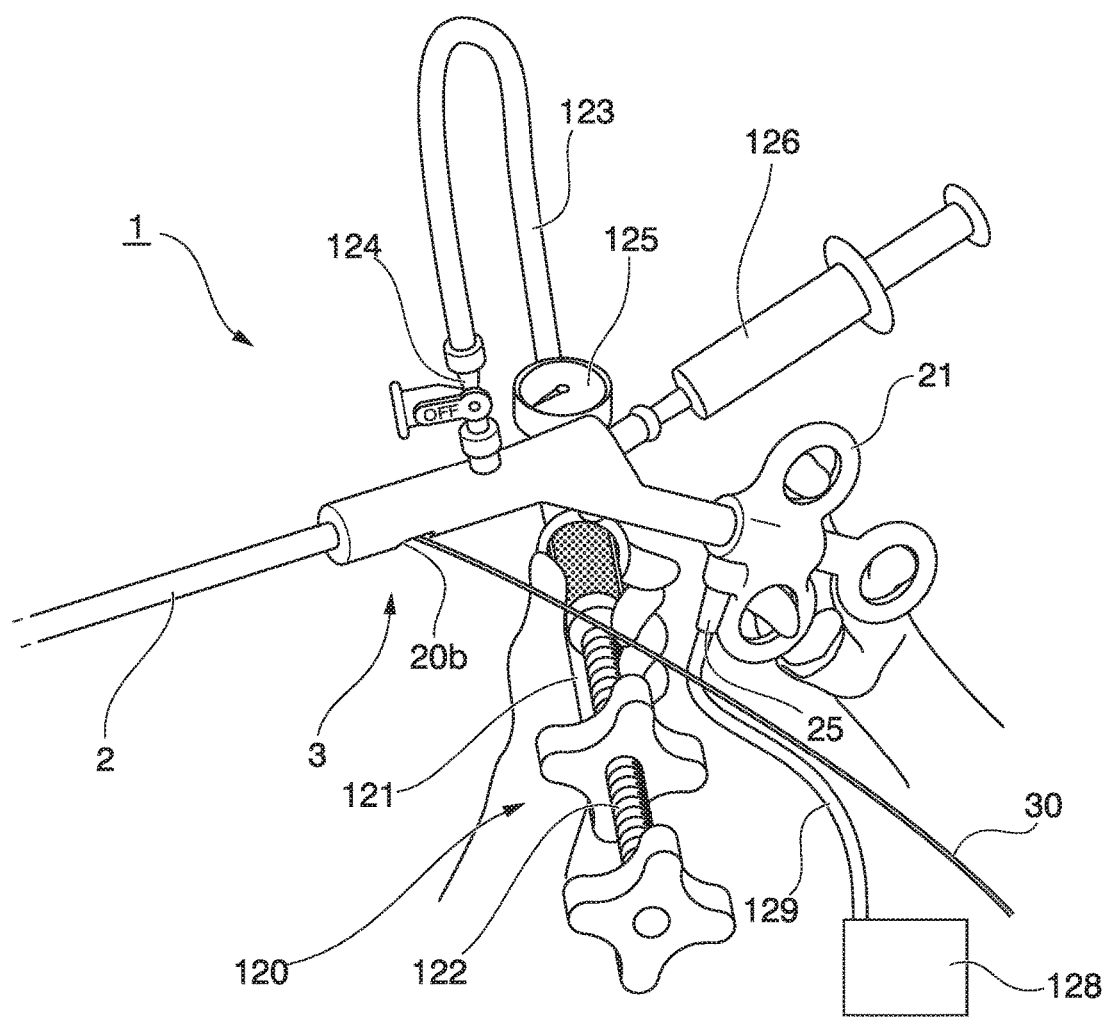
FIG. 45 is a schematic view illustrating one process during use of the treatment tool for an endoscope.
Figure 46:
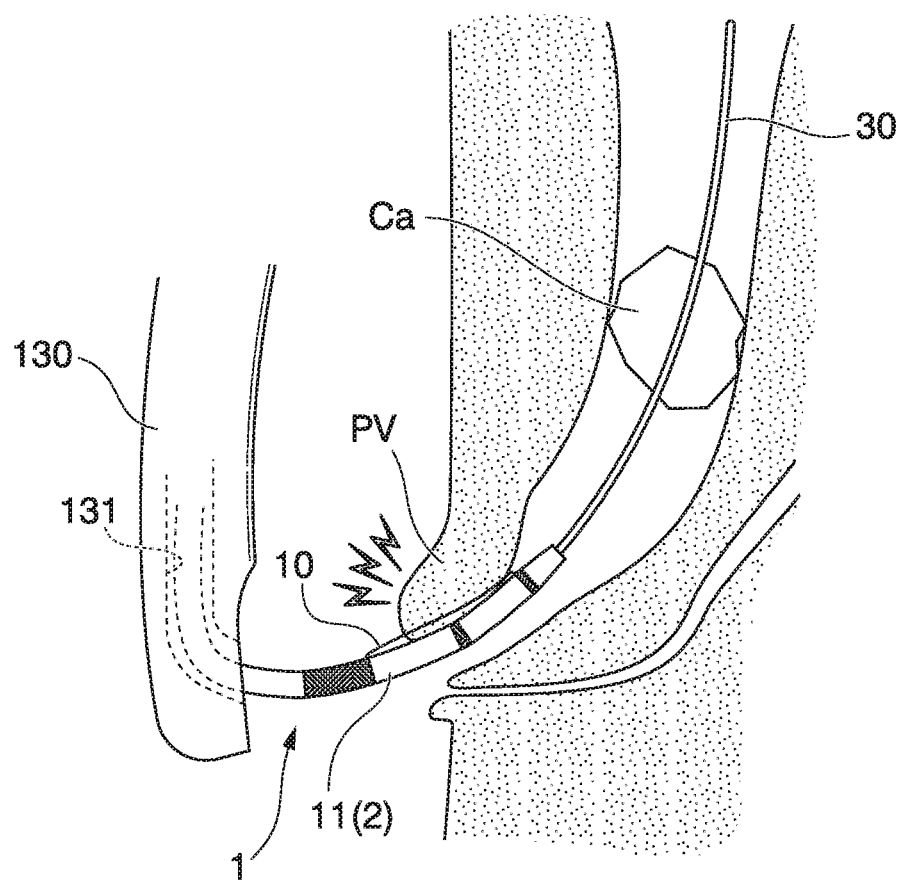
FIG. 46 is a schematic view illustrating one process during use of the treatment tool for an endoscope.

When the high-frequency power supply device 128 is connected to the plug 25, the distal end portion of the knife wire 10 is slightly pulled into an arc shape as illustrated in FIG. 46 to come into contact with the duodenal papilla PV by the slider 21 of the operation part 3 being operated, as illustrated in FIG. 45, and a high-frequency current is passed therethrough to incise the duodenal papilla PV.

Figure 47:
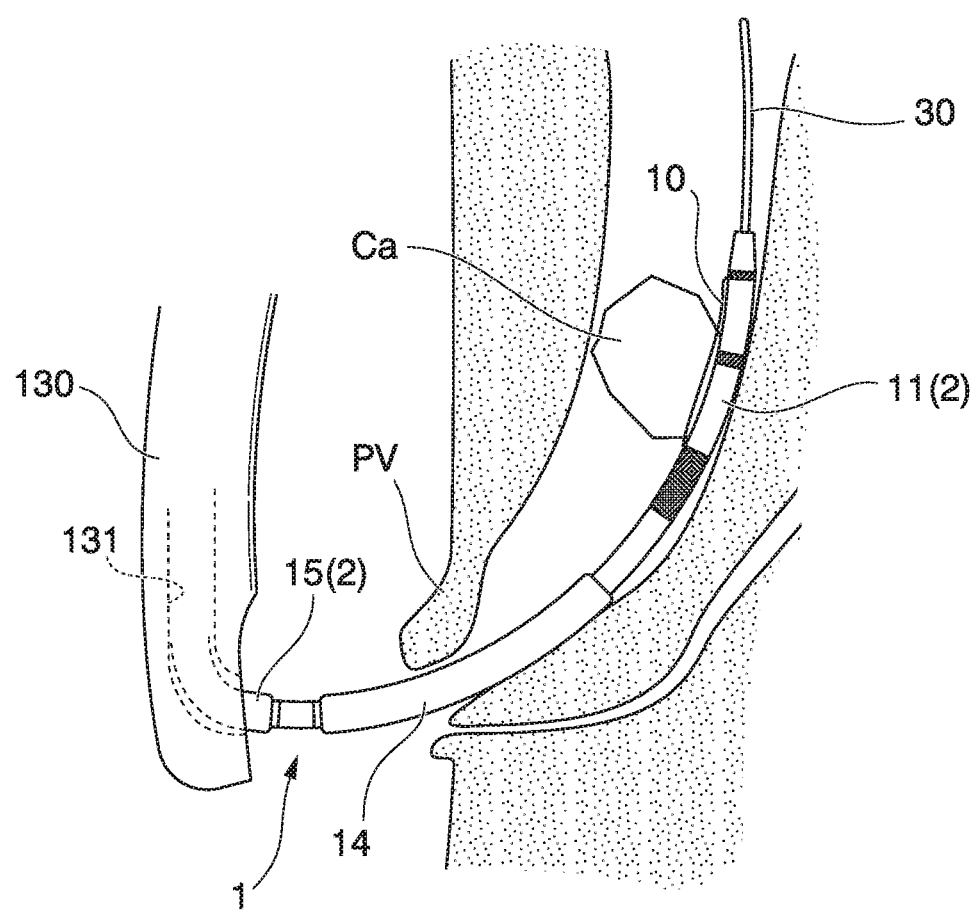
FIG. 47 is a schematic view illustrating one process during use of the treatment tool for an endoscope.

After the duodenal papilla PV is incised using the knife wire 10, the insertion part 2 of the treatment tool 1 is advanced until the center of the balloon 14 almost reaches the entrance of the duodenal papilla PV in the longitudinal direction, as illustrated in FIG. 47.

Figure 48:
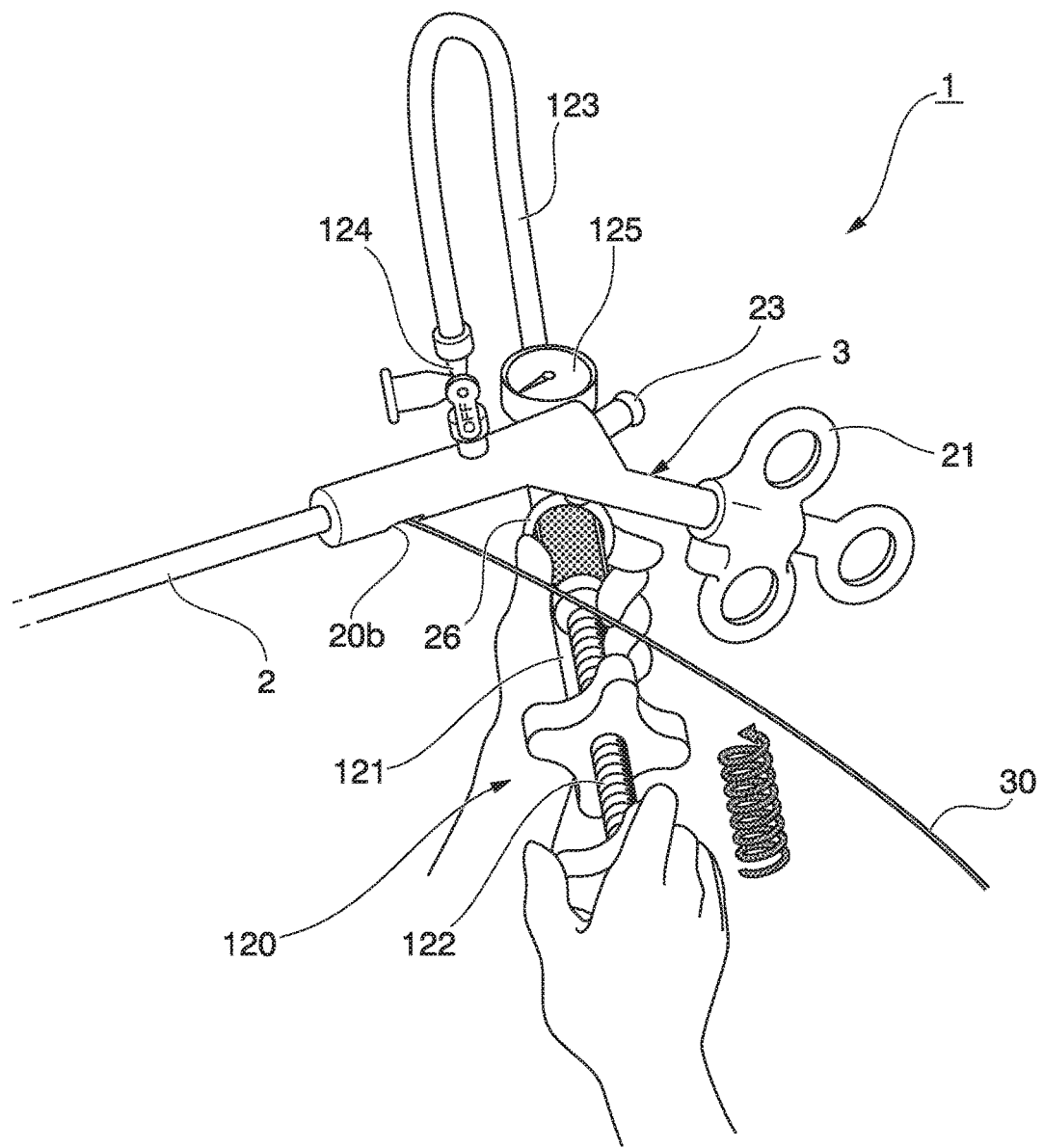
FIG. 48 is a schematic view illustrating one process during use of the treatment tool for an endoscope.
Figure 49:
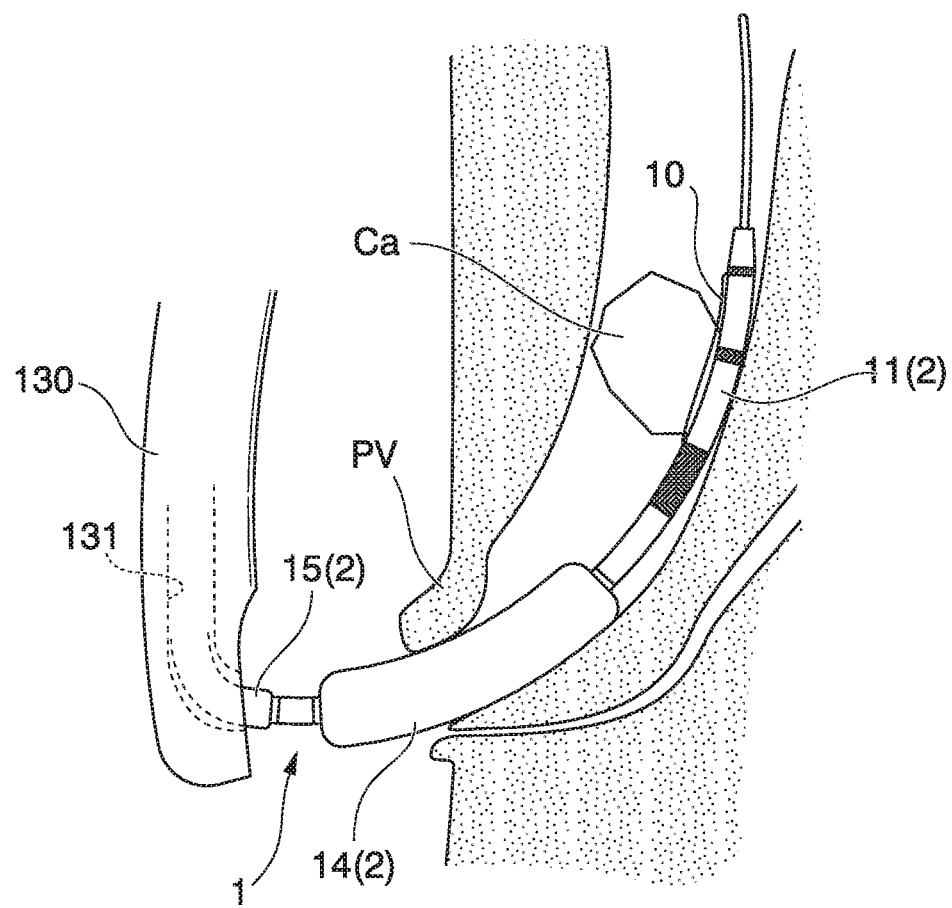
FIG. 49 is a schematic view illustrating one process during use of the treatment tool for an endoscope.

Then, a plunger 122 of the pressurizer 120 is advanced to dilate the balloon 14 in a state in which the balloon 14 is placed inside the duodenal papilla PV, as illustrated in FIGS. 48 and 49.

Figure 50:
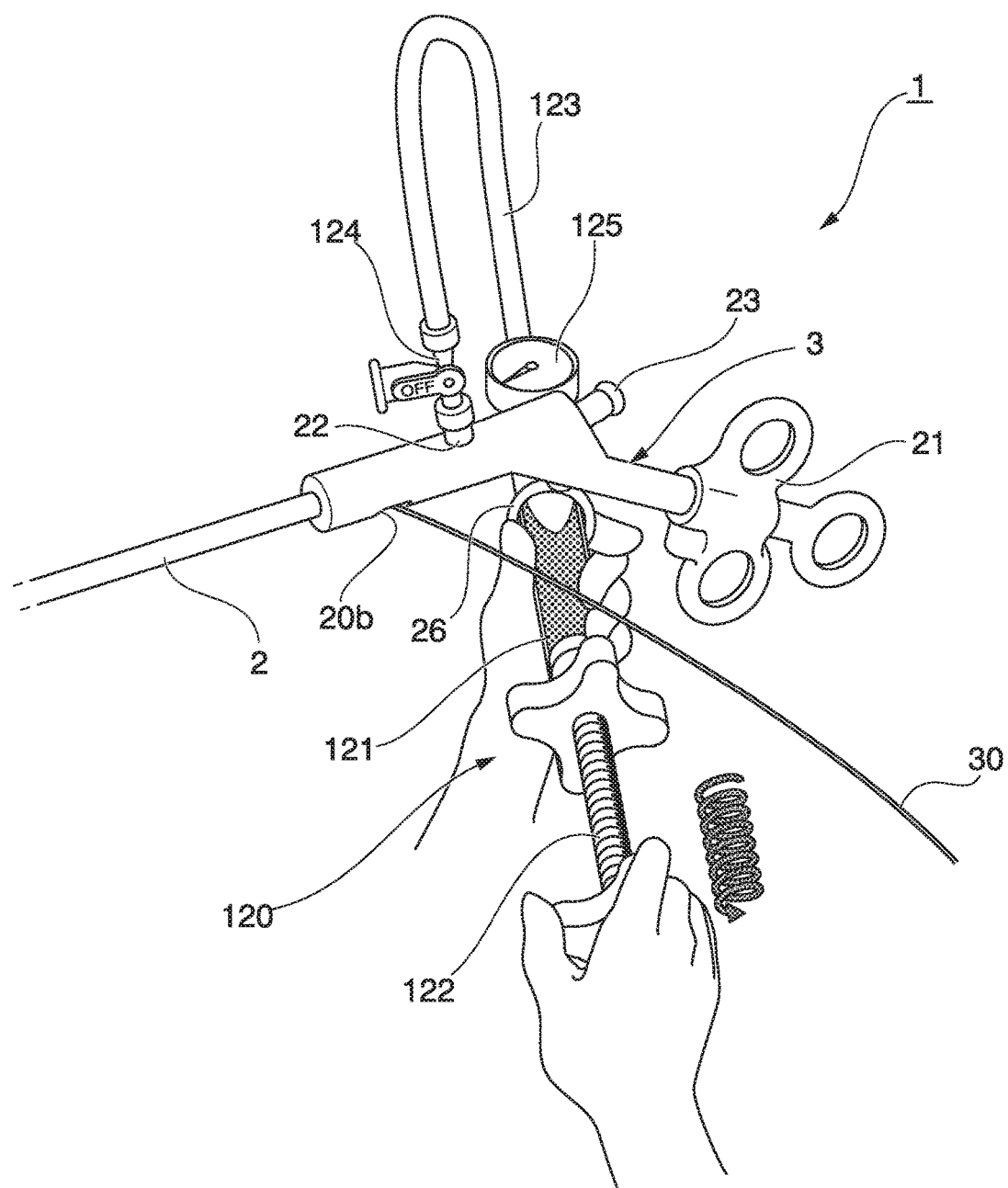
FIG. 50 is a schematic view illustrating one process during use of the treatment tool for an endoscope.
Figure 51:
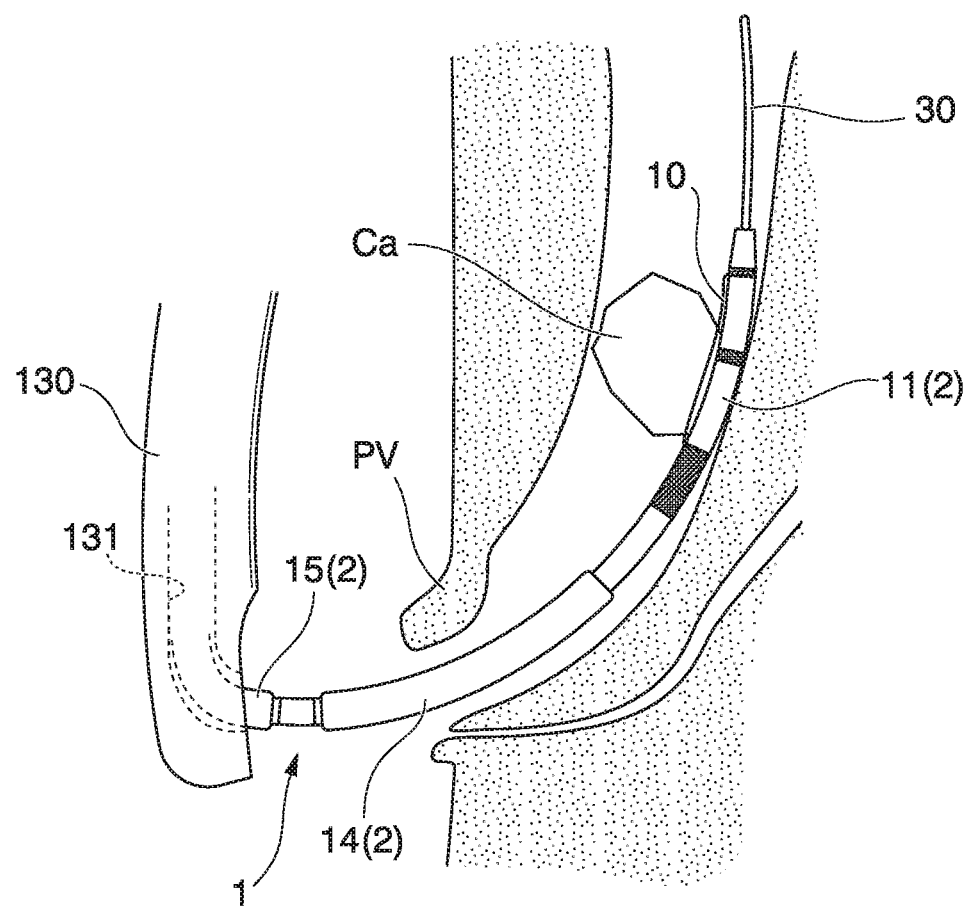
FIG. 51 is a schematic view illustrating one process during use of the treatment tool for an endoscope.

When the duodenal papilla PV is dilated by the balloon 14, the plunger 122 of the pressurizer 120 is retracted, as illustrated in FIG. 50, to contract the balloon 14 in the duodenal papilla PV, as illustrated in FIG. 51.

Figure 52:
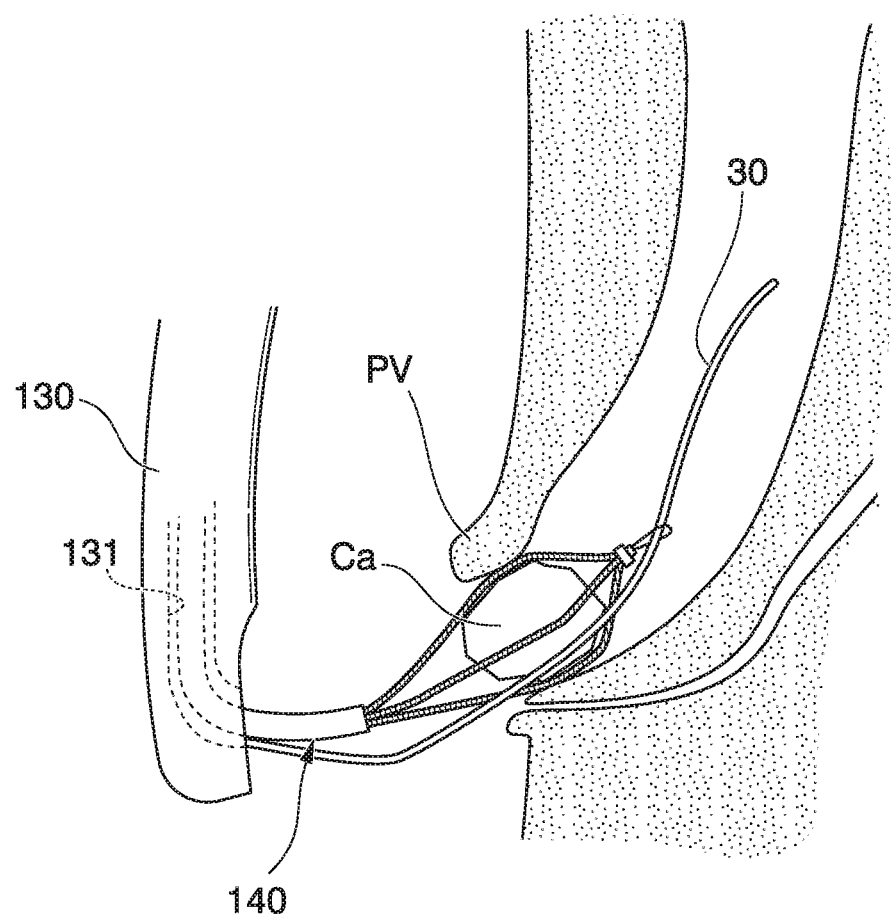
FIG. 52 is a schematic view illustrating one process during use of the treatment tool for an endoscope.

Then, the treatment tool 1 is pulled out of the treatment tool channel 131 of the endoscope 130, a stone-removing basket 140 or the like is attached to the endoscope 130, as illustrated in FIG. 52, the basket 140 is introduced from the duodenal papilla PV to the bile duct, and the stone Ca is collected.

An action of the elongation suppressing wire 16 in the treatment tool 1 will be described.

Figure 53:
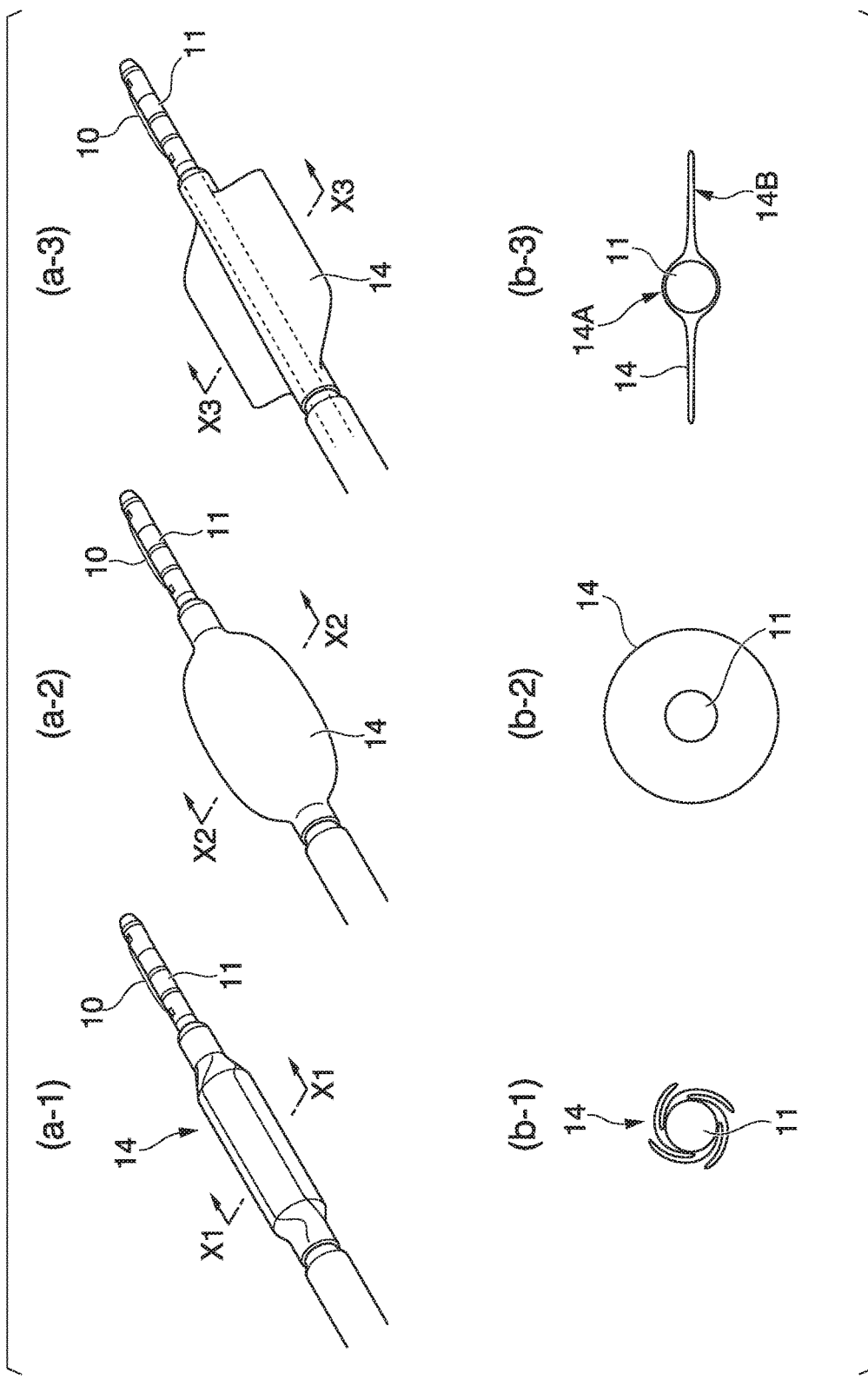
FIG. 53 is a schematic view illustrating an operation of a balloon of the treatment tool for an endoscope according to the first embodiment of the present invention.
Figure 54:
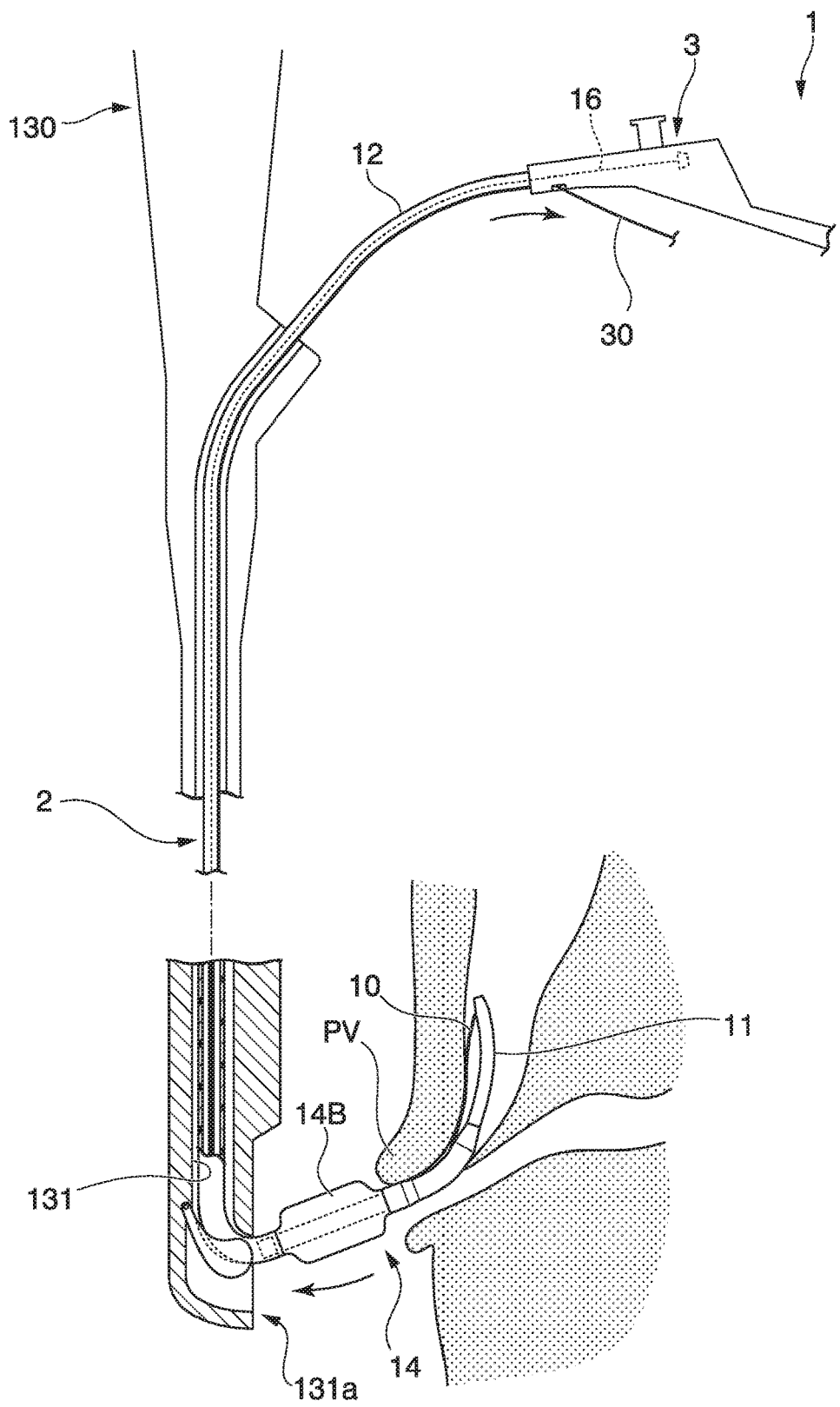
FIG. 54 is a schematic view illustrating one process during use of the treatment tool for an endoscope according to the first embodiment of the present invention.
Figure 55:
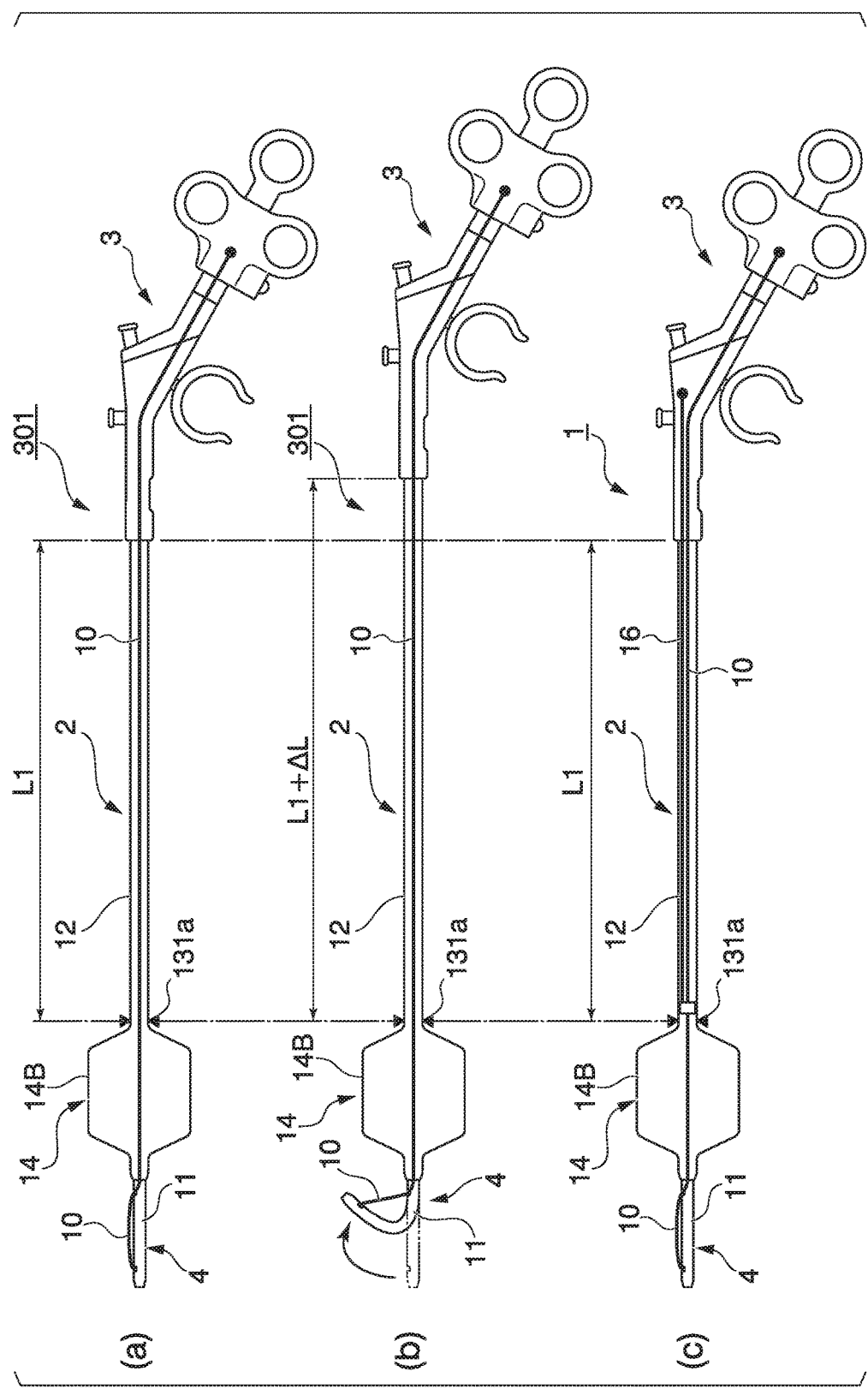
FIG. 55 is a cross-sectional view for describing an action of the elongation suppressing wire of the treatment tool for an endoscope according to the first embodiment of the present invention.

FIG. 53 is a schematic view illustrating an operation of a balloon of the treatment tool for an endoscope according to the first embodiment of the present invention. In FIG. 53, (a-1) is a schematic perspective view illustrating a mode when an unused balloon is contracted. Likewise, (a-2) is a schematic perspective view illustrating a mode when the balloon is dilated. Likewise, (a-3) is a schematic perspective view illustrating a mode when the balloon is contracted after being dilated. In FIGS. 53, (b-1), (b-2), and (b-3) are respectively a cross-sectional view taken along line X1-X1 in (a-1), a cross-sectional view taken along line X2-X2 in (a-2), and a cross-sectional view taken along line X3-X3 in (a-3). FIG. 54 is a schematic view illustrating one process during use of the treatment tool for an endoscope according to the first embodiment of the present invention. FIG. 55 is a cross-sectional view for describing an action of the elongation suppressing wire of the treatment tool for an endoscope according to the first embodiment of the present invention.

As described above, the elongation suppressing wire 16 is arranged in parallel with the first sheath 11, a part of the knife wire 10, and the second sheath 12 inside the insertion part 2. Because of this, when the insertion part 2 is pulled, elongation of the insertion part 2 is suppressed by the tensile rigidity of the elongation suppressing wire 16 in a range in which the elongation suppressing wire 16 is parallel thereto.

An example of a case in which the insertion part 2 is drawn into the treatment tool channel 131 of the endoscope 130 after the balloon is contracted may be given as an example of the case in which the insertion part 2 is pulled.

As illustrated in (a-1) and (b-1) of FIG. 53, the unused balloon 14 is contracted because a dilation fluid is not supplied into the balloon 14. At this time, the balloon 14 is folded along the outer circumferential surface of the first sheath 11. The folded balloon 14 is placed in a cylindrical range having a slightly larger diameter than the first sheath 11.

As described above with reference to FIGS. 48 and 49, the balloon 14 is dilated when the dilation liquid is introduced into the balloon 14 by the pressurizer 120, as illustrated in (a-2) and (b-2) of FIG. 53.

As described above with reference to FIG. 50, the balloon 14 is contracted when the dilation liquid is discharged from the inside of the balloon 14 by the pressurizer 120.

At this time, the balloon 14 is contracted as if pressed and crushed in one direction in the diametric direction, as illustrated in (a-3) and (b-3) of FIG. 53. Because of this, a shape of the contracted balloon 14 is, for example, changed into a flat shape including a central portion 14A adhered to the outer circumferential surface of the first sheath 11 and a pair of protrusions 14B protruding outward in the diametric direction of the first sheath 11 due to the balloon 14 being adhered to itself.

At a time of the contraction, the protrusion 14B is, for example, made to be easily caught by a distal end opening 131a of the treatment tool channel 131 of the endoscope 130 when retracted the insertion part 2 from a tube inside the duodenal papilla PV, as schematically illustrated in FIG. 54.

Because the protrusion 14B is flexible, when retracted with a certain degree of force, the protrusion 14B is deformed and enters the treatment tool channel 131. However, a tensile force acts on the entire insertion part 2 until the protrusion 14B completely enters the treatment tool channel 131.

For example, in a treatment tool 301 in which the elongation suppressing wire 16 is removed from the treatment tool 1, as illustrated in FIG. 55(a), a length of the insertion part 2 from the proximal end portion of the balloon 14 to the operation part 3 is referred to as a length L1 of the second sheath 12. It is assumed that the balloon 14 is contracted and the protrusion 14B is locked to the distal end opening 131a.

From this state, when the operation part 3 is pulled toward the distal side (proximal end side), the second sheath 12 formed of a resin material extends as illustrated in FIG. 55(b), and a length of the insertion part 2 is extended to L1+ΔL. However, because the knife wire 10 inserted into the second sheath 12 cannot extend like the second sheath 12, the knife wire 10 moves toward the proximal end side by about ΔL. As a result, the knife wire 10 protruding outward from the first sheath 11 is drawn into the first sheath 11, and the first sheath 11 in the treatment part 4 is bent.

As illustrated in FIG. 54, when the balloon 14 is locked to the distal end opening 131a, there is a possibility that tissue inside the body may be damaged due to deformation of the treatment part 4 or movement of the knife wire 10 because the knife wire 10 exposed from the first sheath 11 is placed in the vicinity of the opening of the tube inside the duodenal papilla PV.

Conversely, the treatment tool 1 of the present embodiment has the elongation suppressing wire 16 inside the insertion part 2. Because of this, as illustrated in FIG. 55(c), since the elongation suppressing wire 16 resists the tensile force even when the insertion part 2 is pulled toward the proximal end side in a state in which the balloon 14 is locked to the distal end opening 131a, elongation of the insertion part 2 hardly occurs and the length of the insertion part 2 is maintained as L1.

As a result, because there is no possibility that the knife wire 10 will be pulled toward the proximal end side, a shape of the treatment part 4 and the amount of exposure of the knife wire 10 from the first sheath 11 do not change even when the tensile force is applied. Because of this, damage to tissue inside the body due to deformation of the treatment part 4 or movement of the knife wire 10 is reliably prevented.

[Second Embodiment]

A treatment tool for an endoscope according to a second embodiment of the present invention will be described.

Figure 56:
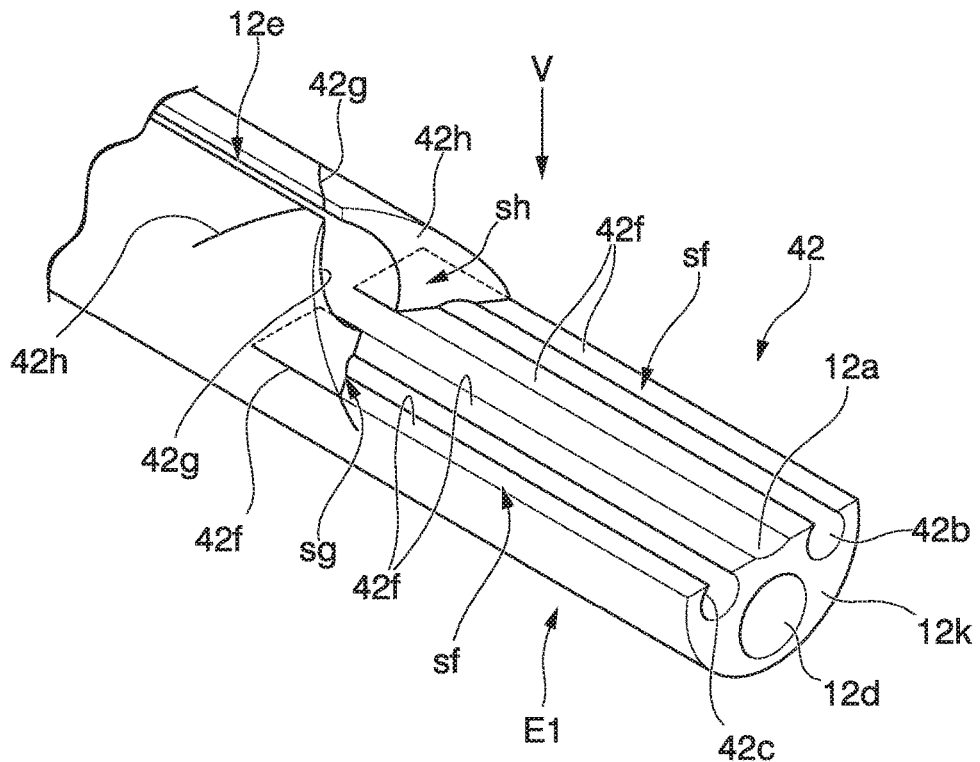
FIG. 56 is a schematic perspective view illustrating a constitution of a second end portion of a second sheath of a treatment tool for an endoscope according to a second embodiment of the present invention.
Figure 57:
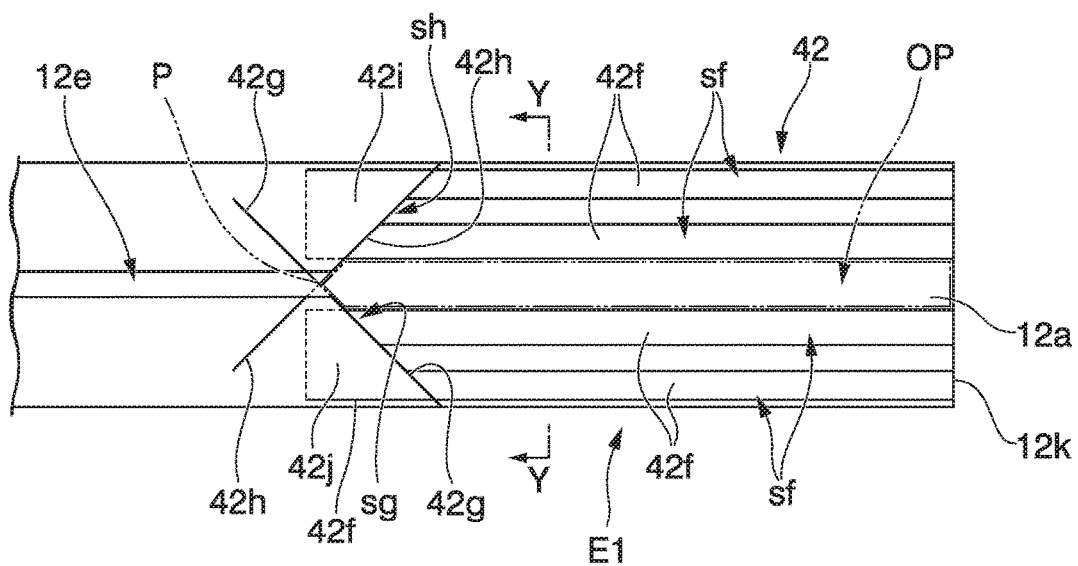
FIG. 57 is a plan view viewed from a direction of V in FIG. 56.
Figure 58:
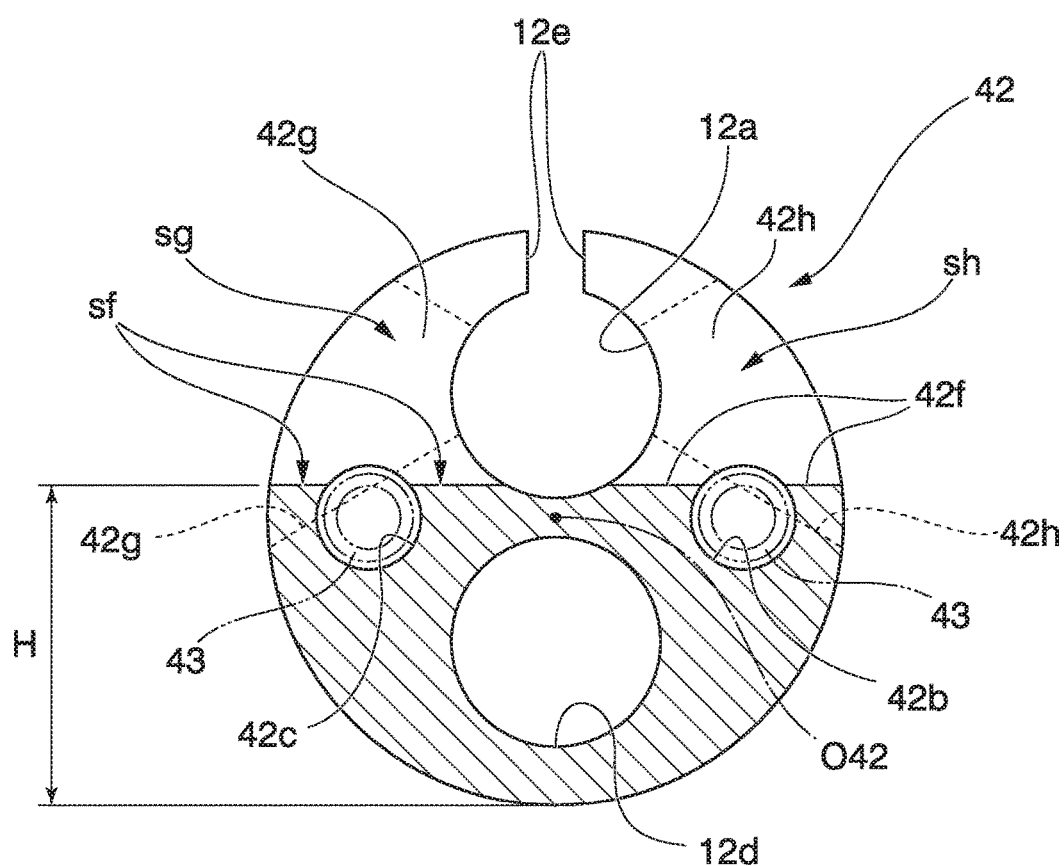
FIG. 58 is a cross-sectional view taken along line Y-Y in FIG. 57.

FIG. 56 is a schematic perspective view illustrating a constitution of a second end portion of a second sheath of the treatment tool for an endoscope according to the second embodiment of the present invention. FIG. 57 is a plan view viewed from a direction of V in FIG. 56. FIG. 58 is a cross-sectional view taken along line Y-Y in FIG. 57.

As illustrated in FIGS. 1 and 2, a treatment tool 41 according to the present embodiment includes a second sheath 42 (multi-lumen sheath) instead of the second sheath 12 of the treatment tool 1 according to the first embodiment.

Hereinafter, differences from the first embodiment will be mainly described.

As illustrated in FIGS. 56 to 58, the second sheath 42 includes a second lumen 42b and a third lumen 42c instead of the second lumen 12b and the third lumen 12c of the second sheath 12 according to the first embodiment.

In FIG. 58, the second lumen 42b and the third lumen 42c are in the same positional relationship as the second lumen 12b and the third lumen 12c. However, the second lumen 42b and the third lumen 42c may be arranged closer to the first lumen 12a in the direction in which the first lumen 12a and the fourth lumen 12d face each other. In this case, in the second sheath 42, an area beside the fourth lumen 12d can be widened. A fifth lumen, a sixth lumen, and the like may be, for example, provided in the area beside the fourth lumen 12d.

Further, the second sheath 42 includes exposed surfaces sg, sh, sf, an axially cut surface 42f, a first side cut surface 42g, and a second side cut surface 42h instead of the exposed surfaces Sg, Sh, Sf, the axially cut surface 12f, the first side cut surface 12g, and the second side cut surface 12h of the second sheath 12 according to the first embodiment.

The exposed surfaces sg and sh are the same as the exposed surfaces Sg and Sh of the first embodiment except for the fact that the exposed surfaces sg and sh are formed by the first side cut surface 42g and the second cut slit surface 42h, which will be described below.

Since the exposed surface sf is formed by the axially cut surface 42f, which will be described below, the exposed surface sf is the same as the exposed surface Sf according to the first embodiment except for the fact that the exposed surface sf is formed across the second lumen 42b and the third lumen 42c.

Compared to the axially cut surface 12f disclosed in the first embodiment formed at a position intersecting the first lumen 12a and not intersecting the second lumen 12b and the third lumen 12c, the axially cut surface 42f of the present embodiment is different from the axially cut surface 12f in the first embodiment in that the axially cut surface 42f intersects with any one of the first lumen 12a, the third lumen 42c, and the fourth lumen 12d.

When cutting is performed, the axially cut surface 42f is formed as two surfaces facing each other. However, as will be described below, the axially cut surface 12f facing the exposed surface sf is removed when all of the cutting is completed.

The first side cut surface 42g and the second side cut surface 42h are the same as the first side cut surface 12g and the second side cut surface 12h in the first embodiment in that the first side cut surface 42g and the second side cut surface 42h intersect in an X-shape at a point P on the second sheath 42 when viewed from the diametric direction passing through the center of the slit 12e, as illustrated in FIG. 57.

However, the first side cut surface 42g and the second side cut surface 42h are different from the first side cut surface 12g and the second side cut surface 12h in the first embodiment in that a portion closer to the end surface 12k intersects across the axially cut surface 42f.

The distal end portion of the first side cut surface 42g and the second side cut surface 42h in the cutting direction extends in an inclined direction that intersects the axially cut surface 42f as shown with broken lines in FIG. 58.

When cutting is performed, the first side cut surface 42g (the second side cut surface 42h) is formed as two surfaces facing each other. However, like the first side cut surface 12g and the second side cut surface 12h according to the first embodiment, the first side cut surface 42g (the second side cut surface 42h) facing the exposed surface sg (sh), which will be described below, is removed when all of the cutting is completed.

Because of this, in the present embodiment, the first side cut surface 42g (the second side cut surface 42h) forming two surfaces facing each other is formed further toward the distal end side in the second sheath 42 than the point P.

The axially cut surface 42f forming two surfaces facing each other is formed in an area ranging from a position intersecting the first side cut surface 42g forming the exposed surface sg and the second side cut surface 42h forming the exposed surface sh to the distal end portion in the cutting direction of the axially cut surface 12f.

In this way, since the distal end portion of the axially cut surface 42f is placed further toward the distal end side than the intersecting position thereof with the exposed surface sg, a triangular piece-like part 42j having the exposed surface sg and the axially cut surface 42f at an outer edge thereof is formed. Likewise, since the distal end portion of the axially cut surface 42f is placed further toward the distal end side than the intersecting position with the exposed surface sh, a triangular piece-like part 42i having the exposed surface sh and the axially cut surface 42f at an outer edge thereof is formed.

By the above constitution, as illustrated in FIG. 57, a side portion of the second sheath 42 is cut out at the first end portion E1 of the second sheath 42, and the same opening OP as the first embodiment is formed. In the opening OP, the inner circumferential surface of the first lumen 12a is exposed outward.

The opening OP in the present embodiment is surrounded by a pair of exposed surfaces sf consisting of two types of surfaces and the exposed surfaces sg and sh being arranged in a substantially U-shape.

Although not particularly illustrated, the first end portion E1 of the second sheath 42 having the above constitution are inserted into the distal end tubular part 20a and fixed to the distal end tubular part 20a in same the positional relationship as the second sheath 12.

That is, the first end portion E1 of the second sheath 42 is inserted into the distal end tubular part 20a so that the slit 12e is placed at the center of the slit 20c when viewed from the diametric direction. The position of the first end portion E1 in the axial direction is a position at which the first side cut surface 42g and the second side cut surface 42h are further toward the distal end side than the main opening distal end surface 20k and the end surface 12k of the second sheath 42 is further toward the proximal end side than the inclined portion 20e.

However, in the second sheath 42, because the axially cut surface 42f is cut into the second lumen 42b and the third lumen 42c, the second lumen 42b and the third lumen 42c are open in the diametric direction in the first end portion E1.

Accordingly, to prevent an object inserted into the second lumen 42b and the third lumen 42c from being exposed, a tube 43, indicated by two-dot chain lines in FIG. 58, is inserted into the second lumen 42b and the third lumen 42c.

Next, a method for manufacturing the treatment tool 41 will be described mainly with reference to a method for manufacturing the second sheath 42.

Figure 59:
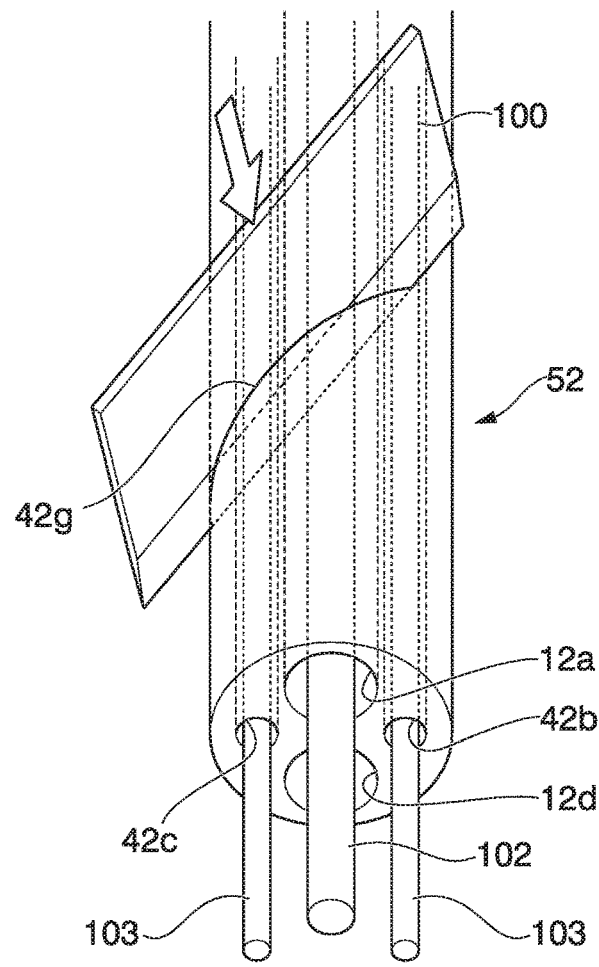
FIG. 59 is a perspective process explanatory view of a process for manufacturing the treatment tool for an endoscope according to the second embodiment of the present invention.
Figure 60:
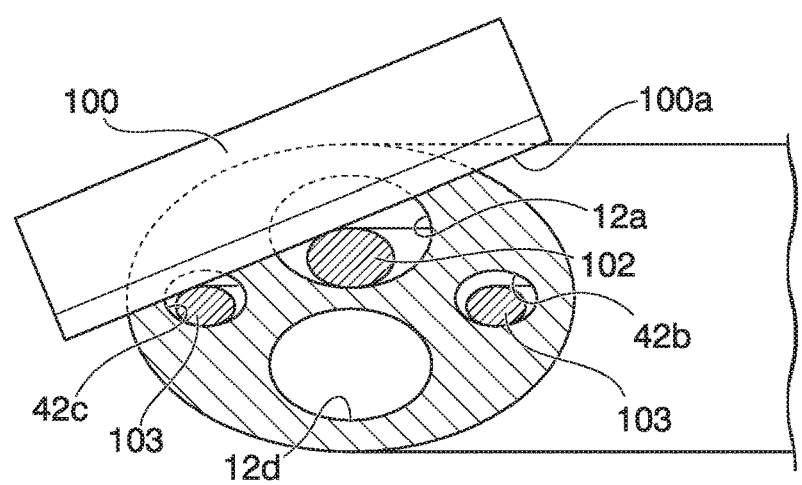
FIG. 60 is a cross-sectional process explanatory diagram of the process for manufacturing the treatment tool for an endoscope according to the second embodiment of the present invention.
Figure 61:
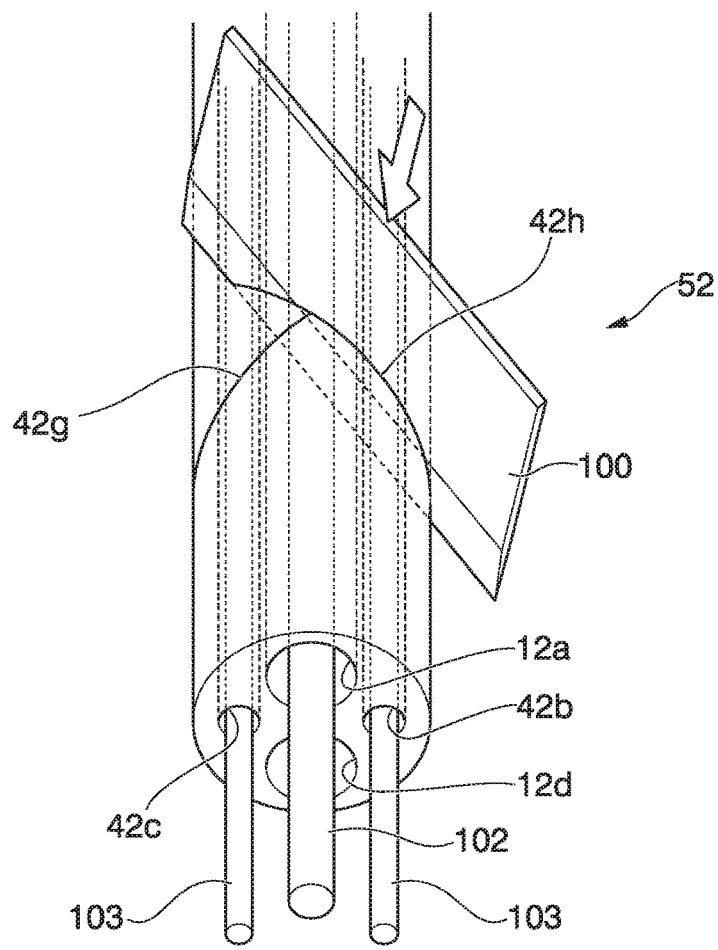
FIG. 61 is a perspective process explanatory view of the process for manufacturing the treatment tool for an endoscope according to the second embodiment of the present invention.
Figure 62:
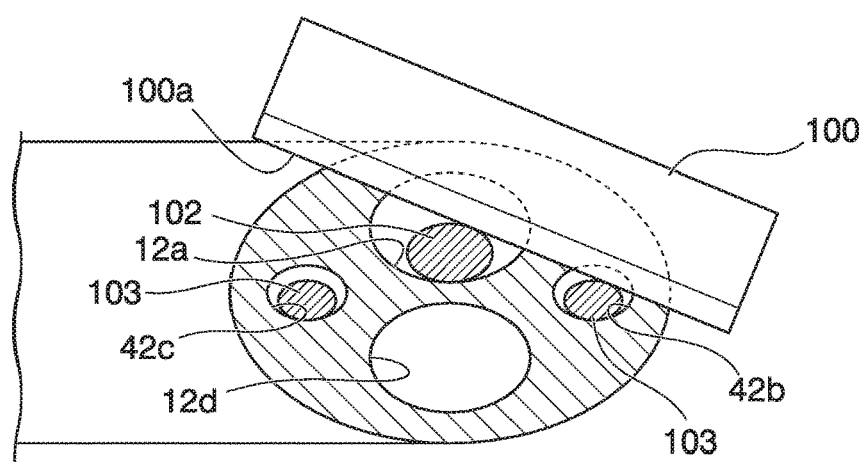
FIG. 62 is a cross-sectional process explanatory view of the process for manufacturing the treatment tool for an endoscope according to the second embodiment of the present invention.
Figure 63:
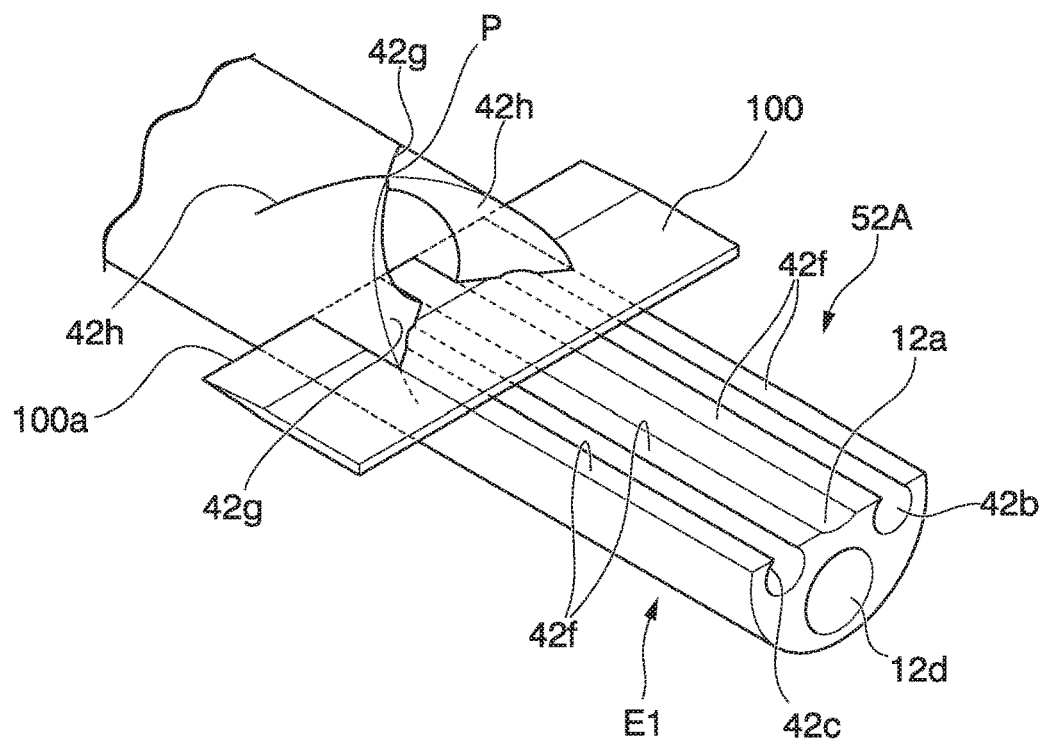
FIG. 63 is a perspective process explanatory view of the process for manufacturing the treatment tool for an endoscope according to the second embodiment of the present invention.
Figure 64:
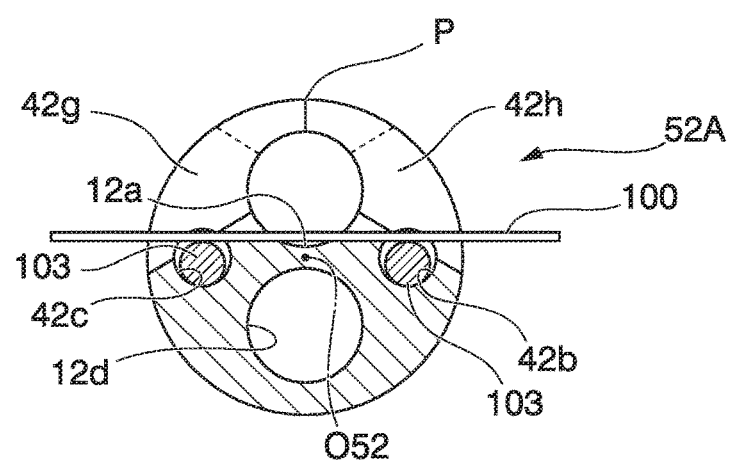
FIG. 64 is a cross-sectional process explanatory view of the process for manufacturing the treatment tool for an endoscope according to the second embodiment of the present invention.
Figure 65:
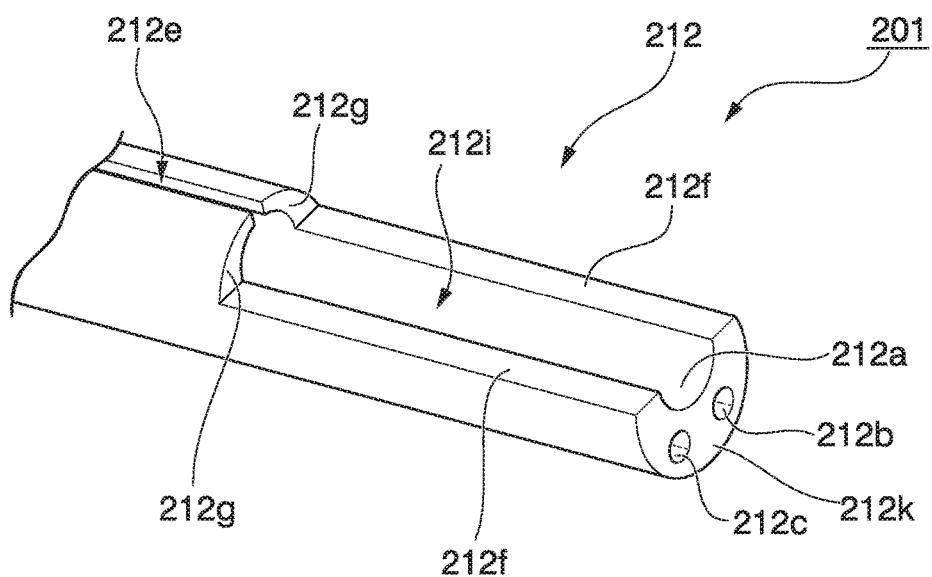
FIG. 65 is a schematic perspective view illustrating a proximal end portion of a multi-lumen tube according to an example of a treatment tool for an endoscope of a prior art.
Figure 66:
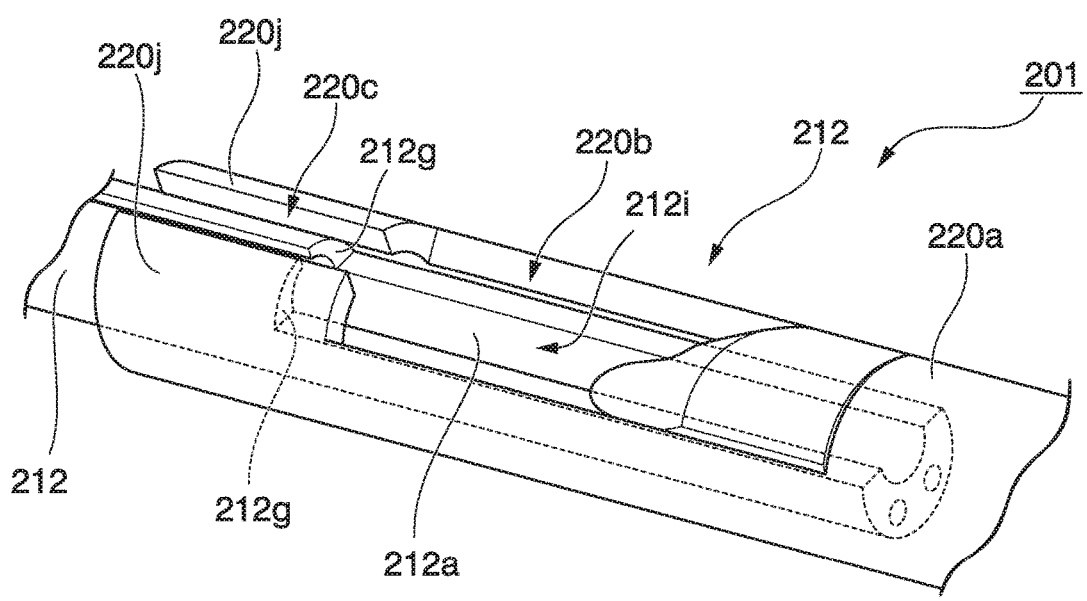
FIG. 66 is a schematic perspective view illustrating a constitution in the vicinity of a guide wire insertion opening according to the example of the treatment tool for an endoscope of the prior art.
Figure 67:
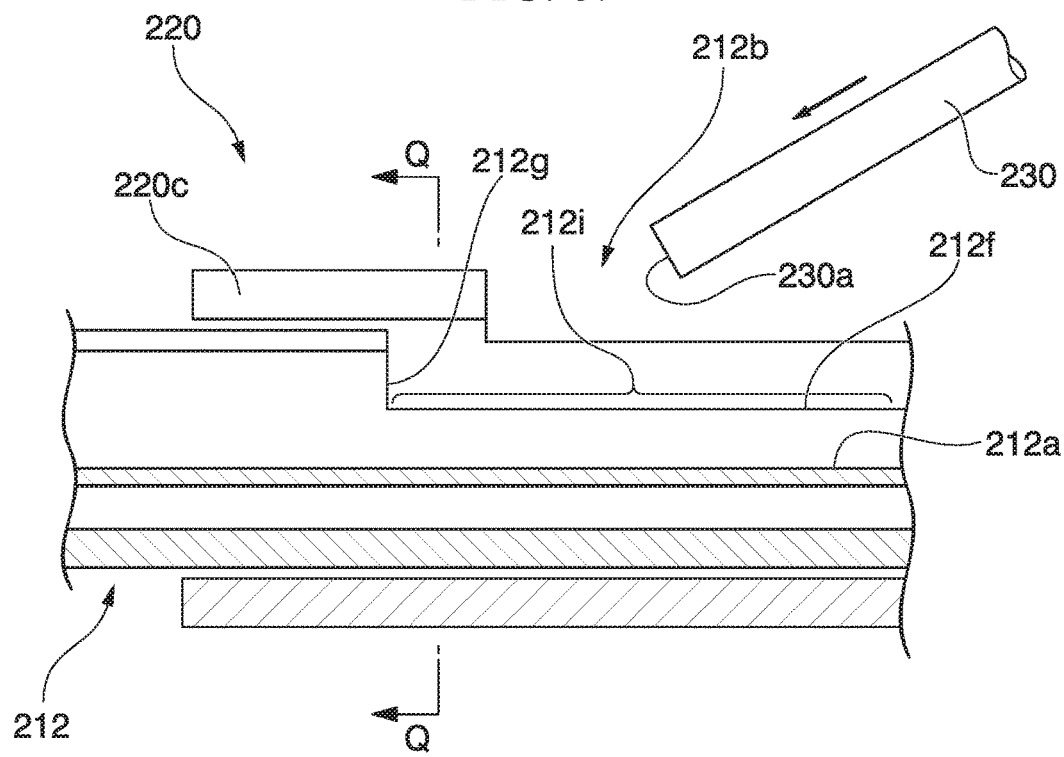
FIG. 67 is an explanatory view of operation of the treatment tool for an endoscope of the prior art according to the example.
Figure 68:
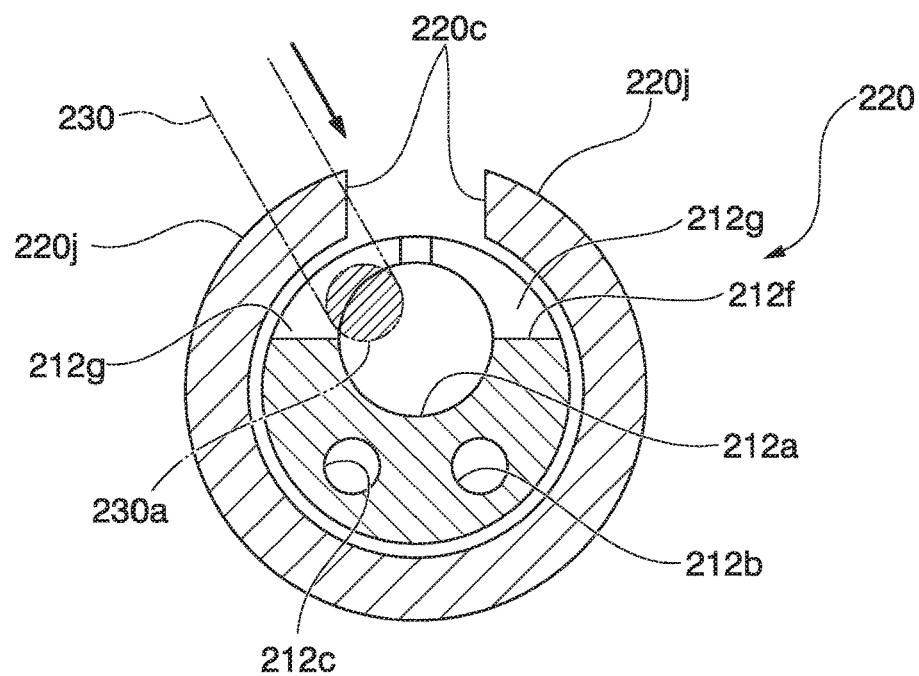
FIG. 68 is an explanatory view of operation of the treatment tool for an endoscope of the prior art according to the example.
Figure 69:
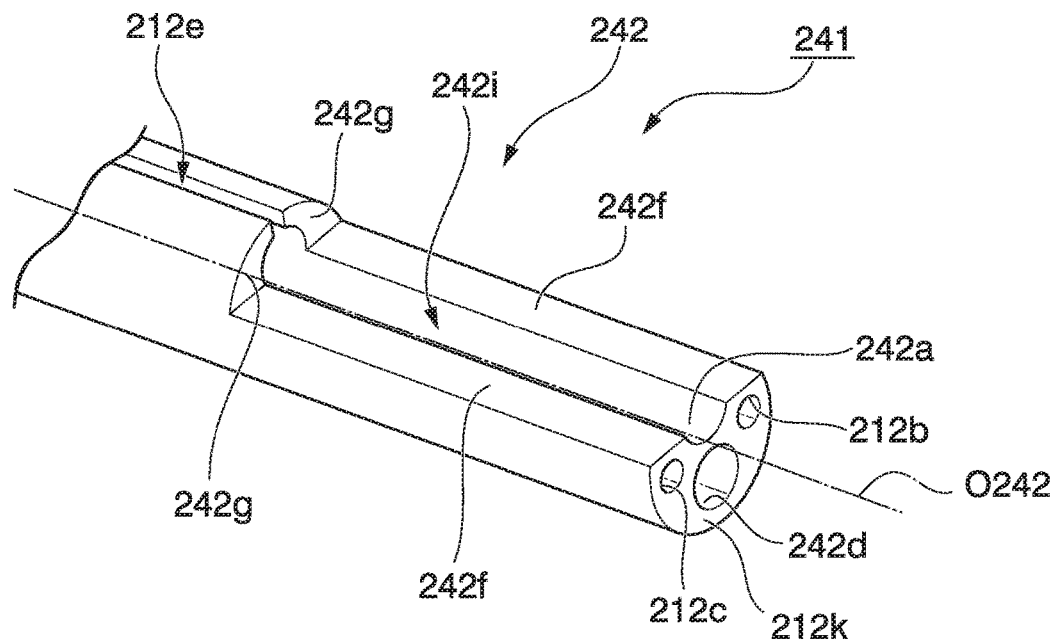
FIG. 69 is a schematic perspective view illustrating a proximal end portion of a multi-lumen tube according to another example of a treatment tool for an endoscope of the prior art.
Figure 70:
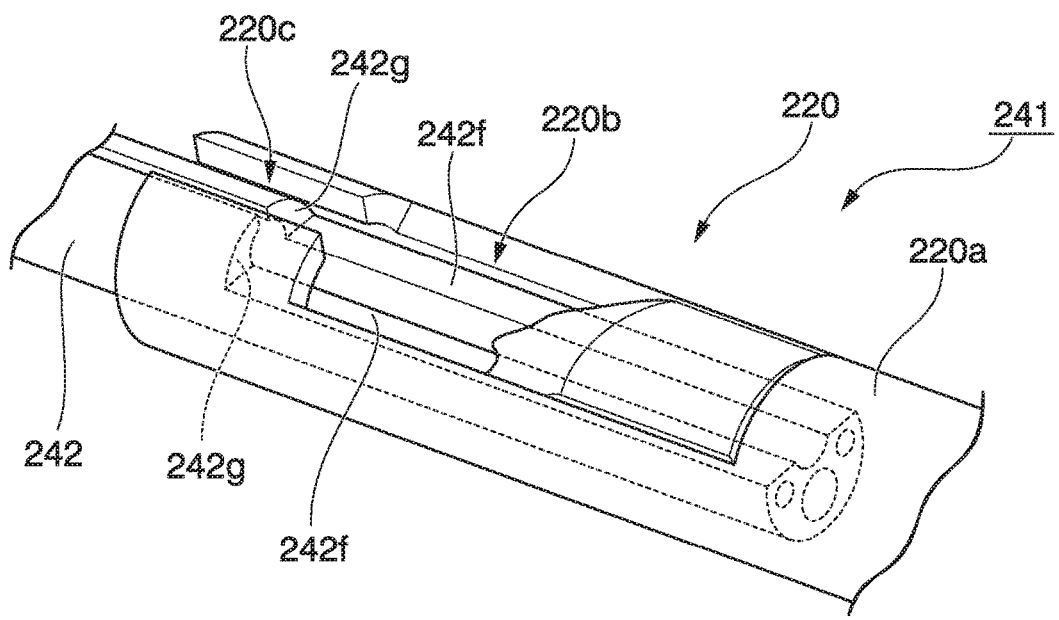
FIG. 70 is a schematic perspective view illustrating a constitution in the vicinity of a guide wire insertion opening according to another example of the treatment tool for an endoscope of the prior art.
Figure 71:
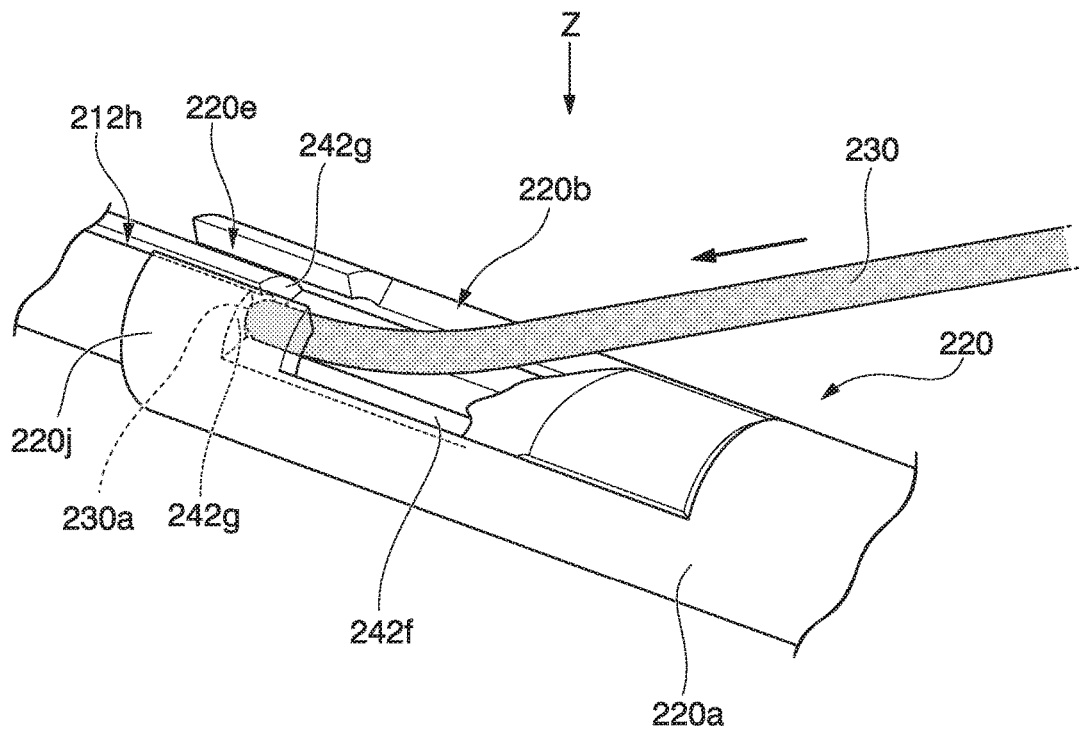
FIG. 71 is an explanatory view of operation of the treatment tool for an endoscope of the prior art according to another example.
Figure 72:
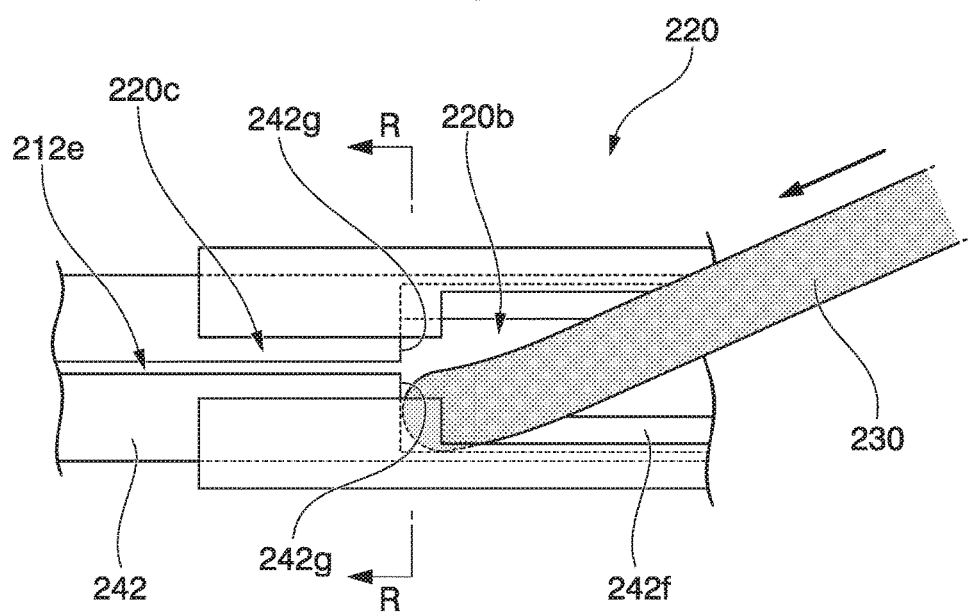
FIG. 72 is a plan view viewed from a direction of Z in FIG. 71.
Figure 73:
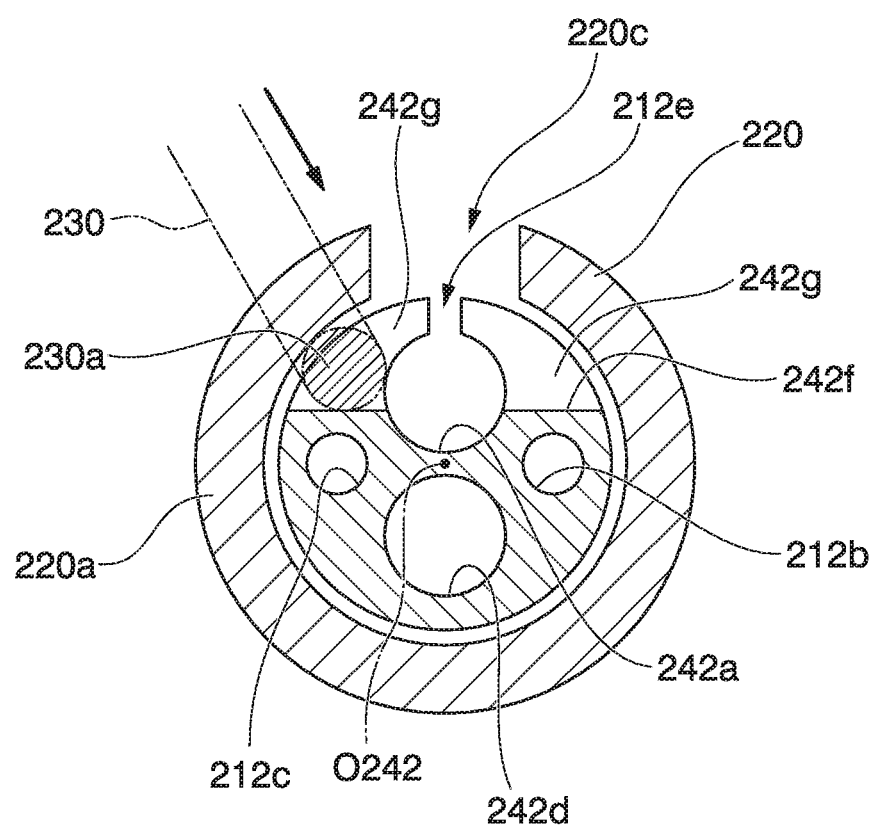
FIG. 73 is a cross-sectional view taken along line R-R in FIG. 72.

FIG. 59 is a perspective process explanatory view of a process for manufacturing the treatment tool for an endoscope according to the second embodiment of the present invention. FIG. 60 is a cross-sectional process explanatory diagram of the process for manufacturing the treatment tool for an endoscope according to the second embodiment of the present invention. FIG. 61 is a perspective process explanatory view of the process for manufacturing the treatment tool for an endoscope according to the second embodiment of the present invention. FIG. 62 is a cross-sectional process explanatory view of the process for manufacturing the treatment tool for an endoscope according to the second embodiment of the present invention. FIG. 63 is a perspective process explanatory view of the process for manufacturing the treatment tool for an endoscope according to the second embodiment of the present invention. FIG. 64 is a cross-sectional process explanatory view of the process for manufacturing the treatment tool for an endoscope according to the second embodiment of the present invention.

As illustrated in FIG. 59, when manufacturing the second sheath 42, first, a multi-lumen tube 52 in which the first lumen 12a, the second lumen 42b, the third lumen 42c, and the fourth lumen 12d are formed is manufactured.

Then, a process for forming the first side cut surface 42g, the second side cut surface 42h, and the axially cut surface 42f at an end portion of the multi-lumen tube 52, which becomes the first end portion E1 in the second sheath 42, is performed.

First, as illustrated in FIG. 59, the multi-lumen tube 52 is horizontally arranged so that the first lumen 12a is on an upper side thereof and the fourth lumen 12d is on a lower side thereof, and a core metal 102 is inserted into the first lumen 12a. Also, a core metal 103 is inserted into each of the second lumen 42b and the third lumen 42c.

The core metal 102 comes into contact with the lowermost inner circumferential surface of the first lumen 12a due to its own weight. The core metals 103 come into contact with the lowermost inner circumferential surface of the second lumen 42b and the third lumen 42c due to their own weight.

The core metal 102 and each of the core metals 103 are inserted to a position more inward than the position at which the first side cut surface 42g and the second side cut surface 42h intersect.

The core metal 102 and each of the core metals 103 are members configured to regulate a cutting amount of the cutter 100 configured to form the first side cut surface 42g and the second side cut surface 42h.

Also, each of the core metals 103 is also a member configured to guide movement of the cutter 100 when forming the axially cut surface 42f.

First, to form the first side cut surface 42g, cutting is performed by the cutter 100 from the outer circumferential side facing the first lumen 12a and the third lumen 42c in a cutting direction toward the multi-lumen tube 52.

A posture of the cutter 100 is different from the posture of the cutter 100 in the first embodiment in that, as illustrated in FIG. 60, the posture is an inclined direction that allows the cutting edge 100a to simultaneously come into contact with the core metals 102 and 103 to be inserted from the outer circumferential side facing the first lumen 12a and the third lumen 42c.

When such a cutting operation is performed, as illustrated in FIG. 60, the cutter 100 causes a cut portion in the multi-lumen tube 52 and forms the first side cut surface 42g in the cut portion. However, when the cutting edge 100a of the cutter 100 comes into contact with the core metals 102 and 103, the cutting cannot be performed further. Because of this, the first side cut surface 42g stops at the position of the cutting edge 100a.

An amount by which the first lumen 12a and the third lumen 42c are cut by the cutting edge 100a may be adjusted by appropriately setting the outer diameter of the core metals 102 and 103.

When the cutting edge 100a comes into contact with the core metals 102 and 103, the cutter 100 is pulled out.

Then, as illustrated in FIGS. 61 and 62, the cutter 100 is rotated around the vertical axis to cut into the multi-lumen tube 52 in a posture intersecting the first side cut surface 42g in an X-shape.

As illustrated in FIG. 62, the cutter 100 cuts until the cutting edge 100a comes into contact with the core metal 103 inserted into the second lumen 42b and the core metal 102. When the cutting edge 100a comes into contact with the core metals 102 and 103, the cutter 100 is pulled out.

As a result, the second side cut surface 42h is formed.

In this way, at a side surface of the multi-lumen tube 52, the first side cut surface 42g and the second side cut surface 42h intersecting in an X-shape at the point P when viewed from the diametric direction are formed.

Then, the axially cut surface 42f is formed.

First, the core metal 102 is retracted from the first lumen 12a. Then, the cutter 100 is placed on an upper portion of each of the core metals 103 extending from the multi-lumen tube 52. Then, as illustrated in FIGS. 63 and 64, the cutter 100 performs cutting with a direction from the end surface 12k along the central axis of the multi-lumen tube 52 as a cutting direction.

The cutting edge 100a of the cutter 100 retains a posture orthogonal to the central axis O32 of the multi-lumen tube 32.

Further, the cutter 100 is in contact with each of the core metals 103 from above and horizontally moves with each of the metal cores 103 as a guide. Due to such a cut operation of the cutter 100, the axially cut surface 42f is formed from the end surface 12k along a horizontal plane parallel to a central axis O52 of the multi-lumen tube 52 (see FIG. 64).

An end portion of the multi-lumen tube 52 is divided into two with the axially cut surface 42f as a boundary therebetween by the cutting operation.

When the cutting edge 100a intersects the first side cut surface 42g and the second side cut surface 42h closest to the end surface 12k, a cutout portion (not illustrated), which is the same as the cutout portion 32B of the first embodiment, is spaced apart. As a result, as illustrated in FIG. 63, a tube main body portion 52A is formed.

The cutting operation is stopped when the cutting edge 100a of the cutter 100 slightly moves from the point P to the distal end side as seen from the diametric direction.

The piece-like parts 42i and 42j are formed in a range in which the first side cut surface 42g and the second side cut surface 42h overlap the axially cut surface 42f when viewed from the diametric direction by such a cutting operation.

Then, the cutter 100 and each of the core metals 103 are removed.

In this way, the tube main body portion 52A in which a side portion is cut out is formed by forming the first side cut surface 42g, the second side cut surface 42h, and the axially cut surface 42f.

Then, the slit 12e is processed from the point P of the tube main body portion 52A along the central axis O52 in the same way as the first embodiment. In this way, when the slit 12e is formed throughout an entire length of the tube main body portion 52A, the second sheath 42 illustrated in FIG. 56 is formed.

The treatment tool 41 can be manufactured by performing the same assembly process as the assembly process of the second sheath 12 according to the first embodiment for the second sheath 42 except that the tube 43 is inserted into the second lumen 42b and the third lumen 42c at the first end portion E1.

Although the treatment tool 41 includes the first side cut surface 42g, the second side cut surface 42h, and the axially cut surface 42f instead of the first side cut surface 12g, the second side cut surface 12h, and the axially cut surface 12f, the treatment tool 41 performs the same action as the treatment tool 1.

Therefore, according to the treatment tool 41, even when the guide wire 30 deviates from the guide wire lumen at a time of inserting the guide wire 30, the guide wire 30 moves along the first side cut surface 42g and the second side cut surface 42h which intersect in an X-shape. Because of this, according to the treatment tool 41, the guide wire can be easily inserted into the guide wire lumen when the treatment tool 41 includes a multi-lumen sheath.

In the description of each of the above embodiments, the case in which the axially cut surface extends further toward the distal end side than the point P in the axial direction of the second sheath has been described as an example. However, the axially cut surface may stop further toward the proximal end side than the point P as long as the axially cut surface intersects the first side cut surface and the second side cut surface at the side of the end surface 12k.

In the description of each of the above embodiments, the case in which the slit 12e is formed after the first side cut surface, the second side cut surface, and the axially cut surface are formed has been described as an example. However, the slit 12e may be formed before any of the first side cut surface, the second side cut surface, and the axially cut surface.

In the description of each of the above embodiments, the case in which the axially cut surface is formed after the first side cut surface and the second side cut surface are formed has been described as an example. However, the first side cut surface and the second side cut surface may be formed after forming the axially cut surface.

In the description of each of the above embodiments, the case in which cutting is performed from the end surface (the end surface 12k) in the axial direction of the first end portion of the multi-lumen sheath when forming the axially cut surface has been described as an example. However, the axially cut surface may also be formed further toward the distal end side than the end surface 12k as long as the axially cut surface is at the side of the end surface 12k in the multi-lumen sheath. In this case, it is not necessary for the cutter forming the axially cut surface to cut into the end surface 12k.

Although the embodiments of the present invention have been described above in detail with reference to the drawings, the specific constitution is not limited to the above embodiments, and design changes and the like within a scope not departing from the gist of the present invention are also included. All of the above-described elements can be implemented by being appropriately combined within the scope of the technical spirit of the present invention or being deleted.

What is claimed is:

1. A treatment tool for an endoscope, the treatment tool comprising:
   a multi-lumen sheath comprising:
      a plurality of lumens including a guide wire lumen that is configured to receive a guide wire, and
      a first slit extending along an axial direction of the guide wire lumen, and configured such that the guide wire can be taken in and out of the guide wire lumen via the first slit; and
   a sheath-retaining part including a tubular part configured to retain a first end portion of the multi-lumen sheath, the tubular part having a guide wire insertion opening formed at a side surface of the tubular part, the guide wire insertion opening including, in order from a distal end side:
      a second slit overlapping the first slit when viewed from a diametric direction and having a wider clearance than the first slit, and
      a main opening having a wider opening width than the second slit,
   wherein the first end portion of the multi-lumen sheath has:
      a first side cut surface and a second side cut surface that intersect in an X-shape having the first slit of the multi-lumen sheath as a center when viewed from the diametric direction, and that are formed by cutting the multi-lumen sheath from an outer circumferential surface of the multi-lumen sheath to an inside of the guide wire lumen;
an axially cut surface formed by cutting the multi-lumen sheath in a plane parallel to a central axis of the guide wire lumen from an axial end surface of the first end portion of the multi-lumen sheath to a position intersecting a part of the first side cut surface and a part of the second side cut surface;
a first end portion opening that is surrounded by a portion of the first end portion disposed in the vicinity of the axial end surface, the first side cut surface, the second side cut surface, and the axially cut surface, and that communicates with the guide wire lumen and is formed at a position overlapping the main opening;
a first part having the first side cut surface and the axially cut surface at an outer edge thereof; and
a second part having the second side cut surface and the axially cut surface at an outer edge thereof.

2. The treatment tool according to claim 1, wherein the first side cut surface and the second side cut surface are orthogonal to the axially cut surface.

3. The treatment tool according to claim 1, wherein the first side cut surface and the second side cut surface are arranged at a position distal to the guide wire insertion opening and overlapping the tubular part when viewed from the diametric direction.

4. The treatment tool according to claim 1, wherein the first part is a first triangular part, and the second part is a second triangular part.

5. A method for manufacturing a treatment tool for an endoscope,
the treatment tool including:
a multi-lumen sheath having a plurality of lumens including a guide wire lumen that is configured to receive a guide wire, and a first slit extending along an axial direction of the guide wire lumen and configured such that the guide wire can be taken in and out of the guide wire lumen via the first slit, and
a sheath-retaining part including a tubular part configured to retain a first end portion of the multi-lumen sheath,
the method comprising:
forming, in the first end portion of the multi-lumen sheath, a first side cut surface and a second side cut surface by forming an X-shape intersecting in an axial direction of the multi-lumen sheath and cutting the multi-lumen sheath from an outer circumferential surface of the multi-lumen sheath to an inside of the guide wire lumen;
forming, in the first end portion of the multi-lumen sheath, an axially cut surface by cutting the multi-lumen sheath in plane parallel to a central axis of the guide wire lumen from an axial end surface of the first end portion of the multi-lumen sheath to a position intersecting a part of the first side cut surface and a part of the second side cut surface, and thereby forming, in the first end portion of the multi-lumen sheath, a tubular part opening communicating with the guide wire lumen, a first part having the first side cut surface and the axially cut surface at an outer edge thereof, and a second part having the second side cut surface and the axially cut surface at an outer edge thereof; and
forming, in the multi-lumen sheath, a first slit passing through an intersection part of the first side cut surface and the second side cut surface from the tubular part opening, extending along the axial direction of the guide wire lumen, and communicating with the guide wire lumen.

6. The method for manufacturing a treatment tool according to claim 5, wherein the first part is a first triangular part, and the second part is a second triangular part.

* * * * *